(12) United States Patent
Friedman et al.

(10) Patent No.: US 9,399,063 B2
(45) Date of Patent: Jul. 26, 2016

(54) COMPOSITIONS AND METHODS TO MODULATE CELL ACTIVITY

(75) Inventors: Jeffrey Friedman, New York, NY (US); Sarah Stanley, New York, NY (US)

(73) Assignee: THE ROCKEFELLER UNIVERSITY, New York, NY (US)

( * ) Notice: Subject to any disclaimer, the term of this patent is extended or adjusted under 35 U.S.C. 154(b) by 0 days.

(21) Appl. No.: 14/239,427

(22) PCT Filed: Aug. 24, 2012

(86) PCT No.: PCT/US2012/052391
§ 371 (c)(1),
(2), (4) Date: Aug. 12, 2014

(87) PCT Pub. No.: WO2013/029025
PCT Pub. Date: Feb. 28, 2013

(65) Prior Publication Data
US 2014/0348825 A1     Nov. 27, 2014

Related U.S. Application Data

(60) Provisional application No. 61/526,985, filed on Aug. 24, 2011.

(51) Int. Cl.
*A61K 9/14*     (2006.01)
*A61K 41/00*    (2006.01)
(Continued)

(52) U.S. Cl.
CPC ............ *A61K 41/0028* (2013.01); *A61K 9/16* (2013.01); *A61K 9/1611* (2013.01); *A61K 33/26* (2013.01); *B82Y 5/00* (2013.01); *C07K 14/47* (2013.01); *C07K 14/705* (2013.01); *C07K 2319/00* (2013.01); *C07K 2319/035* (2013.01); *C07K 2319/21* (2013.01); *C07K 2319/30* (2013.01); *C07K 2319/60* (2013.01)

(58) Field of Classification Search
CPC .................... A61K 9/16; A61K 9/1611
See application file for complete search history.

(56) References Cited

U.S. PATENT DOCUMENTS 8,435,762 B2   5/2013   Sternson et al.
8,957,036 B2   2/2015   Cascio et al.
(Continued)

OTHER PUBLICATIONS

Huang et al, "Remote Control of Ion Channels and Neursons Through Magnetic-Field Heating of Nanoparticles", Nature naotechnology, Aug. 2010, vol. 5, No. 8, pp. 602-606.*
(Continued)

*Primary Examiner* — Carlos Azpuru
(74) *Attorney, Agent, or Firm* — Hoffmann & Baron, LLP

(57) ABSTRACT

The present invention provides methods and compositions for the remote control of cell function based on the use of radiofrequency waves to excite nanoparticles targeted to specific cell types. The nanoparticles may be applied to the target cell extracellularly and/or expressed intracellularly. The cell type of interest expresses a temperature sensitive channel wherein excitation of the nanoparticles results in a localized temperature increase that is transduced into a cellular response. Such cellular responses may include, for example, increases in gene expression resulting in production of one or more physiologically active proteins. The expression of such proteins can be used to treat a variety of different inherited or acquired diseases or disorders in a subject. Accordingly, the invention provides a generic approach for treatment of any disease associated with a protein deficiency.

26 Claims, 56 Drawing Sheets

(51) Int. Cl.
| | |
|---|---|
| *A61K 9/16* | (2006.01) |
| *B82Y 5/00* | (2011.01) |
| *C07K 14/705* | (2006.01) |
| *C07K 14/47* | (2006.01) |
| *A61K 33/26* | (2006.01) |

(56) References Cited

U.S. PATENT DOCUMENTS

| | | |
|---|---|---|
| 2004/0023203 A1 | 2/2004 | Miesenbock et al. |
| 2011/0034753 A1 | 2/2011 | Dobson et al. |

OTHER PUBLICATIONS

Huang, H. et al., "Remote Control of Ion Channels and Neurons Through Magnetic-Field Heating of Nanoparticles," Nature Nanotechnology, Aug. 2010, vol. 5, No. 8, pp. 602-606.

International Search Report in International Application No. PCT/US2012/052391 dated Jan. 22, 2013.

Johns et al., Inducible Genetic Suppression of Neuronal Excitability, The Journal of Neuroscience, vol. 19, Issue 5, Mar. 1, 1999, pp. 1691-1697.

Nitabach et al., Electrical Silencing of Drosophila Pacemaker Neurons Stops the Free-Running Circadian Clock, Cell, vol. 109, Issue 4, May 17, 2002, pp. 485-495.

Lerchner et al., Reversible Silencing of Neuronal Excitability in Behaving Mice by a Genetically Targeted, Ivermectin-Gated Cl-Channel, Neuron, vol. 54, Issue 1, Apr. 5, 2007, pp. 35-49.

Cheng et al., Suppression of Neuronal Hyperexcitability and Associated Delayed Neuronal Death by Adenoviral Expression of GABAc Receptors, The Journal of Neuroscience, vol. 21(10), May 15, 2001, pp. 3419-3428.

Cooper et al., Host Cell-Specific Folding and Assembly of the Neuronal Nicotinic Acetylcholine Receptor α7 Subunit, vol. 68(5), 1997, pp. 2140-2151.

Ehrengruber et al., Activation of heteromeric G protein-gated inward rectifier K+ channels overexpressed by adenovirus gene transfer inhibits the excitability of hippocampal neurons, Proc. Natl. Acad. Sci. USA, vol. 94, Jun. 1997, pp. 7070-7075.

Khakh et al., Activation-dependent changes in receptor distribution and dendritic morphology in hippocampal neurons expressing P2X2—green fluorescent protein receptors, Proc. Natl. Acad. Sci. USA, vol. 98, Apr. 24, 2001, pp. 5288-5293.

Nadeau et al., ROMK1 (Kir1.1) Causes Apoptosis and Chronic Silencing of Hippocampal Neurons, J. Neurophysiol., vol. 84(2), Aug. 2000, p. 1062-1075.

Dkada et al., Functional Correlation of GABA(a) Receptor alpha Subunits Expression with the Properties of IPSCs in the Developing Thalamus, J. Neurosci., vol. 20(6), Mar. 15, 2000, pp. 2202-2208.

Slimko et al., Selective Electrical Silencing of Mammalian Neurons In Vitro by the Use of Invertebrate Ligand-Gated Chloride Channels, J. Neurosci., vol. 22(17), Sep. 1, 2002, pp. 7373-7379.

Tobin et al., Combinatorial Expression of TRPV Channel Proteins Defines Their Sensory Functions and Subcellular Localization in C. elegans Neurons, Neuron, vol. 35, Jul. 18, 2002, pp. 307-318.

White et al., Molecular genetic approaches to the targeted suppression of neuronal activity, Current Biology, vol. 11 (24), Dec. 11, 2001, pp. R1041-R1053.

Caterina et al., The capsaicin receptor: a heat-activated ion channel in the pain pathway, Nature, vol. 389, Oct. 23, 1997, pp. 816-824.

Kupper et al., Recombinant Kv1.3 potassium channels stabilize tonic firing of cultured rat hippocampal nuerons, Pflugers Archiv.—Eur. J. Physiol., vol. 443, Feb. 2002, pp. 541-547.

McKemy et al., Identification of a cold receptor reveals a general role for TRP channels in thermosensation, Nature, vol. 416, Mar. 7, 2002, pp. 52-58.

Slimko et al., Selective silencing of mammalian neurons: strategies using chloride channels, Neuroscience, 2000 Abstract.

Slimko et al., Selective silencing of mammalian neurons: strategies using chloride channels, Neuroscience, 2001 Abstract.

* cited by examiner

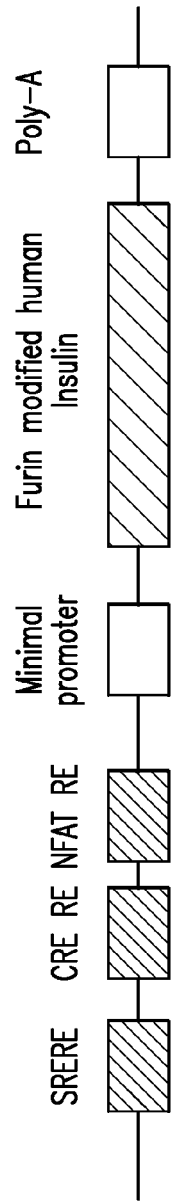
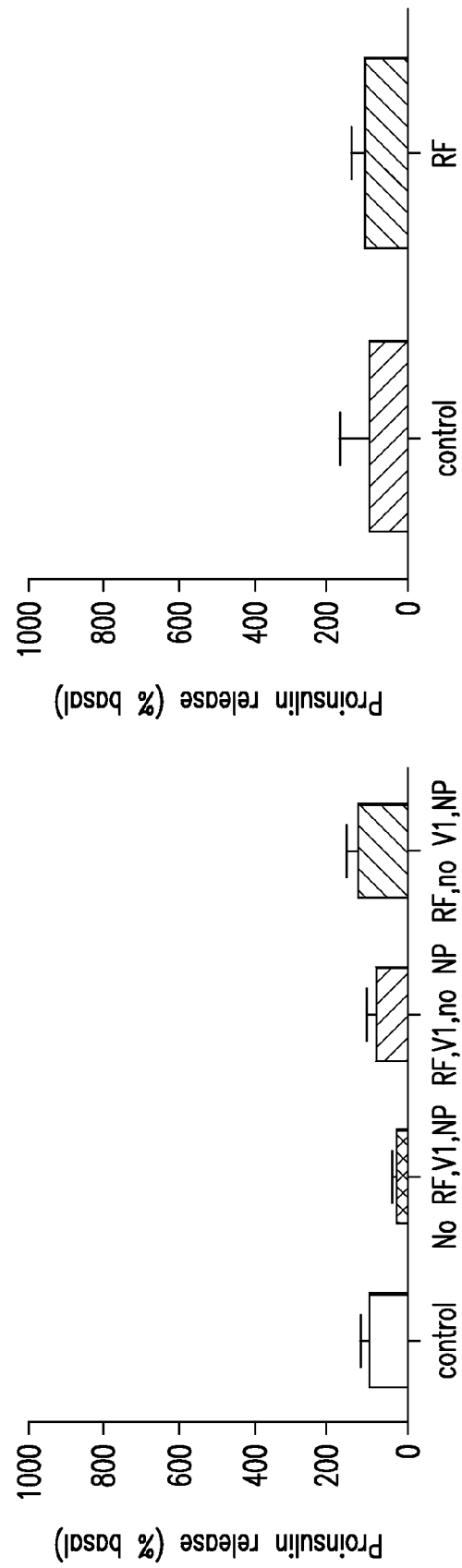
FIG. 5A
FIG. 5B
FIG. 5C

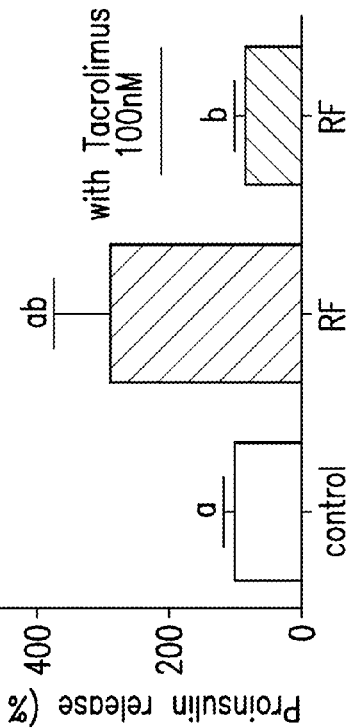
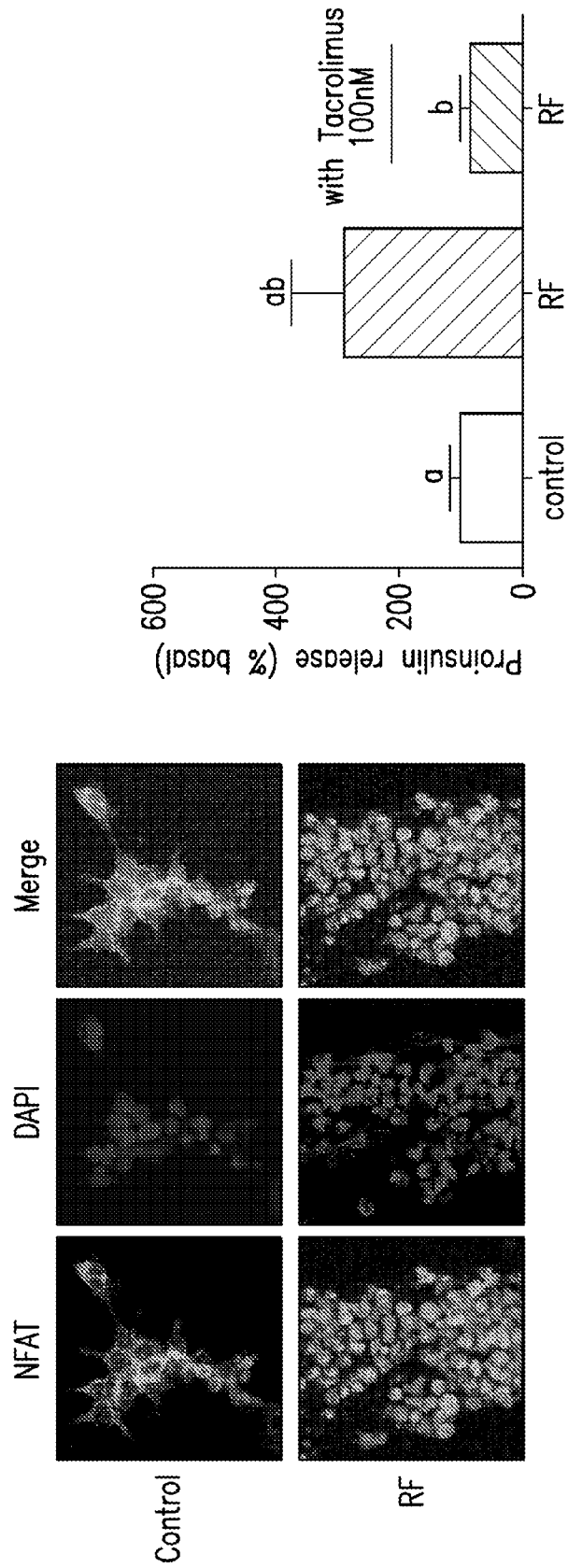
FIG. 5D
FIG. 5E

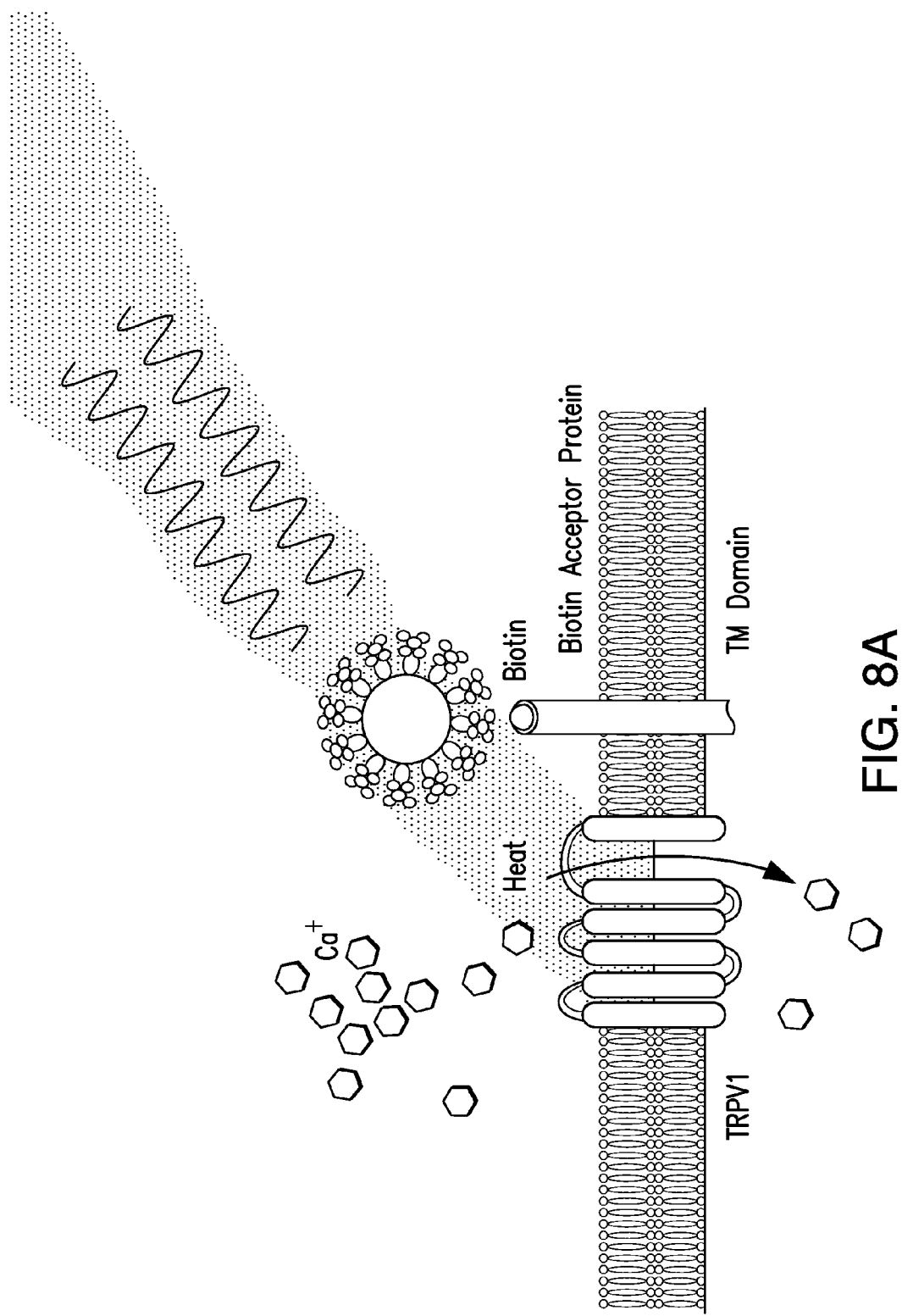

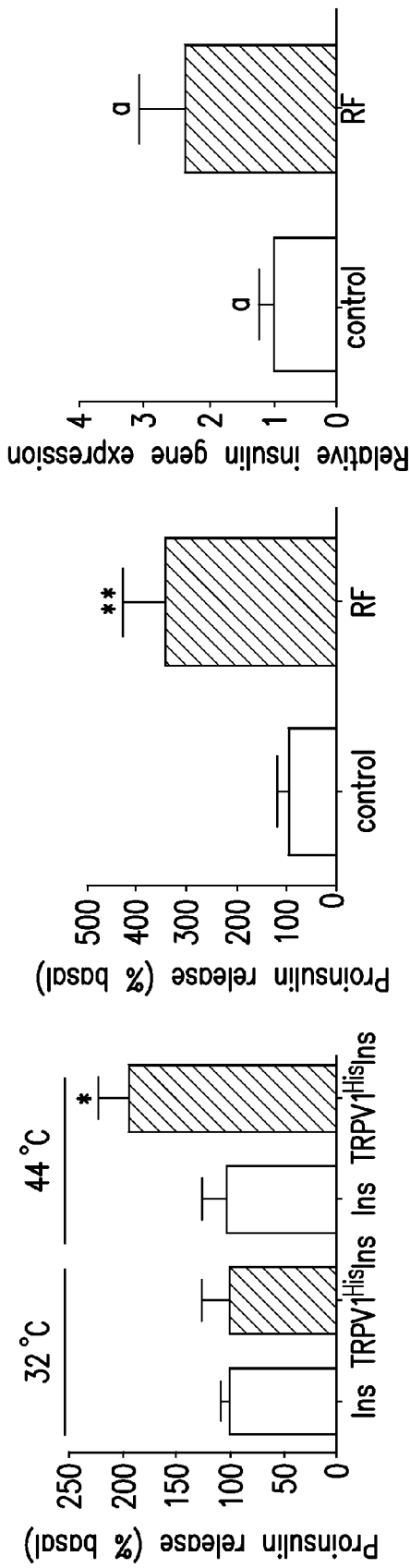

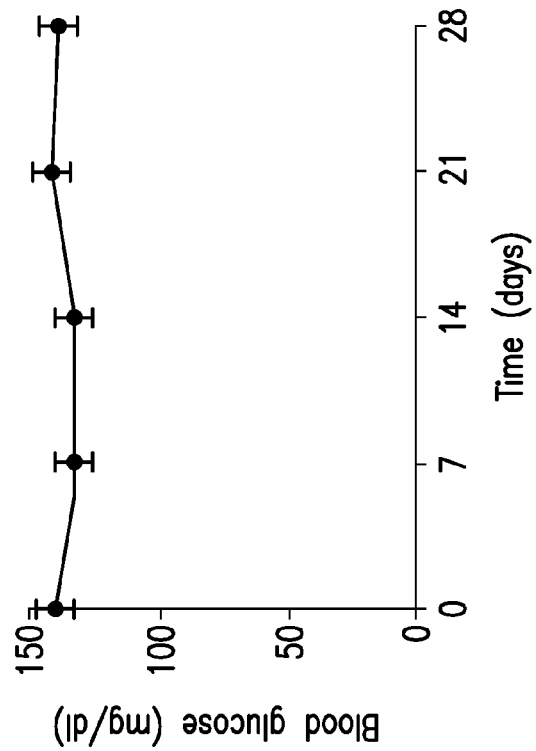
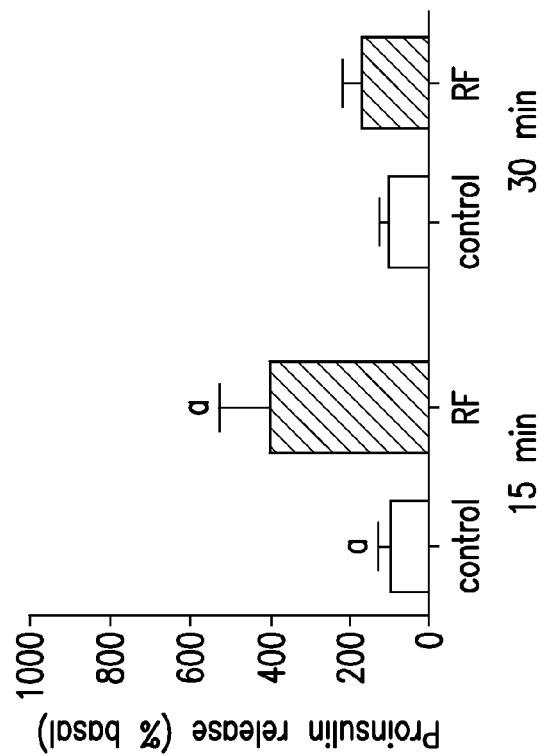
FIG. 9E
FIG. 9D

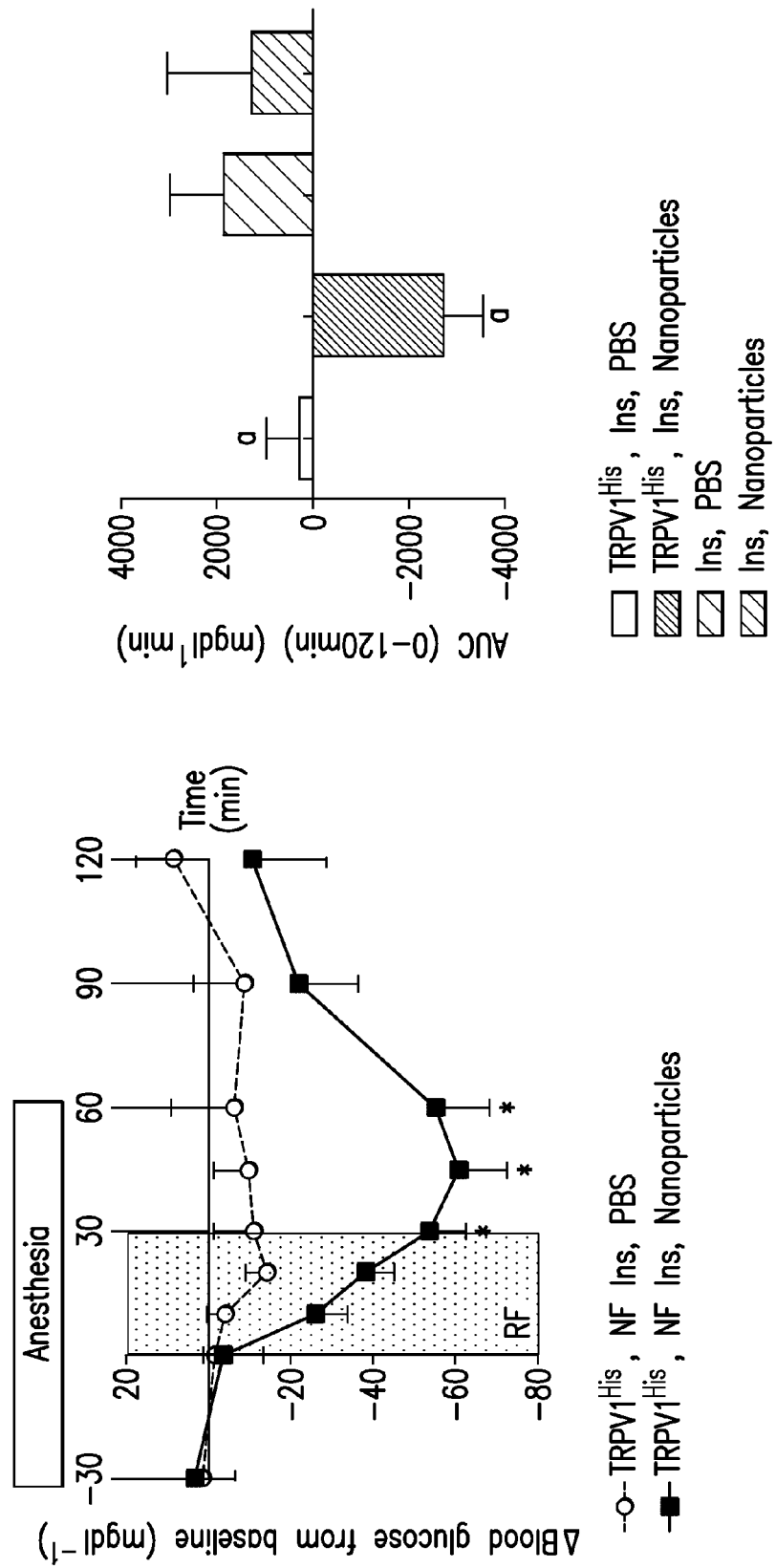

COMPOSITIONS AND METHODS TO MODULATE CELL ACTIVITY

The invention disclosed herein was made with United States Government support under NIH Grant No. R01 GM095654 from the National Institutes of Health. Accordingly, the United States Government has certain rights in this invention.

CROSS-REFERENCE TO RELATED APPLICATIONS

This is a national phase application based on the PCT International Patent Application No. PCT/US2012/052391, filed on Aug. 24, 2012, the entire contents of which is incorporated herein by reference.

FIELD OF THE INVENTION

The present invention provides methods and compositions for the remote control of cell function based on the use of radiofrequency waves to excite nanoparticles targeted to specific cell types. The cell type of interest expresses a temperature sensitive channel wherein excitation of the nanoparticles results in a localized temperature increase that is transduced into a cellular response. Such cellular responses may include, for example, increases in gene expression resulting in production of one or more physiologically active proteins. The expression of such proteins can be used to treat a variety of different inherited or acquired diseases or disorders in a subject. Accordingly, the invention provides a generic approach for treatment of any disease associated with a protein deficiency.

BACKGROUND OF THE INVENTION

The tools for dissecting the contribution of specific cells to physiological functions and particular behavior have evolved over recent years. Initial studies used electrical and chemical lesions to ablate both neurons and fibers in defined regions. Later investigations made use of direct stimulation through implanted electrodes, however, these studies were hampered by variable activation, the need for permanent implants, and tissue damage. As an alternative to these approaches, recent techniques make use of drug inducible systems to alter gene expression or ion channels to modulate cell activity (Lerchner et al., Neuron 54:35-49). By allowing the selective passage of cations or anions, families of ion channels regulate intracellular ion concentrations, which in turn modulate intracellular functions according to the cell type. The use of ion channels has many advantages; their structure and function are relatively well described; they have a rapid time course of activation, and a broad range of channels exist in mammalian and non-mammalian cells, which may be exploited in the search for the optimum means of modifying cellular activity. This approach was first validated by transgenic expression of a drug-gated channel to modify behavior, however, the time course of effects was relatively slow (hours to days) due to irreversible effects of the ligand. Recently, the non-mammalian channelrhodopsin (ChR2) gene, a light activated cation, has been employed to rapidly activate molecularly defined neurons when exposed to blue light (Boyden E S et al. 2005 Nat Neurosci 8:1263-1268). This system gives anatomical specificity and temporal control but also has limitations. For example, there are only two variants for activation, thereby limiting the potential for combinatorial activation, and more importantly, activation in vivo requires fiber optic light delivery via implanted devices that are invasive and can interfere with behavior.

The present invention provides methods and compositions for the remote control of cell function based on the use of radiofrequency waves to excite nanoparticles targeted to specific cell types. The invention, uses Nanoparticle Induced Circuit Excitation (NICE) to, for example, regulate ion channels as a means for stimulating the activity of specific cells remotely and non-invasively.

SUMMARY OF THE INVENTION

The invention described herein utilizes Nanoparticle Induced Circuit Excitation (NICE), which encompasses compositions and methods that have been developed for stimulating the activity of specific cells remotely and non-invasively. The present invention provides methods and compositions based on the use of radiofrequency waves to excite nanoparticles targeted to specific cell types. The cell type of interest expresses a temperature sensitive channel wherein excitation of the nanoparticles results in a localized temperature increase that is transduced into a cellular response. The excitation of the nanoparticles results in a localized temperature increase that is transduced into a cellular response such as, for example, an increase in gene expression. Such increases in gene expression may result in production of one or more physiologically active proteins. The expression of such proteins can be used to treat a variety of different inherited or acquired diseases or disorders in a subject.

According to one aspect, the described invention provides a method to remotely stimulate the activity of a cell type of interest wherein the nanoparticles are externally applied. Such a method comprises: (i) administering to a cell population nanoparticles selective for the cell type of interest; and (ii) applying a radiofrequency field to remotely activate the nanoparticles. Said activation of the nanoparticles results in stimulation of the activity of the cell type of interest.

Alternatively, cells may be engineered to synthesize nanoparticles intracellularly. For example, as described herein, the iron storage protein ferritin, which forms a naturally occurring iron nanoparticle, was modified to form a ferritin fusion protein composed of a ferritin light chain fused to ferritin heavy chain with a flexible linker region. Heating of the iron core by a RF magnetic field opens the TRPV1 channel to trigger calcium entry, increasing proinsulin gene expression and triggering insulin release in vitro. This results in decrease blood glucose in vivo.

In another embodiment of the invention as described herein, modification using intracellular nanoparticles uses a modified TRPV1 with a camelid antibody to GFP fused to the N-terminal of TRPV1 and a modified ferritin fusion protein with EGFP fused to the N-terminal of ferritin light chain-linker-ferritin heavy chain. Heating of the iron core of the ferritin attached to the TRPV1 triggers calcium entry and increases proinsulin gene expression and proinsulin release in vitro.

In a non limiting embodiment of the invention, said nanoparticles may be paramagnetic nanoparticles.

According to another aspect of the invention, a method is provided to remotely stimulate the activity of a cell type of interest in a subject, the method comprising: (i) administering to the subject nanoparticles selective for the cell type of interest; and (ii) applying a radiofrequency field to remotely activate the nanoparticles. Said activation of the nanoparticles results in stimulation of the activity of the cell type of interest in a subject.

Activities of the cell that may be stimulated include, for example, cellular responses such as cell proliferation and/or differentiation, apoptosis, activation of signal transduction pathways, neuronal activation, development of long term potentiation and/or regulation of gene expression.

Further, the invention provides a method to stimulate the activity of a cell type of interest in a subject, the method comprising steps: (a) administering to the subject modified cells of interest that comprise nanoparticles that are selective for the cell type of interest; and (b) applying a radiofrequency field to remotely activate the nanoparticles. Said activation of the nanoparticles results in stimulation of the activity of the cell type of interest in a subject.

The present invention can be used in a variety of different clinical settings. For example, the technology can be used to control the expression of physiologically active proteins for used in treatment of various inherited or acquired disorders or diseases. For example, stem cells, such as induced pluripotent stem cells (iPSC) or autologous mesenchymal stem cells engineered to express NICE constructs could act as autografts enabling external control of cell function. NICE dependent calcium entry can then be used to regulate functions including hormone release, muscle contraction, or neural activity. Regulated hormone expression and release can facilitate the treatment of several endocrine conditions such as diabetes. Neuronal stimulation can be used therapeutically in several debilitating conditions such as Parkinson's disease (subthalamic stimulation) and stroke (transcranial direct current stimulation), as well as for pain relief and gastroparesis (Benabid A L. et al, 2009 Lancet Neurol 8:67-81; Schlaug G. et al. 2008 Arch Neurol 65:1571-1576; Nnoaham K E, Kumbang J 2008 Cochrane Database Syst RevCD003222; Maranki J, Parkman H P 2007 Curr Gastroenterol Rep 9:286-294).

Functional nanoparticles, prepared using methods known to those skilled in the art, can be targeted by coating with recombinant antibodies directed to endogenous cell specific surface proteins. These applications and the approaches can be applied in animals using the NICE techniques.

Further, the methods and compositions of the invention provide a means for dissecting the contributions of defined cell populations to physiology. The present invention makes it possible to decorate different cell types with nanoparticles tuned to different frequencies, thus allowing one to simultaneously activate ensembles of defined cells even if they are in proximity. The described invention provides for selective modification of cellular function non-invasively both in vitro and in vivo. At present, there are no methods for anatomically discrete, temporally controlled, non-invasive cell activation. Such a technique allows one to study the roles of cell populations in physiological processes, in particular those functions that are, or would be, perturbed by invasive methods.

Further, the invention proves non-human transgenic animals containing different cell types that can be activated remotely through the targeting of nanoparticles to the surface of said cells. The transgenic animals provide an in vivo means for studying the contributions of defined populations of cells to physiology. Further, the transgenic animals of the invention may be used as animal model systems for the screening, identification and testing of useful therapeutic compounds.

Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., Manipulating the Mouse Embryo, (Cold Spring Harbor Laboratory Press, Cold Spring Harbor, N.Y., 1986). Similar methods are used for production of other transgenic animals.

The described invention provides, for example, methods to remotely modulate cell function in vertebrates and apply NICE to (i) modify glucose metabolism (ii) activate dopaminergic neurons in the midbrain that control reward and (iii) use a combinatorial activation scheme to regulate feeding behavior.

As described in detail below, a specific embodiment of the invention makes use of a unique combination of four components: (i) a radiofrequency electromagnetic field; (ii) cell-specific expression of a nanoparticle tether; (iii) metallic/metal oxide nanoparticles; and (iv) a temperature sensitive TRPV cation channel to induce a tunable increase in intracellular calcium.

The present invention also provides pharmaceutical compositions comprising nanoparticles that are selective for a cell type expressing a temperature sensitive channel. Alternatively, pharmaceutical compositions of the invention may comprise modified cells expressing a temperature sensitive channel of interest and decorated with nanoparticles selective for said cells.

DETAILED DESCRIPTION OF THE INVENTION

Figure 1:
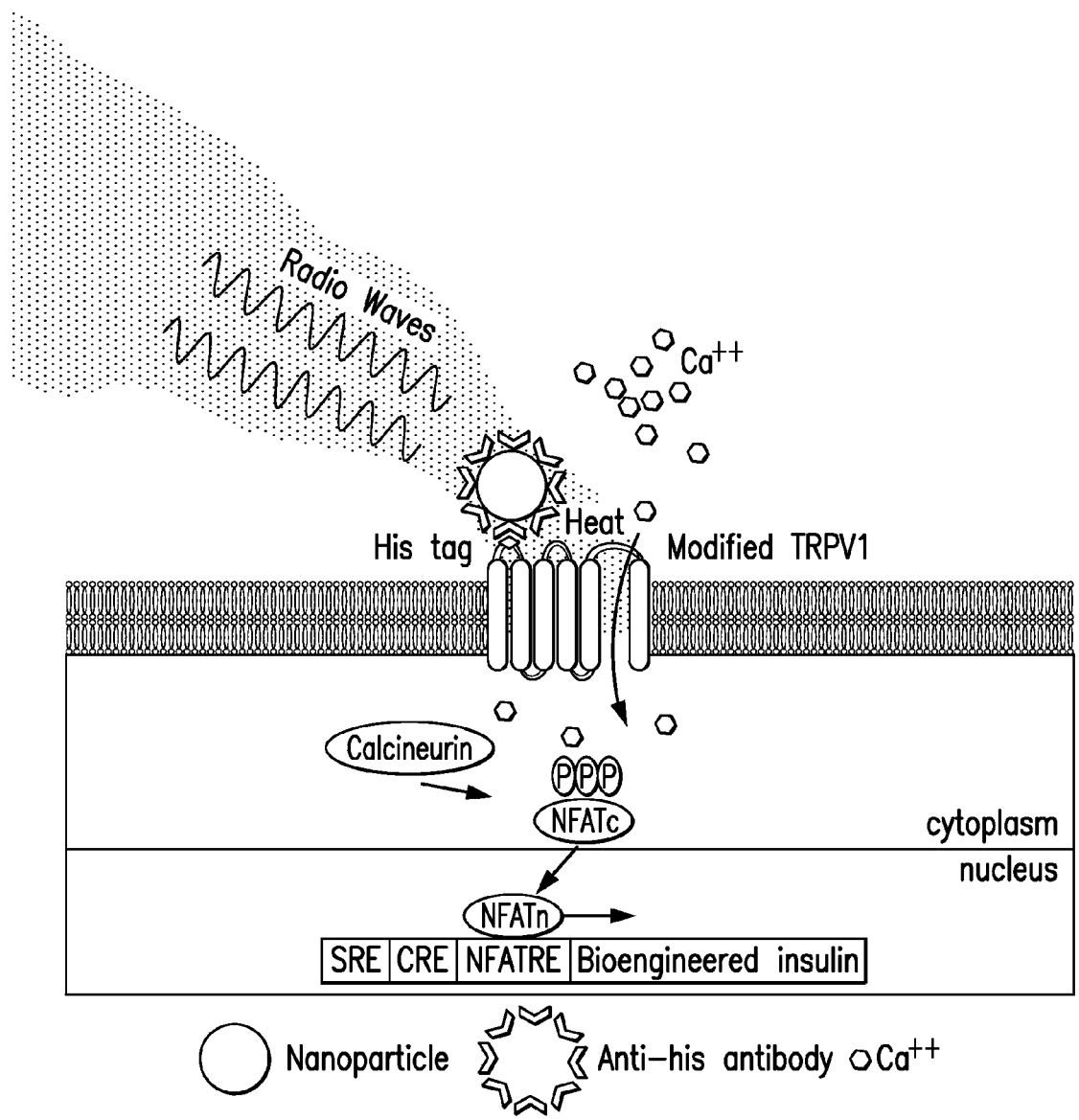
FIG. 1. Nanoparticles induced cell excitation to increase insulin expression and release in vitro. Schema of nanoparticle-induced cell activation and gene expression. Antibody-coated ferrous oxide nanoparticles bind to a unique epitope, His×6, in the first extracellular loop of the temperature-sensitive TRPV1 channel. Exposure to a RF field induces local nanoparticle heating, which opens temperature-sensitive TRPV1 channels. Calcium entry triggers downstream pathways, such as activation of calcineurin, leading to dephosphorylation of NFAT and translocation to the nucleus. Here, NFAT binds to upstream response elements to initiate gene expression of a bioengineered human insulin gene. Additional calcium-dependent signal transduction pathways also stimulate gene expression via binding to SRE and CRE. P indicates a phosphate group.
Figure 2A:
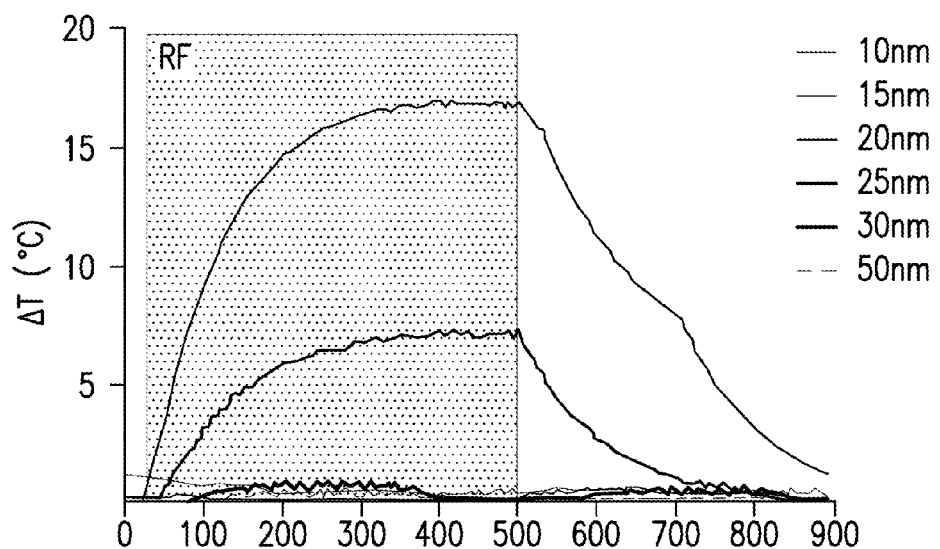
FIG. 2. Heating of iron oxide nanoparticles in RF magnetic field. (A) Bulk heating effects of treating iron oxide nanoparticle suspensions (1 mg/ml, 10-50 nm) in water with 465 kHz RF magnetic field. (B) TEM of Ocean Nanotech (SHP-20-50) iron oxide nanoparticles and their size distribution, calculated to be 19.83±2.7 from 450 particles. (C) X-ray photoelectron spectroscopy of iron oxide nanoparticle samples. Survey indicated the presence of iron, carbon, and oxygen with iron content investigated in upper inset and the presence of carboxyl groups confirmed in the lower inset. (D) XRD pattern of iron oxide nanoparticles compared with JCPDS patterns #39-1346 ($\gamma$-$Fe_2O_3$) and #75-0033 ($Fe_3O_4$). (E) Bulk heating effects of treating iron oxide nanoparticle suspensions (1 mg/ml, 10-30 nm) in water with 13.56 Mhz, 200 W, RF magnetic field.
Figure 2B:
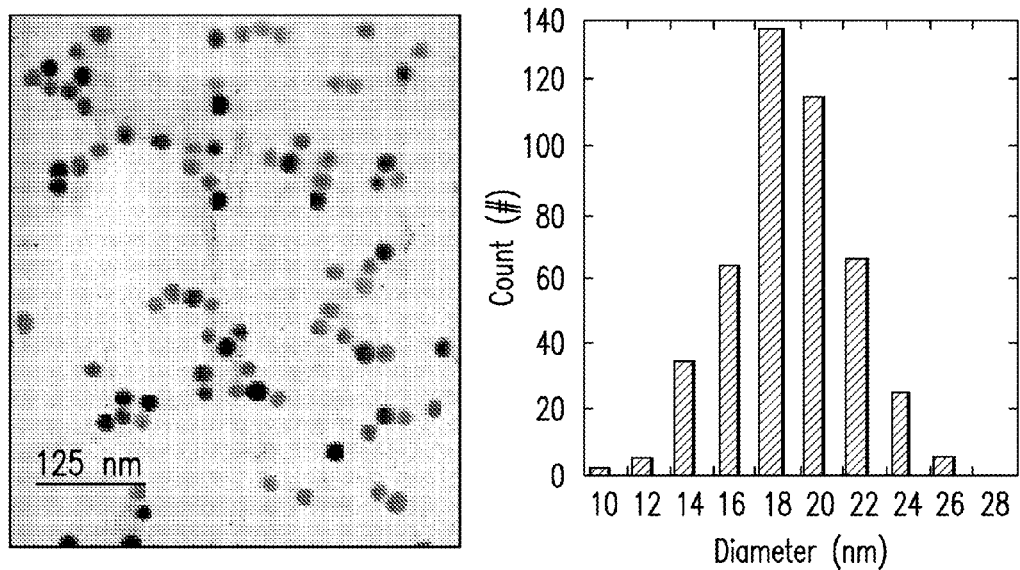
Figure 2C:
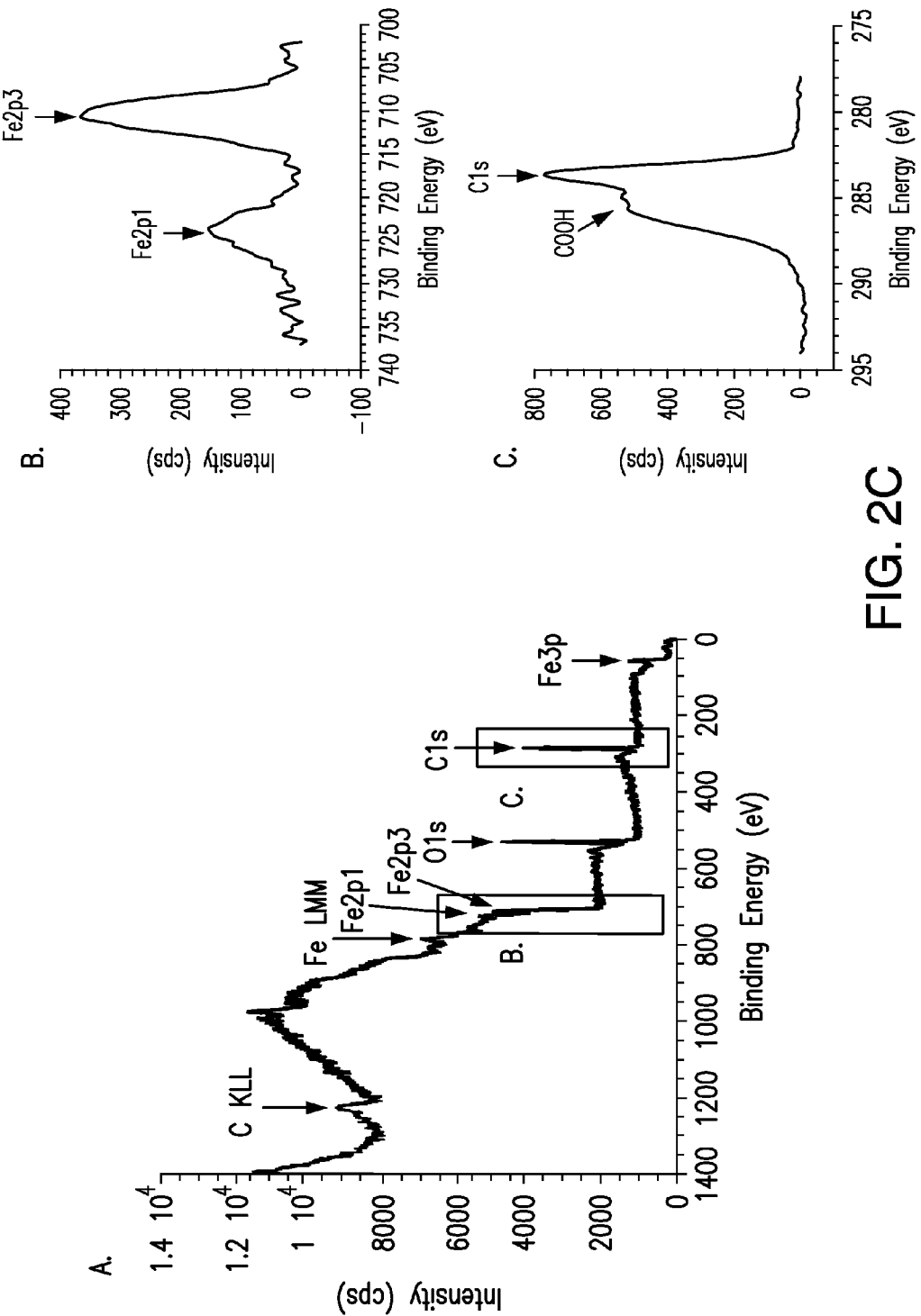
Figure 2E:
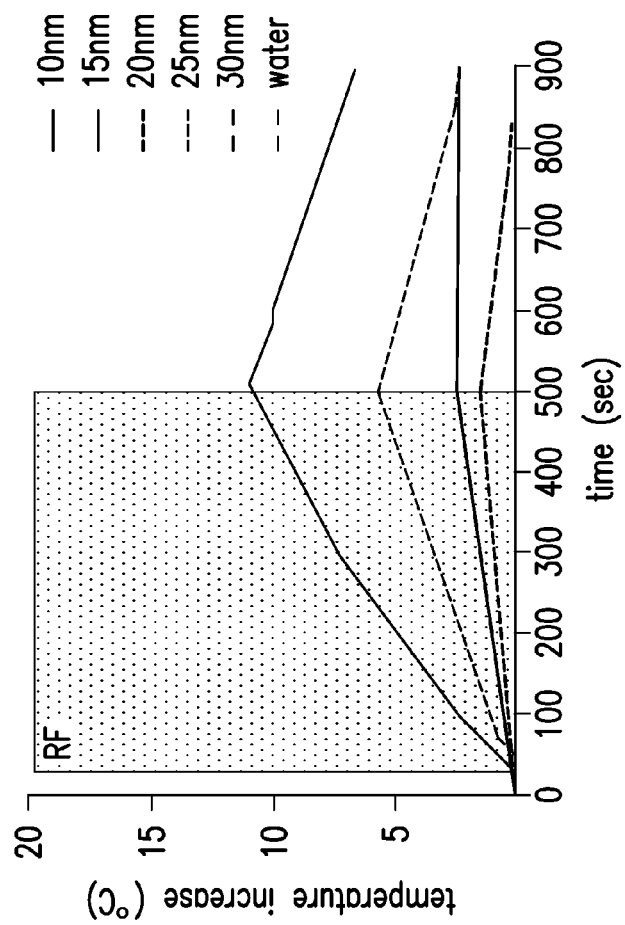
Figure 2D:
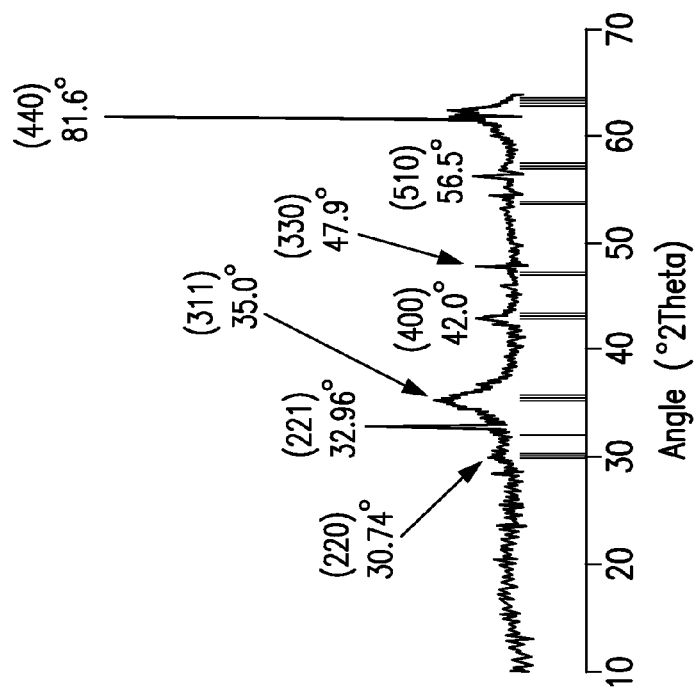

The present invention provides methods and compositions for the remote control of cell function based on the use of radiofrequency waves to excite nanoparticles targeted to specific cell types. The cell type of interest expresses a temperature sensitive channel wherein excitation of the nanoparticles results in a localized temperature increase that is transduced into a cellular response. Such cellular responses, include for example, modulation of cell proliferation, cell differentiation, apoptosis, and/or activation of signal transduction pathways. In a specific embodiment of the invention, the cellular response is an increase in gene expression resulting in production of one or more physiologically active proteins. The expression of such proteins may be used to treat various inherited or acquired disorders including for example, cardiovascular disorders, central nervous system disorders, autoimmune diseases, oncological diseases, hormonal disorders, metabolic diseases, blood disorders or immune disorders. Additionally, the proteins may be expressed to treat various infectious diseases including, for example, viral, bacterial, parasitic, and fungal infections. The cellular response resulting from nanoparticle excitation may also be designed to result in an increase in gene expression resulting in production of one or more nucleic acid molecules of interest. Such nucleic acid molecules include those molecules capable of regulating protein expression, such as antisense and siRNA molecules.

The expression system of the present invention can be used with virtually any type of biological cell population, including prokaryotic and eukaryotic cells. Such eukaryotic cells include, for example, plant and mammalian cells. The specific cell type used will typically vary depending upon the type of cellular response that is sought to be regulated. For example, mammalian cells and specifically, human cells or animal cells are typically preferred for increased expression of a physiological protein for use as a therapeutic.

In an embodiment of the invention the cell type of interest is a stem cell, preferably a mammalian stem cell. For example, stem cells engineered to express NICE constructs can act as autografts to enable external control of cell function. As used herein, "stem cell" refers to any cell having the potential to differentiate into one or more different cell types, including pluripotent stem cells. Such cells include, but are not limited to, stem cells derived from a variety of different sources including, for example, bone marrow, embryonic blastocysts or yolk sac, spleen, blood, including peripheral blood and umbilical cord blood, adipose tissue and other tissues and organs. Such stem cells include, but are not limited to, hematopoietic stem cells, mesenchymal stem cells, endothelial progenitor cells or embryonic stem cells.

In a specific embodiment of the invention, the cell type of interest expresses a temperature sensitive channel wherein activation of the nanoparticles results in a localized temperature increase that is transduced into a cellular response via the temperature sensitive channel. Such temperature sensitive channels include, but are not limited to, TRPV1 TRPV2, TRPV3, TRPM8, chimeric TRP channels, and tandem pore domain potassium channels, such as TREK1, TREK2, and TASK. The localized temperature increase mediated by the excitation of the nanoparticles leads to an activation of the TRPV1 channel resulting in gating of Ca2+ entry.

In a specific embodiment of the invention, the cell type of interest expresses a channel wherein activation of the nanoparticle results in motion of the nanoparticle that is transduced into a cellular response via the mechanical motion of the particle. Such motion sensitive channels include, but are not limited to, TREK-1, TRAAK, TRPV4, and TRPV1. The localized stimulation of nanoparticle motion leads to an activation of the channel resulting in modulation of cell activity.

In an embodiment of the invention, the cells to be targeted may be genetically engineered to express one or more genes encoding physiologically active proteins of interest, such as those proteins providing a therapeutic benefit. The cells are genetically engineered in such a way that expression of the protein(s) of interest is induced in the cell upon excitation of the nanoparticles which results in a localized temperature increase or an increase in nanoparticle motion. Alternatively, the cells to be targeted may be engineered to express a non-encoding nucleic acid molecule of interest such as an antisense or siRNA molecule. Additionally, the target cells maybe genetically engineered to express a temperature sensitive protein, such as a temperature sensitive ion channel, wherein an increase in temperature mediated by the excited nanoparticles results in a cellular response through activation of the ion channel.

In another embodiment of the invention, target cells may be engineered to intracellularly express a protein that is capable of acting as an activated nanoparticle upon exposure to a RF magnetic field. Such proteins include for example, the iron storage protein ferritin. Such proteins may be expressed in the cell as fusion proteins to target their location to a specific site within the cell, for example, in close proximity to a temperature sensitive channel.

In an embodiment of the invention, recombinant expression vectors designed to express a physiologically active protein of interest, or a nucleic acid molecule of interest, such as antisense or RNAi molecules, or a protein that may act as a natural nanoparticle can be introduced into the target cells of choice.

The recombinant expression vectors, in addition to containing a nucleic acid encoding the protein or nucleic acid of interest, will contain transcriptional regulatory sequences that can be induced upon excitation of the particles resulting in expression of the protein, or nucleic acid molecule of interest. Such transcriptional regulatory sequences, include, but are not limited to, promoter and/or enhancer sequences that induce gene expression in response to ion channel activation. Such regulatory sequences include, but are not limited to the calcium response elements, referred to herein as SRE, CRE and NFAT RE.

The cells may be genetically engineered using techniques well known in the art. Such techniques include, for example, in vitro recombinant DNA techniques, synthetic techniques, and in vivo genetic recombination. (See, for example, the techniques described in Sambrook J et al. 2000. Molecular Cloning: A Laboratory Manual (Third Edition), and Ausubel et al (1996) Current Protocols in Molecular Biology John Wiley and Sons Inc., USA). Any of the methods available in the art for gene delivery into a host cell can be used according to the present invention to deliver genes into the target cell population. Such methods include electroporation, lipofection, calcium phosphate mediated transfection, or viral infection. In a specific embodiment, a viral vector that contains a nucleic acid encoding the protein or nucleic acid of interest and a transcriptional regulatory sequence that can be induced upon excitation of the nanoparticles can be used. Such viral vectors include for example, retroviral, adenoviral or adeno-associated viral vectors. (See, Kozarsky and Wilson, 1993, Current Opinion in Genetics and Development 3:499-503 for a review of adenovirus-based gene delivery).

For general reviews of the methods of gene delivery see Strauss, M. and Barranger, J. A., 1997, Concepts in Gene Therapy, by Walter de Gruyter & Co., Berlin; Goldspiel et al., 1993, Clinical Pharmacy 12:488-505; Wu and Wu, 1991, Biotherapy 3:87-95; Tolstoshev, 1993, Ann. Rev. Pharmacol. Toxicol. 33:573-596; Mulligan, 1993, Science 260:926-932; and Morgan and Anderson, 1993, Ann. Rev. Biochem. 62:191-217; 1993, TIBTECH 11(5):155-215.

In order to access different organs non-invasively, it is necessary to have an electromagnetic field that is capable of passing through tissue as part of a system that allows some cells to be activated while the majority are not. Accordingly, radiofrequency (RF) electromagnetic fields are used for this purpose. RF signals at low and medium frequencies penetrate tissues freely and without significant energy absorption making it now possible to adapt this system for in vivo use (Jokela International Union of Radio Science 2008). In contrast to tissues, metallic/metal oxide nanoparticles placed in an alternating RF field absorb energy and heat in a controlled manner depending on the strength of the field, a process known as induction heating (Fortin et al., J. Am, Chem. Soc. 129:2628-2635). The heating capacity depends on nanoparticle composition, size, perhaps shape and the frequency and power of the RF field and, as such, it is possible to regulate the heat generated within the physiological temperature range.

In vitro, the temperature response achieved is fast and decays quickly (inverse of the square of the distance) thus providing a rapid, functional 'on-off' switch. The nanoparticles employed, for example, magnetic iron oxide and gold spheres, are easily prepared, have little or no intrinsic cell toxicity and can readily be adapted to target cells by incorporating streptavidin, antibodies, or pharmacological agents (Samanta B. et al. J Mater Chem 18:1204-1208; Wang A Z. et al. 2008 Expert Opin Biol Ther 8:1063-1070). Therefore, they are well suited for inducing localized temperature changes that can be transduced into cellular responses in vitro and in vivo.

Nanoparticles of differing compositions and shapes are heated at defined rates by different electromagnetic field frequencies and strengths. Nanoparticles for use in the present invention include, but are not limited to, metallic nanoparticles, and metal oxide nanoparticles. Such nanoparticles include, but are not limited to, iron oxide nanoparticles, gold nanoparticles, and the like. For example, iron oxide nanoparticles are maximally heated by an EM frequency of around 465 kHz while gold nanoparticles heat at an EM frequency of 13.5 MHz, with the field strength determining the rate of heating. This property potentially allows distinct EM frequencies to differentially heat nanoparticles of different compositions and/or shapes. Nanoparticles consisting of different chemistries, such as, but not limited to, gold and iron oxide, and of different shapes, particularly nanoparticles of different aspect ratios (e.g., spheres vs. rods), can be chosen based on their discrete heating frequencies and resistivities. The described invention provides non-limiting, illustrative compositions and methods encompassing different chemistries and spheres of specific sizes. The nanoparticles can be directed to distinct cell populations via cell-specific expression of unique tethers and then, using RF generators and tunable amplifiers with a range of excitation frequencies, excite different cell populations alone or in combination.

Further, the nanoparticles can be conjugated to various biological or chemical moieties that bind a specific receptor or target a specific cell type. In such instances, the nanoparticles may be externally applied to the cells. The ligand can comprise a small molecule, peptide, antibody, nucleic acid, protein, carbohydrate, lipid, polyethylene glycol derivatives or any combination thereof. Metal nanoparticles can readily be functionalized to target define cell populations by coating with specific antibodies that recognize proteins that are normally expressed on a cell or transfected into that cell (Samanta et al., J. Nat. Chem. 18:1204-1208; Wang et al., Expert. Opin. Biol. Ther. 8:1063-1070). For example, streptavidin, which binds to biotin with extremely high affinity, may be conjugated to nanoparticles. Through conjugation of strepavidin to nanoparticles, a system is provided whereby streptavidin-conjugated nanoparticles can be coupled to biotin-labeled cells through the strepavidin/biotin high-affinity reaction. Loading of nanoparticles onto the cells permits targeting of heat to said cells.

In addition to external application of nanoparticles to the target cell of interest, cells may be genetically engineered to express proteins which can act as naturally occurring nanoparticles and which can be activated by a RF magnetic field. Such proteins include, for example, the iron storage protein ferritin, the bacterial gene MagA, ceruloplasmin and transferrin.

The method of the present invention comprises contacting a target cell population with nanoparticles for a time sufficient to permit binding of the nanoparticle to the surface of the target cell. In an embodiment of the invention, the nanoparticles are administered in vivo to a subject resulting in contacting of a target cell population with nanoparticles for a time sufficient to permit binding of the nanoparticle to the surface of the target cell.

In an embodiment of the invention, the target cells are cultured, using routine tissue culture methods well known to those of skill in the art. Cells are then washed with a buffer, such as a phosphate-buffered saline (PBS) and a solution of nanoparticles is added to the target cells. In an embodiment of the invention, the nanoparticle solution comprises a mixture of the tissue culture media in which the cells are cultured and nanoparticles. Cells are incubated with the nanoparticles for a time sufficient to permit efficient binding of the nanoparticles to the target cells. Transfer of nanoparticles to the target cells can be monitored using, for example, flow cytometry.

In a preferred embodiment of the invention the target cell population are stem cells. Also within the scope of the invention are nanoparticle labeled cells that have been genetically engineered to express a desired protein, or nucleic acid of interest. For example, nanoparticle labeled cells may be engineered to express proteins capable of providing a therapeutic benefit.

The present invention further provides pharmaceutical compositions comprising nanoparticles, nanoparticle-labeled cells and/or cells that express nanoparticles intracellularly and a pharmaceutically acceptable carrier. Pharmaceutically acceptable carriers are well known to those skilled in the art and include, but are not limited to, 0.01-0.1M and preferably 0.05M phosphate buffer, phosphate-buffered saline (PBS), or 0.9% saline. Such carriers also include aqueous or non-aqueous solutions, suspensions, and emulsions. Aqueous carriers include water, alcoholic/aqueous solutions, emulsions or suspensions, saline and buffered media. Examples of non-aqueous solvents are propylene glycol, polyethylene glycol, vegetable oils such as olive oil, and injectable organic esters such as ethyl oleate.

Nanoparticle-labeled cells and/or cells that express nanoparticles intracellularly can also be incorporated or embedded within scaffolds which are recipient-compatible and which degrade into products which are not harmful to the recipient. These scaffolds provide support and protection for nanoparticle-labeled cells that are to be transplanted into the recipient subjects.

The present invention provides methods and compositions which may be used to provide a therapeutic benefit for treatment of various diseases. Specifically, through the use of nanoparticle-labeled cells and/or cells that express nanoparticles intracellularly, a therapeutic protein, or nucleic acid molecule of interest, may be delivered to a subject in need of treatment through administration of nanoparticle labeled cells. Alternatively, nanoparticles themselves may be administered to a subject in need of treatment, wherein said nanoparticles are targeted to endogenous cells of the subject wherein excitation of the nanoparticle results in a localized temperature increase that is transduced into a cellular response.

Various delivery systems are known and can be used to administer the nanoparticles, nanoparticle labeled cells and/or cells that express nanoparticles intracellularly. Such compositions may be formulated in any conventional manner using one or more physiologically acceptable carriers optionally comprising excipients and auxiliaries. Proper formulation is dependent upon the route of administration chosen.

The methods of the invention, comprise administration of nanoparticles and/or nanoparticle labeled cells and/or cells that intracellularly express a nanoparticle, in a pharmaceutically acceptable carrier, for treatment of various disorders or diseases. "Administering" shall mean delivering in a manner which is effected or performed using any of the various methods and delivery systems known to those skilled in the art. Administering can be performed, for example, pericardially, intracardially, subepicardially, transendocardially, via implant, via catheter, intracoronarily, intravenously, intramuscularly, subcutaneously, parenterally, topically, orally, transmucosally, transdermally, intradermally, intraperitoneally, intrathecally, intralymphatically, intralesionally, epidurally, or by in vivo electroporation. Administering can also be performed, for example, once, a plurality of times, and/or over one or more extended periods.

The term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. The composition can be formulated as a suppository, with traditional binders and carriers such as triglycerides. Oral formulation can include standard carvers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the therapeutic compound, preferably in purified form, together with a suitable amount of carrier so as to provide the form for proper administration to the patient. The formulation should suit the mode of administration.

The appropriate concentration of the compositions of the invention which will be effective in the treatment of a particular disorder or disease will depend on the nature of the disorder or disease, and can be determined by one of skill in the art using standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose response curves derived from in vitro or animal model test systems. Additionally, the administration of the compound could be combined with other known efficacious drugs if the in vitro and in vivo studies indicate a synergistic or additive therapeutic effect when administered in combination.

Additionally, the progress of the recipient receiving the treatment may be determined using assays that are designed to detect the physiologically active protein expressed by the nanoparticle targeted cells.

The present invention further relates to transgenic non-human animals that may be engineered to contain cells that respond to nanoparticle excitation in a desired fashion. For example the transgenic animals may be engineered to express cell surface receptors that act as binding partners for the nanoparticles. Said target cells may either naturally, or through genetic engineering, express a protein, or nucleic acid molecule of interest upon nanoparticle excitation. Alternatively, the transgenic animals may be engineered to intracellularly express a nanoparticle, such as for example a naturally occurring iron nanoparticle. Such transgenic animals provide in vivo model systems for studying normal physiological processes as well as disease processes. The transgenic animals of the invention may further be useful as in vivo model systems for use in identification and testing of novel therapeutic compounds of interest.

According to one aspect of the described invention, the method of the invention can be implemented as follows. First, expression of both a biotin acceptor protein (BAP) fused to the transmembrane domain of platelet derived growth factor receptor (PDGFR) as a tether for streptavidin coated nanoparticles, and TRPV1, a temperature sensitive cation channel can be expressed in specific cells using specific promoters. Second, cells are "decorated" by delivering streptavidin-coated iron oxide nanoparticles into the region where the BAP is expressed. The high affinity of streptavidin and biotin results in the cells being coated with the metallic/metal oxide nanoparticles. Studies in vitro have confirmed this to be the case. Third, the cultured cells, or an animal, are exposed to a RF field of defined strength at an intensity that will increase the local temperature of the nanoparticle decorated cells, activate the TRPV1 channel and thus triggering calcium influx.

In some embodiments, the system can be modified such that only one construct is used for both tethering of the nanoparticle and gating of Ca2+ entry. For example, the TRPV1 protein may be engineered as a fusion protein capable of direct tethering of the nanoparticle. In an embodiment of the invention, the TRPV1 protein may be engineered as a fusion protein containing any "tag" that does not interfere with the functioning of the channel. Such tags are well know to those of skill in the art. As described in detail below, the TRPV1 protein can be expressed as a fusion protein containing HIS tags. In such a case, the nanoparticles are coated with anti-HIS antibodies for targeting to the cell.

The present invention provides methods and compositions for studying the role of different cell types in a complex organism. The definitive test of cell function is to selectively turn on or off the activity of a single cell type in a living animal and examine the effect on physiological function. The present invention provides for the use of nanoparticles to activate defined cell populations remotely with radiowaves. According to another embodiment, ferrous oxide coated with streptavidin can be used to decorate cells, which express a biotin acceptor protein under the control of cell specific promoters. These same cells are engineered to also express TRPV1, a single component, temperature-sensitive ion channel that can detect small changes in temperature within the physiological range and by conformational change allow graded calcium entry. Exposing the metal coated cells to a defined electromagnetic field increases the local temperature and activates TRPV1 channels resulting in a Ca2+ current and cell activation. Data is provided below that confirms the efficacy of this method both in vivo and in vitro. The technology can be used to modulate functions such as hormone release and neural activity. A means is also provided for combinatorial activation of different cells using a modified TRPV1 and nanoparticles fabricated from other metals that can be excited at different wavelengths. This tool can be used, for example, to examine the roles of specific peripheral and CNS cell populations in energy metabolism.

The methods and compositions of the invention can be used to refine the methodology by decorating different cell types with distinct particles tuned to different wavelengths to activate ensembles of different cell populations in various combinations. Further, the ability of NICE to modify hormone release to regulate glucose metabolism in diabetic animals in vivo can be further refined. The methods and compositions can also be used for stimulation of action potentials in electrically excitable cells to modify behavior and can be used to study the role of specific hypothalamic populations in (NPY and POMC) control of appetite.

Example 1

Radio-Wave Regulation of Plasma Glucose in Mice

The present invention provides methods and compositions to remotely and selectively switch on the activity of a single cell in a living organism and examine the effects on physiological function using nanoparticle induced cell excitation (NICE). The technique targets temperature sensitive calcium channels (TRPV1) to defined cells. These cells are decorated with metal nanoparticles which are heated by an external radiofrequency field. This in turn opens the TRP channel to stimulate calcium influx. Calcium entry initiates downstream events such as depolarization (neurons), hormone release (endocrine cells) or gene expression.

The studies described herein demonstrate the efficacy of NICE at stimulating calcium influx, modulating hormone release and stimulating gene expression both in vivo and vitro.

Material and Methods

Nanoparticles.

Iron oxide nanoparticles (10-50 nm diameter), functionalized with a surface carboxylic acid group, were purchased from Ocean Nanotech (Springdale, Ark.). The nanoparticles were conjugated to either mouse monoclonal anti-His antibody (AbD Serotec, Raleigh, N.C.) or streptavidin (Jackson Immunoresearch Laboratories, West Grove, Pa.) using carbodiimide and N-hydroxysuccinimide activation technique as employed by magnetic nanocrystal conjugation kit (Ocean Nanotech). Heating studies were performed using 1 ml of a bulk solution (1 mg/ml) of nanoparticles dispersed in water placed in an eppendorf inside the solenoid and the temperature of the suspension was monitored using a fiber optic system (Luxtron, Lambda photometrics, Herts, UK).

RF Magnetic-Field.

A 465 kHz sinusoidal signal was provided by a signal generator and applied through an amplifier (both Ultraflex, Ronkonkoma, N.Y.) to a 2-turn solenoid coil with a radius of 2.5 cm to produce a magnetic field strength of 5 mT. Samples were placed within the solenoid. A 13.56 Mhz sinusoidal signal was provided by a signal generator (RF Instrumentation, PA) and applied through an amplifier (Comdel, Gloucester, MA) to a 2-turn solenoid coil with a radius of 2.5 cm).

Plasmids.

TRPV1 On pcDNA3.1) was a kind gift of Wolfgang Liedkte (Duke University, NC) and cloned into pEGFP-N1 (Clontech, Mountainview, Calif.). It was modified by PCR (Fast start PCR, Roche) to introduce Hisx6. Nuclear factor of activated t-cells (NFAT) response elements and minimal promoter were from pGL4.30[luc2P/NFAT-RE/Hygro (Promega, Madison, Wis.). Serum response element (SRE), cyclic AMP response element (CRE) and form modified human insulin sequences were synthesized by Integrated DNA technologies (Coralville, Iowa). The calcium dependent response elements—SRE, CRE and NFAT response elements were each used in triplicate. The use of these three response elements increased the likelihood that at least one such mechanism would be active with high sensitivity in all of the cell types that we engineered. They were also used to achieve high specificity since each of these elements is reported to respond only to repeated or sustained changes in intracellular calcium. BAPTM, the transmembrane domain of platelet derived growth factor receptor fused to an extracellular biotin acceptor protein, was a kind gift of Dr. B Tannous, Massachusetts General Hospital, MA). TRPV1$^{His}$ and calcium responsive form insulin were cloned into MSCV-hygro and MSCV-puro plasmids (Clontech,) respectively for retrovirus production using Phoenix packaging cells. Mouse ferritin heavy chain was obtained from ATTC (Manassas, Va.) in pCMV sport6 and mouse ferritin light chain 1 was obtained from Invitrogen (Carlsbad, Calif.) in pYX-Asc. These were cloned downstream of EF1alpha promoter in pCR2.1 with a flexible linker region to create ferritin light chain-linker-heavy chain fusion protein. The fidelity of PCR products was confirmed by DNA sequencing.

Cell Culture and In Vitro Studies.

Human embryonic kidney cells (HEK 293T) were cultured in Dulbecco's modified eagle medium with 10% fetal bovine serum (Gibco, Carlsbad, Calif.) at 37° C. and 5% $CO_2$. PC12 cells were cultured in RPMI medium 1640 with 10% horse serum and 5% fetal bovine serum (Gibco) at 37° C. and 5% $CO_2$. Phoenix ecotropic packaging cells (Stanford University) were grown in Dulbecco's modified eagle medium with 10% fetal bovine serum (Gibco) at 37° C. and 5% $CO_2$.

Stable cell lines were produced by retroviral infection of PC 12 cells using the Phoenix system. Briefly, Phoenix eco cells ($2\times10^6$ cells per 6-cm dish) were transfected with MSCV-puro or hygro plasmids as described above. After 24 hours, the medium was replaced and the cells placed at 32° C. Medium was aspirated after a further 24 h and spun to remove cell debris. The Phoenix cell supernatant was added to PC12 cells (plated at $1\times10^6$ cells per 6-cm dish) using a 1:2 dilution in RPMI medium/10% FBS with polybrene (4 µg/ml, Sigma-Aldrich, St Louis, Mo.). Cells were incubated at 32° C. for a further 24 h before replacing the medium with RPMI/10% FBS. Selection medium was added 48 h after infection.

Embryonic stem cells were electroporated with a calcium dependent human insulin plasmid and selected with puromycin for 3 weeks. Resistant cells were identified for insulin insertion by Southern blot analysis before electroporation with TRPV1His plasmid and selection with hygromycin for 3 weeks. Three double resistant clones were screen by quantitative PCR for expression of insulin and TRPV1 and by immunohistochemistry for expression of TRPV1 and His tag. The ES clone with high expression by qPCR and IHC was used for RF studies. Cells were plated onto gelatin coated 12 mm cover glass (without feeder cells) for 96 hrs before assessing RF dependent release of calcium dependent human insulin.

For immunocytochemistry and RF studies, cells were cultured on 12-mm cover glass (Fisher Scientific, Pittsburgh, Pa.) coated with collagen (BD biosciences, Bedford, Mass.) and poly-D-lysine (Millipore, Billerica, Mass.). For EM studies, cells were cultured in 3 cm dishes. Cells were transfected 24 h after plating using lipofectamine 2000 (Invitrogen, Carlsbad, Calif.). For temperature dependent studies, cells were plated in 24-well plates coated with collagen and poly-D-lysine and transfected 24 h later. Culture medium was replaced 18 h after transfection and holotransferrin (2 mg/ml, Sigma) was added to cells transfected with ferritin. Cells were studied 72 h after transfection.

Temperature dependent release of calcium dependent human insulin: 24 h prior to the study, cells were placed in serum free medium at 32° C. to ensure minimal activation of TRPV1 and calcium dependent pathways. On the day of study, cells were preincubated for 30 min in 500 µl phosphate buffered saline (PBS) before incubation in 250 µl of calcium imaging buffer (Caterina et al. 1997 Nature 389:816) at 32 or 44° C. for 1 h. At the end of 1 h, the supernatant was aspirated, spun to remove cell debris and frozen at −80° C. until assay. Studies were performed in quadruplicate on three occasions.

RF dependent release of calcium dependent human insulin: 24 h prior to the study, cells were placed in serum free medium at 32° C. to ensure minimal activation of TRPV1 and calcium dependent pathways. On the day of study, cells were preincubated for 30 min in 500 µl PBS or 500 µl of functionalized iron oxide nanoparticles (1 mg/ml) resuspended in PBS. Cells were washed three times in PBS before incubation in 300 µl of calcium imaging buffer at room temperature (control) or in a RF field at room temperature. The supernatant was removed at 15, 30, 45 or 60 min depending on the study, spun to remove cell debris and frozen at −80° C. until assay. For gene expression analysis, cells from the supernatant and cover glass were lysed and the lysate stored at 80° C. until RNA purification. For apoptosis studies, the cells were incubated with functionalized nanoparticles at 1, 2, 4 or 8 mg/ml before RF treatment and immunocytochemistry. For RF dependent time course from stable PC12 cells, cells were left in serum containing medium prior to treatment to more accurately replicate conditions in vivo before performing the studies as described above. Medium was removed for assay at 15 and 30 mins.

For studies examining the role of TRP channels in RF mediated proinsulin release, ruthenium red (100 µM) was added to the calcium imaging buffer. For studies to examine the role of calcineurin in the activation of calcium dependent insulin gene, Tacrolimus (100 nM, Tocris Bioscience, Minneapolis, Minn.) was added to the medium for 24 hours prior to RF treatment. To examine if the effects of RF heating on iron oxide nanoparticles were confined to decorated cells, 3-cm dishes of HEK 293T cells were transfected with either BAPTM or TRPV1 and calcium dependent human insulin. After 24 h, the two transfected cell populations were trypsinized and mixed to form a co-culture with adjacent cells expressing BAPTM and TRPV1/human insulin.

Calcium Imaging.

Transfected cells were washed three times in PBS then loaded with Fluo-4 3 µM (Invitrogen) in the presence of sulfinpyrazone 500 µM (Sigma) for 60 min at room temperature. Cells were washed again in PBS then incubated for 30 min either with functionalized nanoparticles with sulfinpyrazone or in sulfinpyrazone in PBS. Cells were washed and then imaged in calcium imaging buffer. Imaging was performed using a Deltavision personal DV imaging system (Applied Precision, Issawaq, Wash.) equipped with a custom-made ceramic lens. Cells were imaged before and during RF treatment or before and after treatment with 200 µM 2 aminoethoxydiphenyl borate (2-APB).

Immunocytochemistry, Immunohistochemistry and Electron Microscopy.

Immunocytochemistry (ICC) was used to detect and quantify apoptotic cells following RF field treatment. Two assays were employed, TUNEL assay visualized using Apoptag Fluorescein direct in situ apoptosis detection kit (Millipore) and ICC for activated caspase-3 (Promega). After RF treatment, cells were washed twice in PBS and then fixed for 15 min in 2% paraformaldehyde (Electron Microscopy Services, Hatfield, Pa.). Cells were then stained according to the manufacturers' protocols. Expression of NFAT1 was also examined using ICC. Control or RF treated transfected cells were washed and fixed as above then incubated in for 1 h in blocking buffer (3% BSA (Sigma) and 2% goat serum (Sigma) in PBS with 0.1% Triton-X (Sigma)). Following blocking cells were incubated in primary antibody, rabbit anti-NFAT1 (Cell signaling), 1:50, diluted in blocking buffer overnight at 4 degrees. Cells were then washed three times in PBS before incubation in secondary antibody (goat anti-rabbit 488 1:1000) diluted in blocking buffer for 1 h. The cells were then washed a further three times in PBS before inverting and mounting using Fluoromount with DAPI (Southern Biotech, Birmingham, Ala.).

ICC was also used to examine expression of ferritin fusion. Cells were washed twice with PBS, fixed and blocked as above. Cells were incubated in primary antibody, rabbit anti-ferritin light chain (Dako, Carpinteria, Calif.), 1:1000, diluted in blocking buffer for 1 h. Cells were washed three times in PBS before incubation in secondary antibody (goat anti-rabbit 488 1:1000) diluted in blocking buffer for 1 h. The cells were washed a further three times in PBS before inverting and mounting using Fluoromount (Southern Biotech, Birmingham, Ala.).

Immunohistochemistry (IHC) was used to confirm expression of TRPV1 and His and quantify apoptotic cells in tumors. Tumors were fixed in 10% formalin (Sigma) at 4° C. overnight then placed in 30% sucrose in PBS at 4° C. for a further 24 h. Tissue was embedded in OCT and frozen before 20 µm cryosections were cut and placed directly on glass slides. Slides were placed at 55° C. for 1 h then stored at −80° C. before staining Apoptag Fluorescein direct in situ apoptosis detection and IHC for activated caspase-3 were performed according to the manufacturers' instructions. Staining for TRPV1 and His was performed as follows. Slides were washed three times with PBS then incubated in blocking buffer for 2 h followed by overnight incubation at 4° C. with primary antibody diluted in blocking buffer (rabbit anti-TRPV1 1:500, mouse anti-His 1:1000 (Sigma)). Slides were washed 3-times in PBS and then incubated overnight at 4° C. with secondary antibody diluted in blocking buffer (goat anti-rabbit 488 and goat anti-mouse 594 both at 1:1000). Slides were washed 3-times in PBS before applying Fluoromount and a coverglass (Fisher Scientific).

Images were acquired using a Zeiss Axioplane microscope and captured digitally with separate band-pass filters using the multichannel module of the AxioVision Zeiss software. Additional images were acquired using confocal microscopy (LSM 510 laser scanning confocal microscope; Carl Zeiss MicroImaging, Inc.). Quantification of TUNEL and active caspase-3 immunostaining was performed by an investigator blinded to the treatment group.

Electron microscopy was used to quantify nanoparticle binding to the cell membrane and to image ferritin in transfected cells. Cells were fixed in 2% paraformaldehyde/2.5% glutaraldehyde/0.1M cacodylate buffer, pH 7.4, for 15 minutes before pelleting and further fixation for 1 h. Cells were then treated with 1% osmium tetroxide (1 h, on ice) and 0.5% uranyl acetate (1 h) before dehydration with graded ethanol and treatment with propylene oxide (2×15 min). The cells were infiltrated with 50% EPON epoxy resin (Miller-Stephenson, Sylmar, Calif.) and 50% propylene oxide overnight then 100% EPON (2×2 h) before curing at 60° C. for 2 days. Blocks were cut with a diamond knife on a Leica UltracutE (Buffalo Grove, Ill.) and ultra-thin (~70 nm) sections were collected on uncoated 200 mesh grids and stained with uranium and lead. Grids were viewed with a Tecnai SpiritBT Transmission Electron Microscope (FEI, Hillsboro, Oreg.) at 80 KV and pictures were taken with Gatan 895 ULTRASCAN Digital Camera (Pleasanton, Calif.).

ImmunoEM was used to confirm binding of nanoparticles to TRPV1. HEK 293T cells were seeded on Aclar (Ted Pella Inc, Redding, Calif.) in 24 well plates and transfected with TRPV1 His 24 hours later. 72 hours after transfection, cells were washed twice with PBS and incubated with anti-His coated iron oxide nanoparticles for 30 mins. Following two further PBS washes, cells were fixed in a fixative containing fresh 4.0% paraformaldehyde and 0.1 M sodium cacodylate buffer (pH 7.4) for overnight. Cells were processed for immunoelectron microscopy: after incubating with a blocking solution containing 3% BSA and 0.05% saponin in sodium cacodylate buffer for 20 min, the primary antibody was applied and incubated for overnight at 4° C.; in the following day, after extensive wash secondary antibody conjugated with nanogold (Nanoprobes, Inc. Yaphank, N.Y.) (1:50) was applied and incubated for 2 hours; subsequently, with series of wash, silver enhancement was conducted by using silver enhancement kit (Nanoprobes, Inc. Yaphank, N.Y.). Cells were re-fixed with 2.5% glutaraldehyde in the cacodylate buffer, lightly postfixed with 1% osmium tetra-oxide (10 min), dehydrated by a graded series of ethanol, infiltrated with EMBed812 resin and embedded in the same resin. Ultrathin sections were cut and examined in the electron microscope (100CX JEOL, Tokyo, Japan) with the digital imaging system (XR41-C, Advantage Microscopy Technology Corp, Danver, Mass.). Control experiment was done by following the same procedure except for the step of omitting primary antibody and applying the blocking solution, instead.

Animals and In Vivo Studies.

Male athymic NCr-nu/nu mice (NCI-Frederick, 6 weeks old), an outbred strain, were used and housed under controlled light conditions (12 h light/12 h dark) and temperature (22° C.), single-caged, and fed ad libitum on standard mouse chow. Animal care and experimental procedures were performed with the approval of the Animal Care and Use Committee of Rockefeller University (protocol 11421) under established guidelines.

To generate subcutaneous tumors, $5\times10^6$ PC12 cells stably expressing TRPV1$^{His}$ and calcium dependent human insulin or calcium dependent human insulin alone were resuspended in a 1:1 mixture of PBS and growth-factor reduced Matrigel (BD biosciences) and injected into the flank of anesthetized mice bilaterally. Radiofrequency studies were performed 4 weeks later. Blood glucose was monitored weekly. Mice were fasted overnight before all studies.

Study 1:

Mice with TRPV1$^{His}$/insulin xenografts (n=7) were anesthetized with inhaled isoflurane. PBS or iron oxide nanoparticles functionalized with anti-His antibody were injected into the tumor (5×10 µl). After 30 min, mice were treated with an RF magnetic field for 30 min by placing in a solenoid connected to the RF generator. Tail vein samples were taken at −30 and 0 min before RF magnetic field treatment and at 10, 20, 30, 45, 60, 90 and 120 min after the onset of RF treatment. Retro-orbital blood was taken using EDTA coated capillary tubes at −30 and 30 min for plasma insulin measurement. As the mice are outbred and had high inter-individual variability in blood glucose, the studies were performed with a crossover design with each mouse receiving first PBS and then one week later receiving nanoparticle injections. Nanoparticle injections could not be performed first because the particles remain within the tissue for prolonged periods (Giustini et al., 2011 Nanotechnology 22:345101).

Study 2:

Mice with TRPV1$^{His}$/insulin xenografts (n=6/group) were anesthetized and were randomized to receive either functionalized iron oxide nanoparticles or PBS. An identical treatment protocol to study 1 was used and intratumoral temperature and core body temperature were monitored using a fiber optic temperature monitoring system. Thermal imaging using FLIR infrared camera SC325 (North Billerica, Mass.) was performed on a subset of mice. After 120 min, the mice were sacrificed and the tumors removed. Each tumor was divided in two and one half snap frozen in liquid nitrogen for RNA extraction and the one half placed in 10% formalin for immunohistochemistry.

Study 3:

Mice injected with PC12 cells stably expressing calcium dependent human insulin (n=8) were used and study 1 repeated.

Study 4:

Mice injected with PC12 cells expressing calcium dependent human insulin were used (n=6/group) and study 2 repeated.

Study 5:

Mice injected with PC12 cells expressing TRPV1$^{His}$ and calcium dependent human insulin were used (n=6/group) and study 1 was repeated using nanoparticles which had not been conjugated to anti-His antibody.

Study 6:

Mice injected with PC12 cells expressing TRPV1$^{His}$ and calcium dependent human insulin were used (n=7/group). Study 1 was repeated with mice injected initially with PBS and treated with RF. Blood glucose and insulin were measured as described above. One week later, mice were injected with anti-His conjugated nanoparticles and treated with RF. Blood glucose was monitored as above. After a further week, mice received a second injection of anti-His conjugated nanoparticles, were treated with RF and blood glucose and insulin were measured.

Assays.

Proinsulin was measured in cell supernatants by ELISA (Alpco, Salem, N.H.) according to manufacturer's protocol. Blood glucose was determined using a Breeze 2 glucometer (Bayer; Leverkusen, Germany). Blood was spun for 10 min and plasma was collected. Plasma levels of human insulin, produced by xenografts, were determined in mouse plasma by human specific ELISA (Alpco).

Real-Time PCR.

Total RNA was isolated by homogenizing tissue in TRIzol reagent (Invitrogen) or cells in buffer RLT and purifying the RNA using QIAGEN RNA prep kit. Complimentary DNA was synthesized using QIAGEN omniscript RT kit. Real-time PCR was performed using the TaqMan system (Applied Biosystems; Foster City, Calif.) according to the manufacturer's protocol.

Statistics.

All data were analyzed for statistical significance using the Student's t test. P values are as indicated.

Nanoparticle Characterization.

Figure 3A:
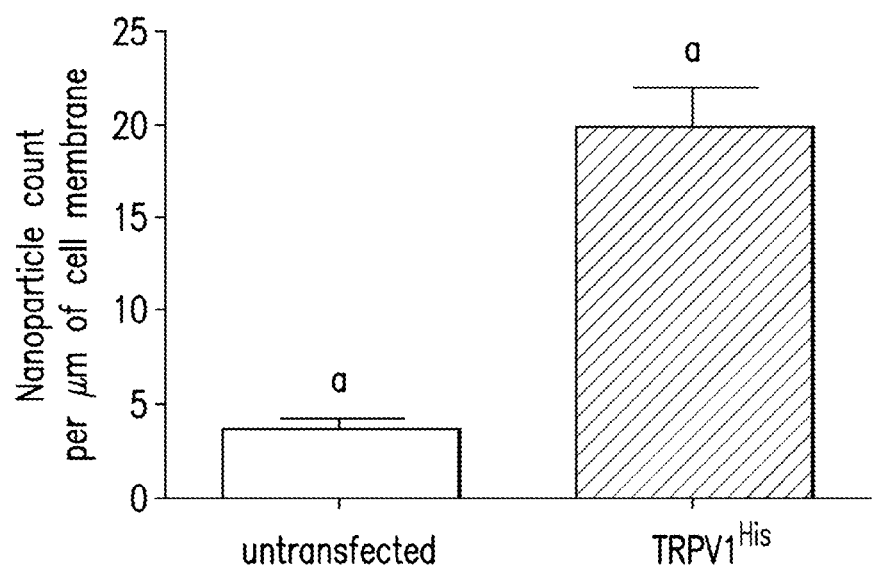
FIG. 3. Nanoparticle decoration of cells in vitro. (A) Nanoparticle decoration of cells in vitro. Significant nanoparticle binding to the surface of HEK293T cells expressing His tagged TRPV1 compared to untransfected cells. (B) Electron micrograph of anti-His antibody coated iron oxide nanoparticles (20 nm) binding to untransfected HEK293T cells (left panel) and HEK293 cells transfected with TRPV1$^{His}$ (right panel). Scale bar 200 nm. (C) Immunoelectron micrography of anti-His antibody coated iron oxided nanoparticles (20 nm) co-localized with silver enhanced gold immunostaining for TRPV1 (10 nm particles) in transfected HEK 293T cells (left panel). There is no TRPV1 immunostaining in the absence of the primary antibody (right panel). Scale bar as indicated. (D) Representative changes in Fluo-4 fluorescence after application of TRP agonist 2APB or RF treatment in HEK 293T cells transfected with TRPV1$^{His}$ and decorated with nanoparticles.
Figure 3B:
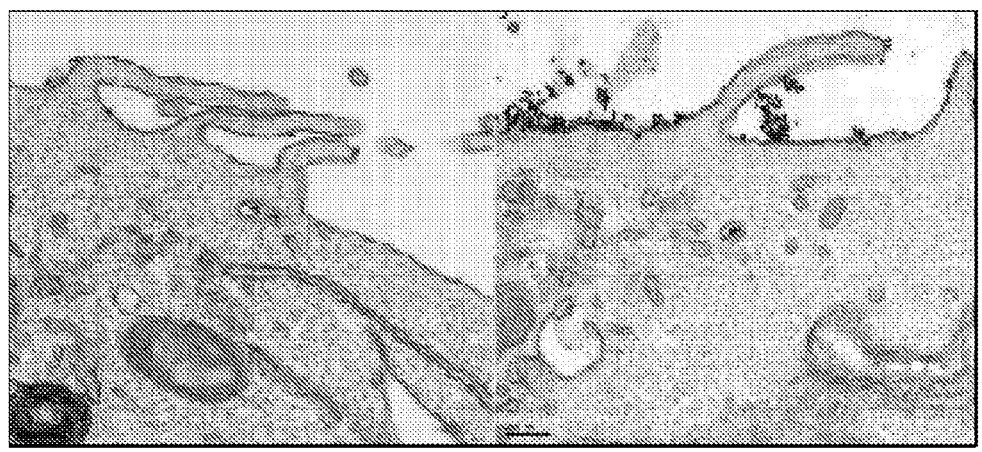
Figure 3C:
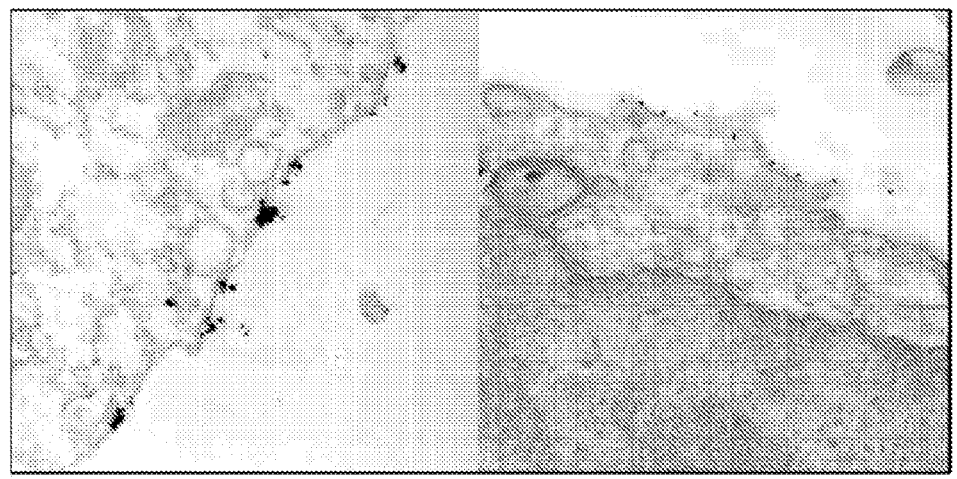
Figure 3D:
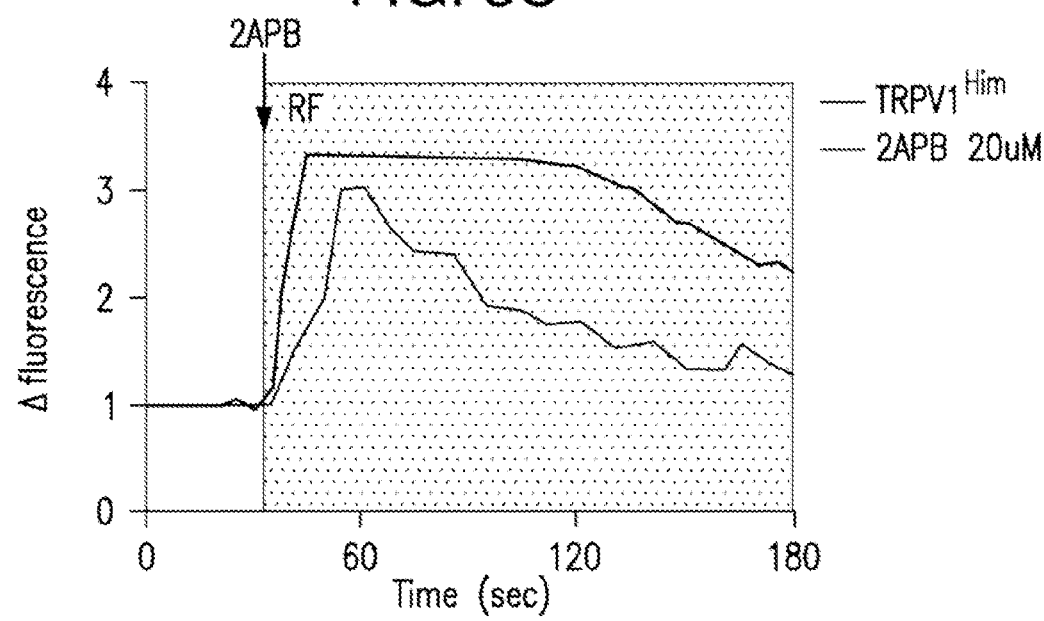

Iron oxide nanoparticles purchased from Ocean Nanotech (Catalog # SHP-20-50) were further characterized. The particles were coated with oleic acid and a proprietary polymeric coating, which is carboxy-terminated for further functionalization. The particles were specified to be 20 nm in diameter with a standard deviation of <5%. This was confirmed in the current work; TEM analysis of the size distribution yielded an average diameter of 19.8±2.7 nm (FIG. 3B). The particles were estimated to have a 4 nm oleic acid/polymeric coating in addition to the nanoparticle diameter observed in TEM. X-ray photoelectron spectroscopy (XPS) allowed identification of all elements within ~5 nm of the nanoparticle surface, as well as a more precise investigation of the nanoparticle surface chemistry and iron oxide content. XPS characterization (FIG. 3C) of the IONP indicated only the presence of iron, oxygen and carbon as would be expected from the polymeric coating. The shoulder in the C1s peak is consistent with the presence of carboxyl groups, as indicated in FIG. 3D. Moreover, the structure of the iron oxide particles was indicated by Ocean Nanotech to be magnetite ($Fe_3O_4$) for this particle size. However, magnetite and maghemite ($\gamma$-$Fe_2O_3$) is difficult to distinguish using x-ray diffraction (XRD) due to similarities in crystal structure. Indeed, comparison with JCPDS files #39-1346 (maghemite) and #75-0033 (magnetite) indicates that the current iron oxide particles are likely a mixture of both crystallographic structures.

Studies were also performed to extend the analysis of the heating characteristics of the nanoparticles at different frequencies. A limited number of frequencies are suitable for medical use in addition to the 465 kHz used previously. The heating of particles using a frequency of 13.56 Mhz which is the lowest of the remaining available frequencies and therefore the least likely to result in non-specific adsorption was also tested. The power level chosen was the maximum level that did not result in significant heating of water (200 W) in the absence of nanoparticles. At 465 kHz, observed a rapid increase in temperature for a suspension of 20 nm iron oxide nanoparticles with a temperature increase of 17° C. that reached a plateau at 300 s. A smaller rise in temperature (6° C.) was seen with 25 nm particles with only minimal heating for larger sizes of iron oxide nanoparticle. In contrast, at 13.56 MHz, there was significant heating for a broader range of particle sizes (10-25 nm) with greatest heating observed for 15 nm particles (11° C.) and very little heating of 20 nm particles, with only a maximum temperature rise of 2° C. However, the heating rate for 15 nm particles was lower than that for 20 nm particles at 465 kHz and did not plateau over the test period. The heating of 25 nm particles was similar at both frequencies.

Nanoparticle Heating.

Temperature decay from the iron oxide nanoparticle (IONP) surface has been explored (Rast and Harrison, 2010 Nanotech Conference and Expo 2010, Anaheim, Calif., June 21-24, p. 910-914; Hergt et al., 2010 IEEE Trans. Mag. 34:3745; Wilson O. et al., 2002 Phys. Rev. B 66:224301; Jordan et al., 1993 Int. J. Hyperthermia 25:499) and is complicated by factors such as the heat capacity of the surrounding medium, the nanoparticle ligand coating, and diffusion away from the nanoparticle surface. The change in temperature in the vicinity of the nanoparticle decreases as the inverse of the radius, and may be approximated by the conductive heat transfer equation (Fourier's Law)(Rabin, 2002 Int. J. Hyperthermia 18:194):

$$\Delta T = \frac{V_{np}Q}{4\pi k}\frac{1}{r} = \frac{q\rho D^2}{12k}$$

where $V_{np}$ is the nanoparticle volume, Q is the total dissipated heat, r is the nanoparticle radius, q is the heating rate (W $g^{-1}$), $\rho$ is the nanoparticle density, D is the diameter of the heated volume, and k is the thermal conductivity of water (0.64 W $m^{-1 \circ}$ $C.^{-1}$). Though it has been calculated that heating sufficient to trigger channel activation cannot be achieved on the single nanoparticle scale ($\Delta T \sim 10^{-5 \circ}$ C./particle), it has been shown that accumulating a significant number of iron oxide nanoparticles in a small volume may raise the temperature sufficiently to have an effect. In a separate study, thermoresponsive polymer coatings on iron oxide nanoparticles have demonstrated increased drug release in radiofrequency fields, indicating that heating at the nanoparticle surface affected the structure of the thermopolymer and drug release profile. Both calculations and experiments in the literature have confirmed that ~1.2 mg of IONP are required to raise the temperature of a 1 $cm^3$ region by 5° C. (Derfus et al., 2007 Adv. Mater. 19:3932). Based on this published literature and assuming a cell volume of $9.05 \times 10^{-10}$ ml, we would require $1.1 \times 10^{-9}$ mg/cell (ie 1.1 pg/cell) to give a nanoparticle density of 1.2 mg/ml to cause a local 5° C. increase in temperature. From EM images, we observe an average of $2 \times 10^5$ nanoparticles/cm. Assuming the particles are evenly distributed, this would give $4 \times 10^{10}$ nanoparticles/cm$^2$. For a 20 µm cell, the surface area is $1.25 \times 10^{-5}$ cm$^2$ (assuming a sphere) and therefore the calculated number of nanoparticles decorating the cell is $5 \times 10^5$ nanoparticles. The density of Fe$_3$O$_4$ is 5.24 g/cm$^3$, and each nanoparticle is 20 nm in diameter, giving a nanoparticle weight of $1.75 \times 10^{-16}$ g. Therefore, to achieve 1.1 picograms of nanoparticles per cell one would need at least $6.26 \times 10^3$ nanoparticles. Thus it is calculated that an almost 100 fold greater nanoparticle decoration than that required to achieve a 5° C. local increase in temperature has been obtained.

Results

A system has been developed that allows remote activation of protein production by engineered cells in vitro and in vivo. The method (Figure. 1) uses iron oxide nanoparticles (FeNPs) that are coated with antibodies against His (anti-His) and that bind a modified TRPV1 channel with an extracellular His×6 epitope tag (TRPV1$^{His}$). As disclosed herein RF treatment, local heating of bound anti-His FeNPs activates the temperature-sensitive TRPV1, resulting in a calcium current to activate a Ca$^{2+}$-sensitive promoter placed upstream of a modified human insulin reporter gene.

Figure 4:
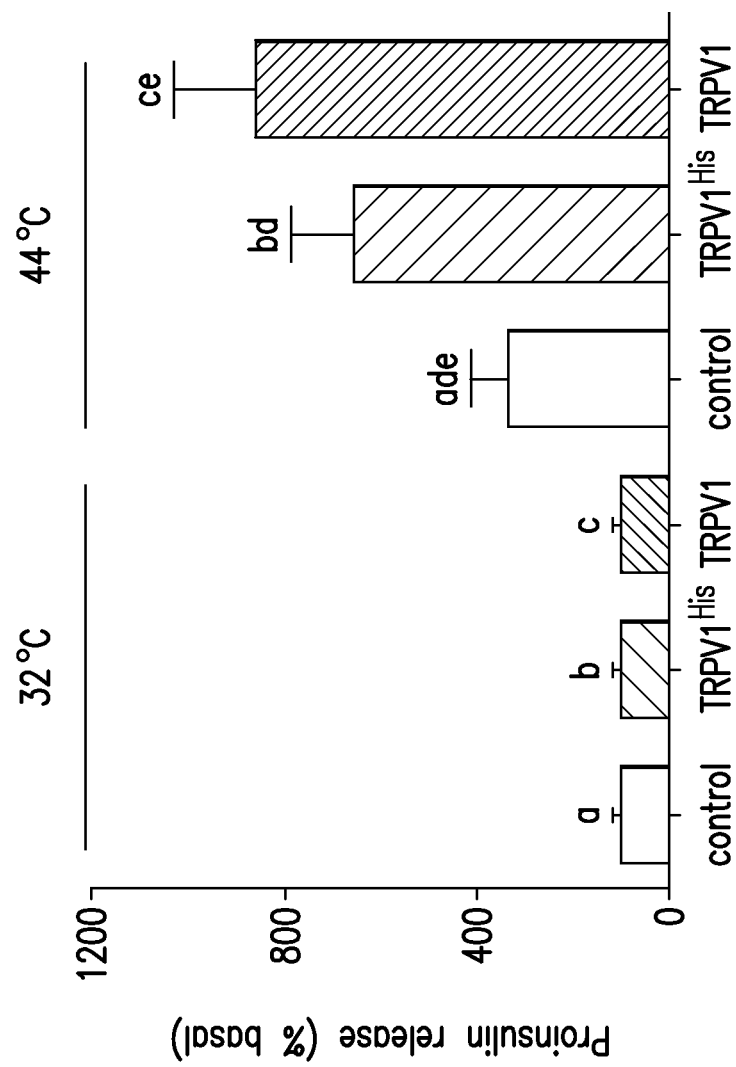
FIG. 4. Temperature dependent release of proinsulin. Proinsulin release from HEK 293T cells transfected with calcium dependent insulin alone, TRPV1$^{His}$ and calcium dependent insulin or TRPV1 and calcium dependent insulin was examined at 32° C., below the threshold for TRPV1 activation and at 44° C., above the threshold for TRPV1 activation. Expression of TRPV1$^{His}$ and TRPV1 significantly increased proinsulin release at 44° C. compared to that from cells without TRPV1. There is no significant difference in the proinsulin release seen with TRPV1$^{His}$ compared to unmodified TRPV1. (Same letter indicates p<0.05).

FeNPs was used for the following reasons: They heat at 465 kHz, a relatively low frequency that minimizes tissue heating; particles of 20 nM or less diffuse in the extracellular space (Wang et al., 2008 Expert Opin. Biol. Ther. 8:1063; Deflaco et al. 2001 Science 291:2608; Thorne et al., 2006 Proc. Natl. Acd. Sci USA 103:5567); and these particles can be derivatized with antibodies. At 465 kHz (5 mT), substantial heating was observed for 20- and 25-nm FeNP suspensions (FIG. 2). A 20-nm FeNP suspension had an initial heating rate of 0.15° C./s and a specific absorption rate (SAR) of 0.63 W/g, whereas the SAR of water at this field frequency and strength was less than 0.004 W/g. As shown by electron microscopy, a His-tag insertion into the first extracellular loop of TRPV1 provided a site for significant and specific FeNP binding (FIG. 3) with direct heat transfer to the adjacent channel (FIG. 4). Human embryonic kidney (HEK) 293T cells expressing TRPV1$^{His}$ and decorated with 20 nM FeNPs conjugated to anti-His showed a significant increase in intracellular Ca$^{2+}$ after 10 s of RF exposure (FIG. 3D).

Calcium entry was next used to induce gene expression via a novel synthetic 5' regulatory region composed of three Ca$^{2+}$ response elements in cis: serum response element (SRE), cyclic adenosine monophosphate response element (CRE), and nuclear factor of activated T cell response element (NFAT RE) (Hardingham et al. 1999 Microsc. Res. Tech. 46:348; Rao 2009 Nat. Immunol. 10:3) with a minimal promoter. This was placed upstream of a modified human proinsulin gene with furin cleavage sites replacing beta-cell-specific convertase cleavage sites to allow insulin processing in non-beta cells (Shirin et al., 2001 Gene Ther. 8:1480) (FIG. 5A).

Figure 5G:
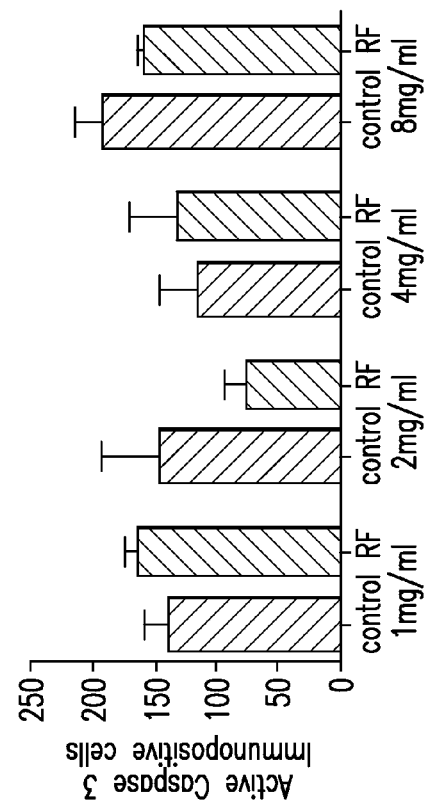
FIG. 5. (A) Bioengineered human insulin construct. Calcium dependent insulin release is via three calcium response elements: serum response element (SRE), cyclic AMP response element (CRE) and nuclear factor of activated T-cell response element (NFAT RE) and a minimal promoter upstream of a furin sensitive human insulin cDNA. (B) RF treatment does not change proinsulin release from cells expressing the calcium dependent insulin gene from cells with TRPV1$^{His}$, calcium dependent human insulin and nanoparticles in the absence of RF treatment, from cells expressing TRPV1 and calcium dependent human insulin treated with RF but in the absence of nanoparticles, or from cells treated with RF expressing calcium dependent human insulin and binding nanoparticles via a nanoparticle tether comprised of a platelet derived growth factor receptor transmembrane domain with fused extracellular biotin acceptor [protein but in the absence of TRPV1. (C) The effects of nanoparticle heating are cell specific. Cells transfected with a nanoparticle tether, BAPTM, and mixed with cells transfected with TRPV1 and calcium sependent human insulin show no increase in proinsulin release with RF treatment. (D) Translocation of NFAT1 with RF treatment. HEK cells transfected with TRPV1$^{His}$/calcium dependent human insulin incubated with anti-His iron oxide nanoparticles show almost exclusively cytoplasmic NFAT immunostaining without RF treatment (control, upper panels). RF treatment results in NFAT staining in both the cytoplasm and nucleus of the cells (RF, lower panels). (E) Effect of calcineurin inhibitor on RF dependent proinsulin release. Proinsulin release from RF treated HEK cells transfected with TRPV1$^{His}$/calcium dependent human insulin incubated with anti-His oxide nanoparticles was blocked by preincubation with Tacrolimus (100 nM). There is no difference apoptotic cells incubated with increasing concentrations of nanoparticles as assessed by TUNEL count (F) are activated Caspase-3 count (G) between untreated and RF treated cells is transfected with TRPV1$^{His}$.
Figure 5F:
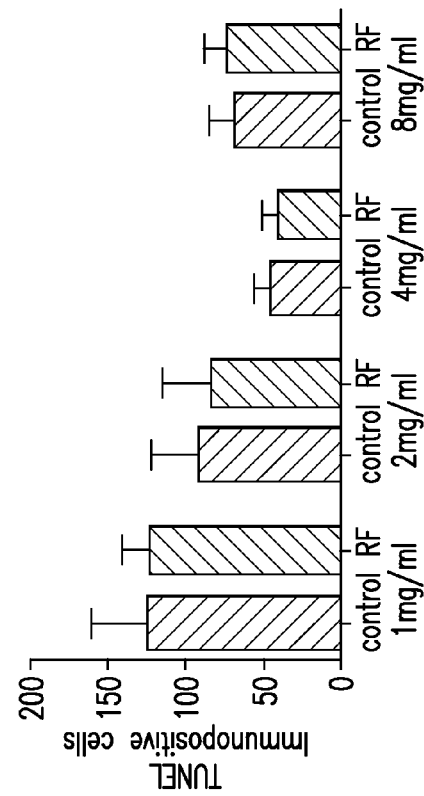
Figure 6A:
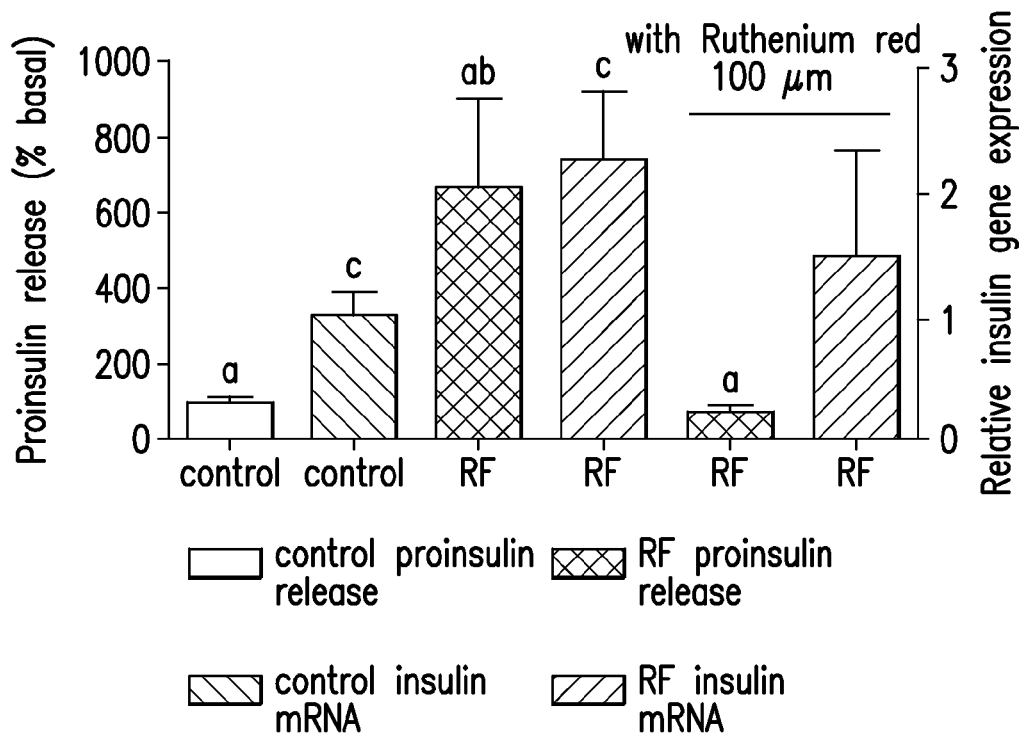
FIG. 6. (A) RF treatment increases proinsulin release and insulin gene expression in vitro. Nanoparticle-decorated HEK293T cells transfected with TRPV1$^{His}$ and calcium-dependent insulin show a significant increase in proinsulin release and insulin gene expression with RF treatment that is blocked by the TRP antagonist ruthenium red. (Columns marked with the same letter indicate significance, P<0.05. Error bars indicate SEM) (B) Time sources of proinsulin release and insulin gene expression from nanoparticle-decorated HEK293T cells transfected with TRPV1$^{His}$ and calcium-dependent insulin with RF treatment.
Figure 6B:
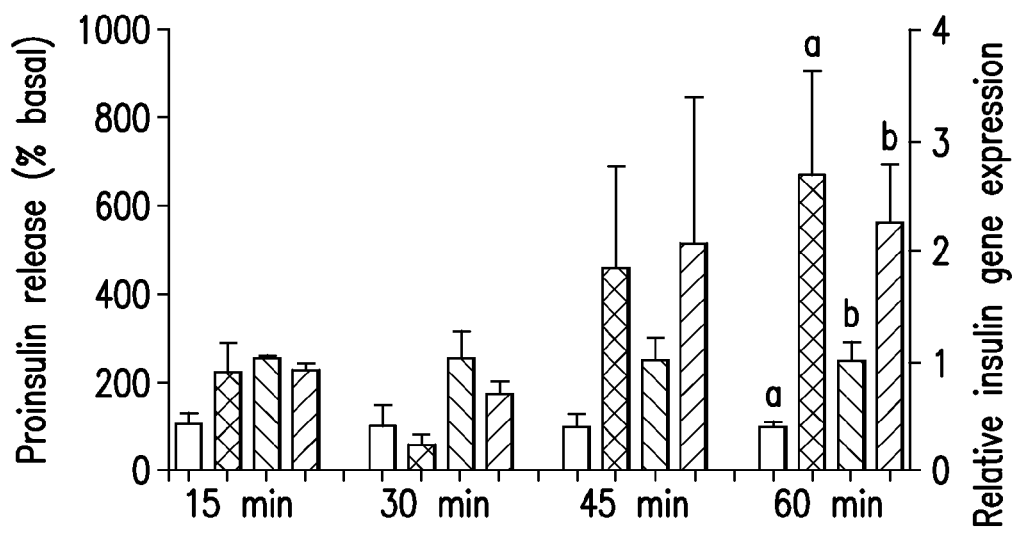
Figure 7A:
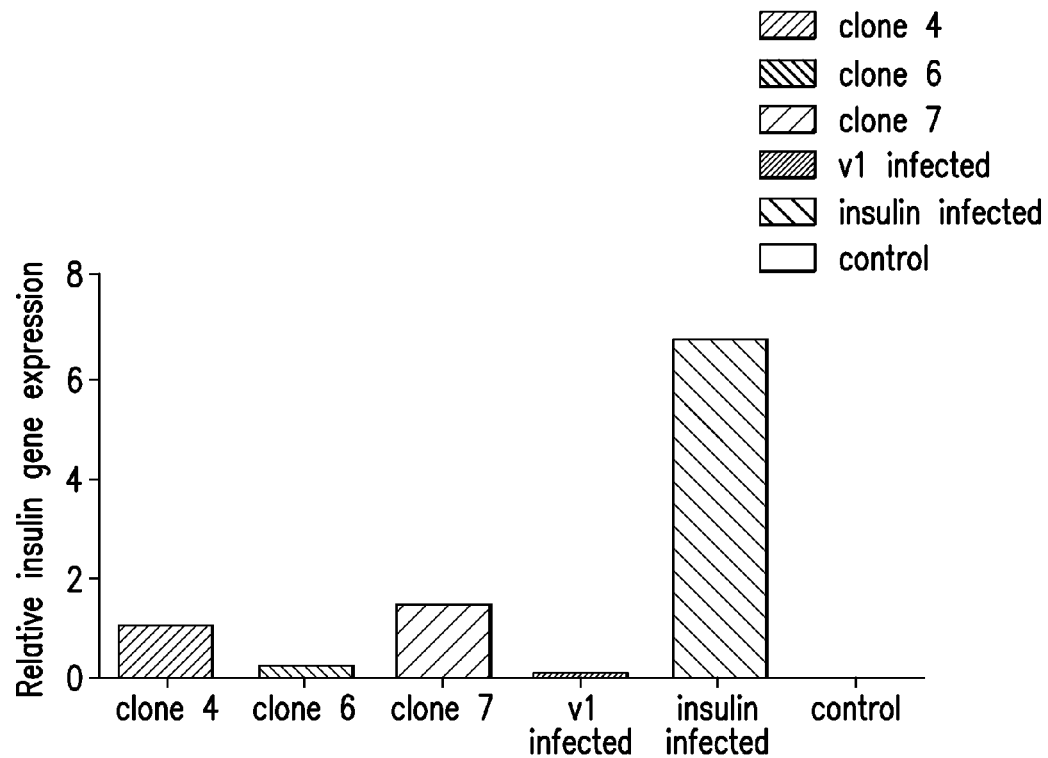
FIG. 7 Expression of constructs and RF dependent proinsulin release from ES cells. (A) Expression of insulin in ES cell clones: Quantitative PCR measured expression of human insulin in 3 ES cell clones (4, 6 and 7) electroporated with TRPV1$^{His}$ and Ca$^{2+}$-dependent human insulin construct along with cells stably expressing TRPV1 alone, Ca$^{2+}$-dependent human insulin construct alone or wild-type ES cells. (B) Expression of TRPV1 in ES cell clones: Quantitative PCR measured expression of TRPV1 in 3 ES cell clones (4, 6 and 7) electroporated with TRPV1$^{His}$ and Ca$^{2+}$-dependent human insulin construct along with cells stably expressing TRPV1 alone, Ca$^{2+}$-dependent human insulin construct alone or wild-type ES cells. (C) Immunohistochemistry for TRPV1 (upper panels) or His (lower panels) in wild-type cells (left panels), cells stably expressing TRPV1$^{His}$ (middle panels) or ES clone 7 (right panels). (D) RF dependent pro insulin release from ES cells. ES clone 7 expressing TRPV1$^{His}$ and Ca$^{2+}$-dependent human insulin incubated with iron oxide nanoparticles show a significant increase in proinsulin release in response to RF treatment (same letter indicates p<0.05).
Figure 7B:
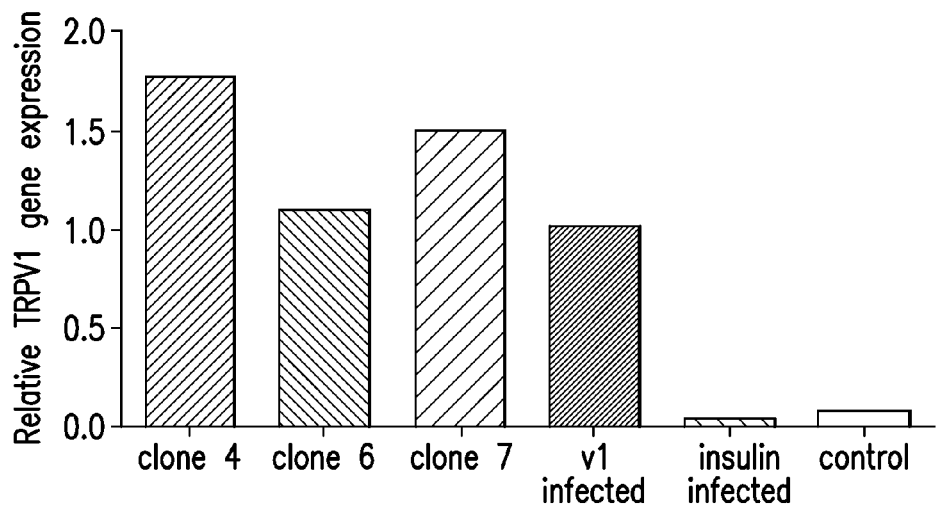
Figure 7D:
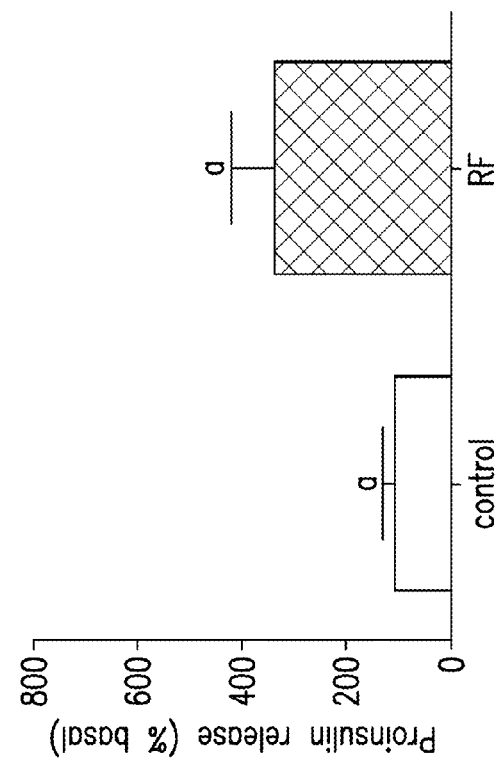
Figure 7C:
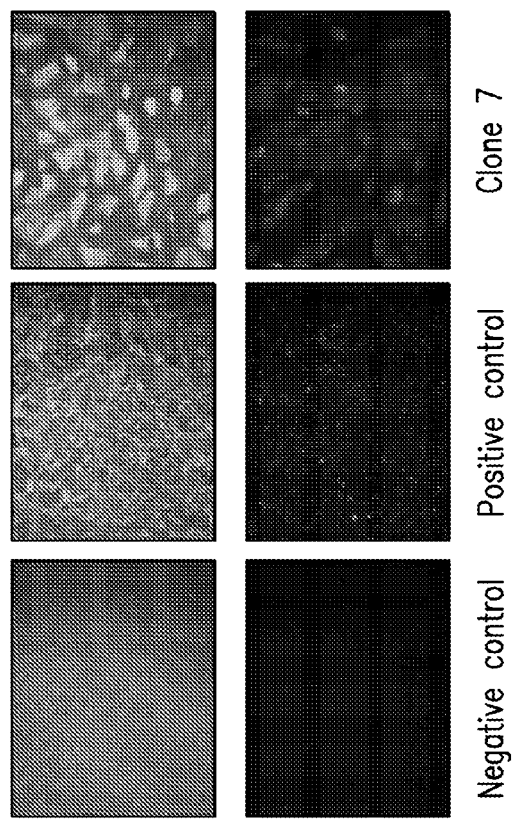
Figure 8C:
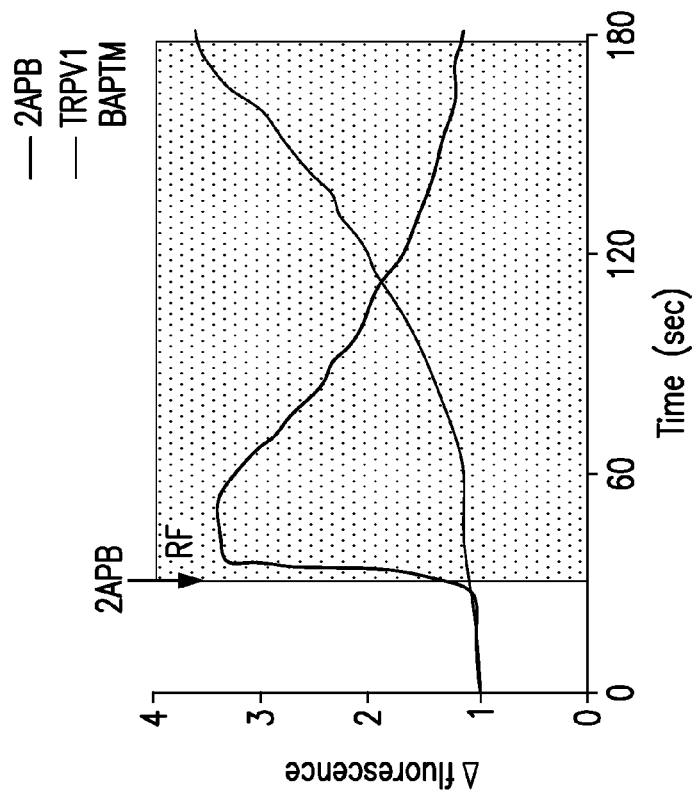
FIG. 8. depicts dual component system for cell activation. (A) Schema of dual component system. Streptavidin coated iron oxide nanoparticles bind biotin on a cell surface biotin acceptor protein fused to a transmembrane domain (BAPTM). Exposure to an RF field induces local heating, which opens TRPV1 channels. Calcium entry triggers downstream processes as before. (B) Nanoparticle binding to the surface of HEK 293 T cells expressing TRPV1 and BAPTM is increased compared to untransfected cells (p=0.09). (C) Representative changes in Fluo-4 fluorescence after application of TRP agonist 2APB or RF treatment in nanoparticle decorated HEK 293 T cells transfected with dual component system. (D) RF treatment increases proinsulin release in vitro from HEK 293T cells transfected with TRPV1, BAPTM and calcium dependent human insulin. This is blocked by Ruthenium red. (Same letter indicates p<0.05). (E) RF treatment increases insulin gene expression in vitro in cells with TRPV1, BAPTM and calcium dependent human insulin and is blocked by Ruthenium red. (F) Time course of proinsulin release with RF treatment from HEK293T cells transfected with TRPV1, BAPTM and calcium dependent human insulin. (G) Time course of insulin gene expression with RF treatment in cells transfected with TRPV1, BAPTM and calcium dependent human insulin.
Figure 8B:
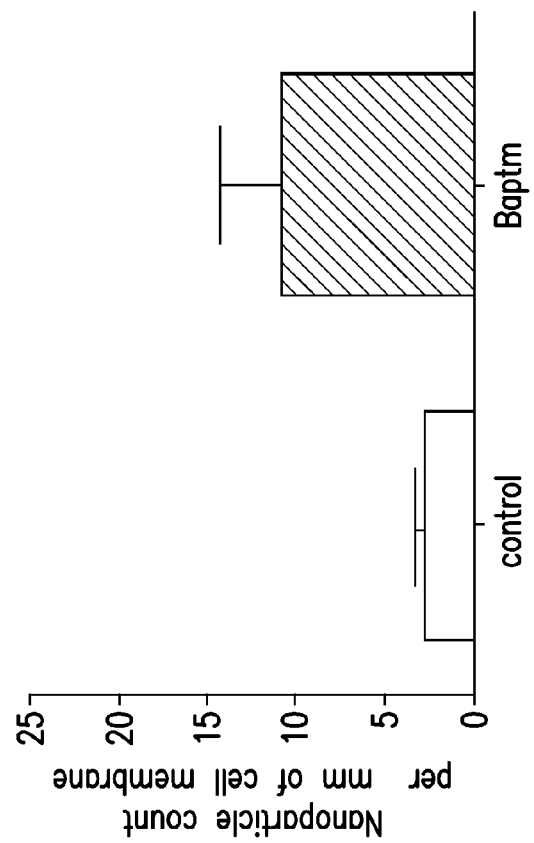
Figure 8E:
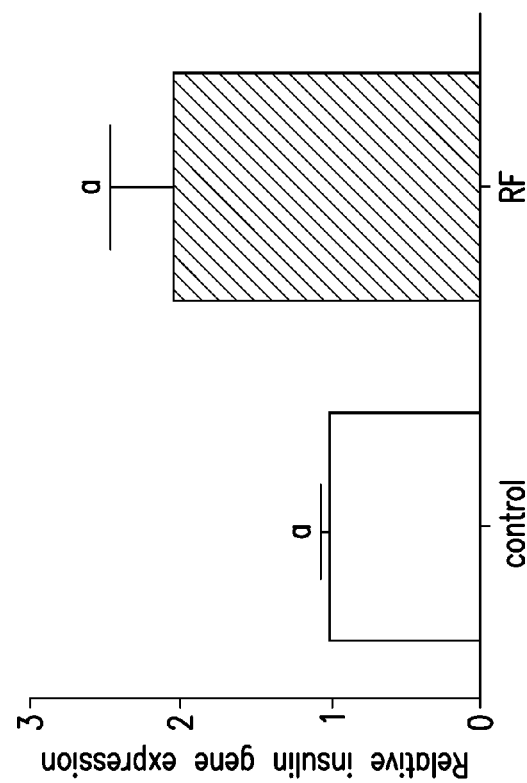
Figure 8D:
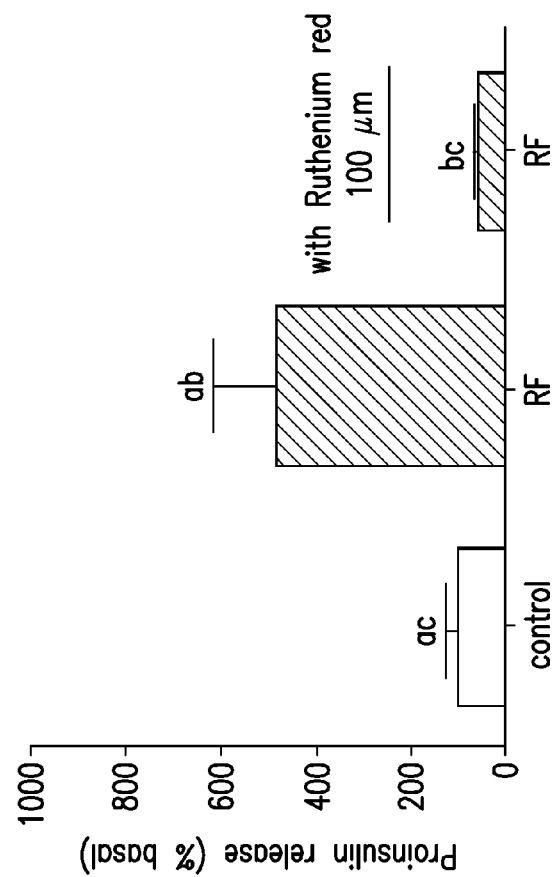
Figure 8G:
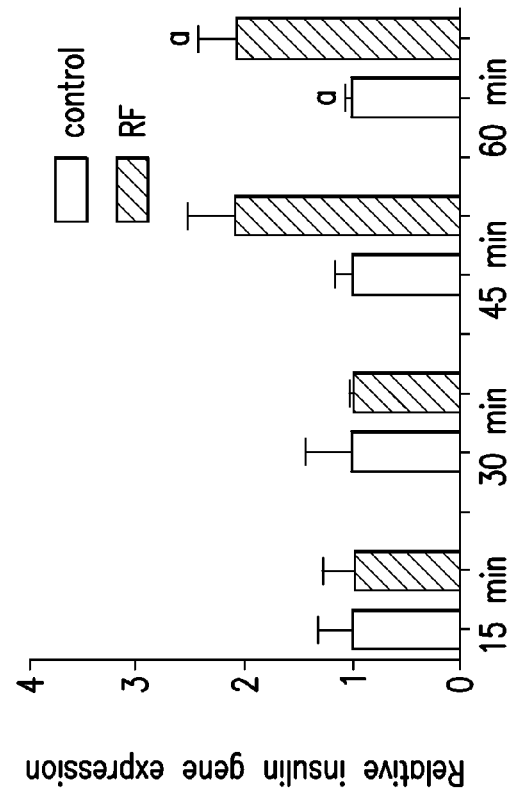
Figure 8F:
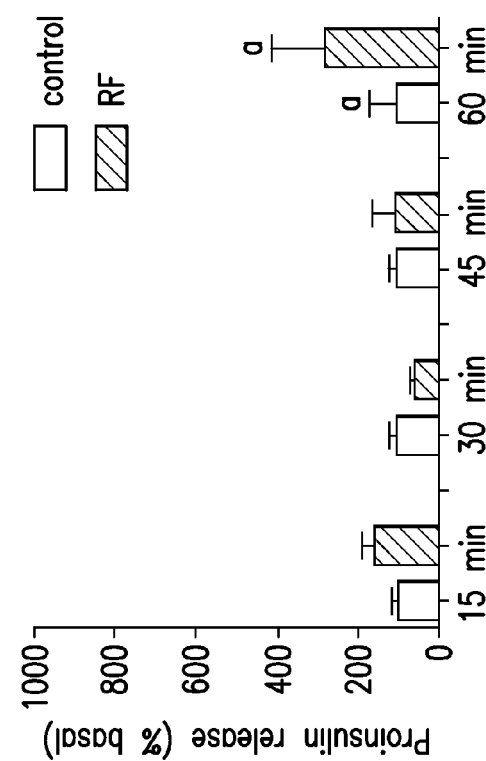
Figure 9F:
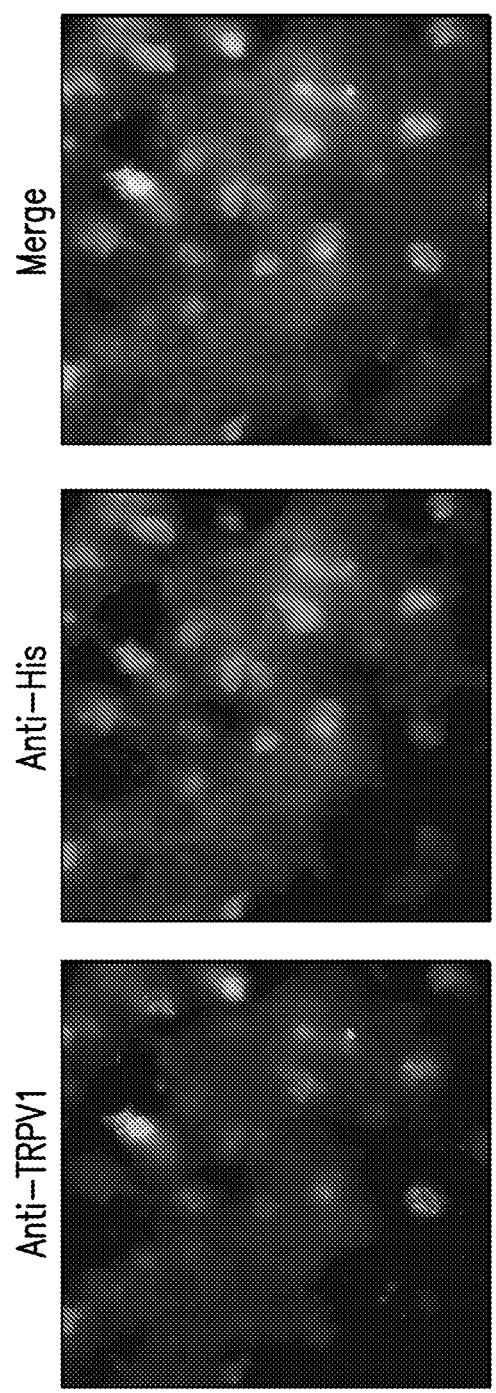
FIG. 9. In vitro and in vivo studies on PC12 TRPV1$^{His}$/insulin stable cell line. (A) Proinsulin release from PC 12 cells stably expressing TRPV1$^{His}$ and calcium dependent human insulin was significantly increased by a temperature above the threshold for TRPV1 activation (Same letter indicates p<0.05). (B) RF treatment significantly increased proinsulin release from PC12 cells stably expressing TRPV1$^{His}$ and calcium dependent human insulin. (Same letter indicates p<0.01). (C) RF treatment significantly increases insulin gene expression in PC12 cells stably expressing TRPV1$^{His}$ and calcium dependent human insulin (Same letter indicates p<0.05). (D) Time course of proinsulin release from PC12 cells stably expressing TRPV1$^{His}$ and calcium dependent human insulin. RF treatment for 15 minutes significantly increased proinsulin release. (E) Serial blood glucose measurement in nude mice injected with PC12 cells expressing TRPV1His and calcium dependent human insulin to form a subcutaneous tumor. (F) Immunohistochemistry for TRPV1 and His epitope tag in sections from tumors formed following subcutaneous injection of PC12 cells stably expressing TRPV1$^{His}$ and calcium dependent human insulin.

HEK 293T cells expressing the Ca$^{2+}$-dependent human insulin construct and TRPV1$^{His}$ were incubated with functionalized FeNPs. RF treatment of the FeNP-decorated cells resulted in a significant increase in proinsulin release (RF-treated 671±235% (SEM) basal versus 100±13.9% for controls, P<0.02) and insulin gene expression (RF-treated 2.20±0.53 insulin gene expression relative to basal versus 1.0±0.18 for controls, P<0.05). These were blocked by the TRP channel inhibitor, ruthenium red (FIG. 6A). There was a trend toward an increase in proinsulin release after 15 min of RF treatment (likely through release of a small pool of preformed insulin-containing vesicles), with significant proinsulin release at 1 hour when insulin gene expression had also significantly increased (FIG. 6B). Control studies confirmed that proinsulin release required all system components (i.e., TRPV1, nanoparticles, and RF magnetic field) and that RF-dependent insulin secretion was confined to FeNP-decorated cells (FIG. 5B-C). RF treatment induced NFAT translocation into the nucleus, and RF-dependent proinsulin release was blocked by a calcineurin inhibitor, tacrolimus (FIG. 5D-E). RF treatment of cells incubated with FeNPs (1 to 8 mg/ml) did not induce apoptosis as assessed by immunohistochemistry for active caspase 3 (Tewaari et al., 1995 Cell 81:801)) and terminal deoxynucleotidyl transferase-mediated deoxyuridine triphosphate nick end labeling (TUNEL) (Gavrieli et al 1992 J. Cell Biol. 119:493) (FIG. 5F-G). It was also shown that RF could stimulate proinsulin release from mouse embryonic stem cells expressing TRPV1$^{His}$ and the Cat*-dependent human insulin construct (FIG. 7).

Next, a comparison was made of the single-component system to a multicomponent system previously reported (Huang et al., 2010 Nat. Nanotechnol. 5:602) and composed of (i) a membrane-tethered biotin acceptor protein, (ii) a bacterial biotin ligase to biotinylate this protein to enable binding of (iii) streptavidin-coated nanoparticles, and (iv) a wild-type TRPV1 as the effector. Although this system induced Ca$^{2+}$ entry in vitro and activated endogenous temperature sensing of *Caenorhabditis elegans* neurons, the complete system was not tested in vivo because the exogenous TRPV1 channel was not used in this prior study. It was found that the single-component system had denser nanoparticle binding, faster calcium entry, and a trend toward more robust proinsulin release (FIG. 8A-G). These attributes led to the testing of the single-component TRPV1$^{His}$ system in vivo in mice by using xenografts of engineered neuroendocrine PC12 cells, which robustly secrete peptides via the regulated pathway for protein secretion.

Figure 10D:
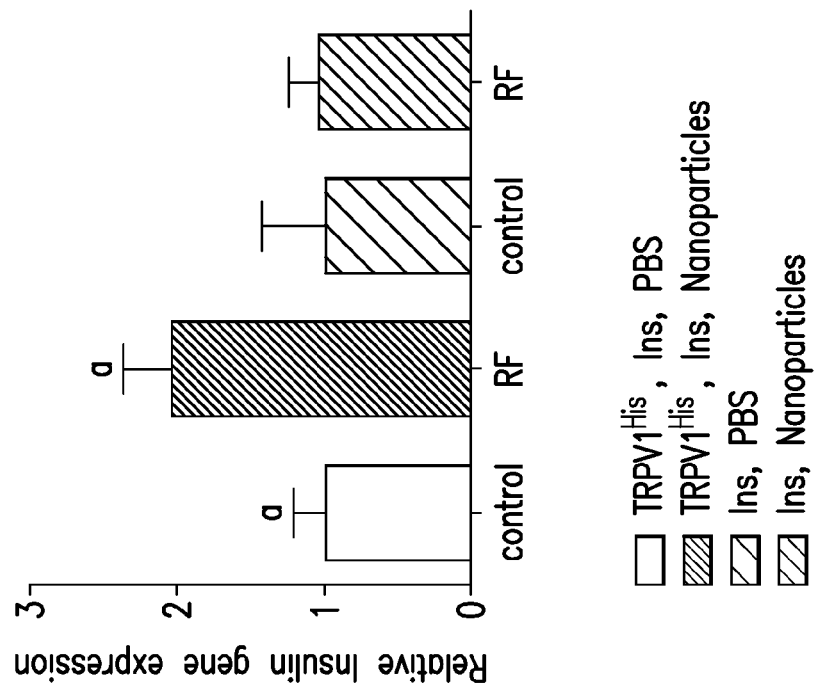
FIG. 10. Nanoparticle regulation of blood glucose in vivo. (A) Effects of RF treatment on blood glucose in PBS and nanoparticle-treated mice with tumors expressing TRPV1$^{His}$ and calcium-dependent human insulin. RF treatment significantly reduces blood glucose in nanoparticle-treated mice compared with that of PBS-treated mice. (Asterisks indicate P<0.05. Error bars indicated SEM.) (B) RF treatment of mice with tumors expressing TRPV1$^{His}$ and calcium-dependent human insulin injected with nanoparticles significantly reduces blood glucose over the course of the study as assessed by the area under the curve. There is no effect in mice with tumors expressing calcium-dependent insulin alone without TRPV1$^{His}$ (same letter indicates P<0.05.) (C) Plasma insulin is significantly increased by RF treatment in nanoparticle-treated but not PBS-treated mice with tumors expressing TRPV1$^{His}$. (Same letter indicates P<0.05). (D) Insulin gene expression is significantly increased in the tumors expressing TRPV1$^{His}$ and calcium-dependent human insulin treated with nanoparticles and RF magnetic field but not in tumors expressing calcium-dependent human insulin alone without TRPV1$^{His}$.
Figure 10C:
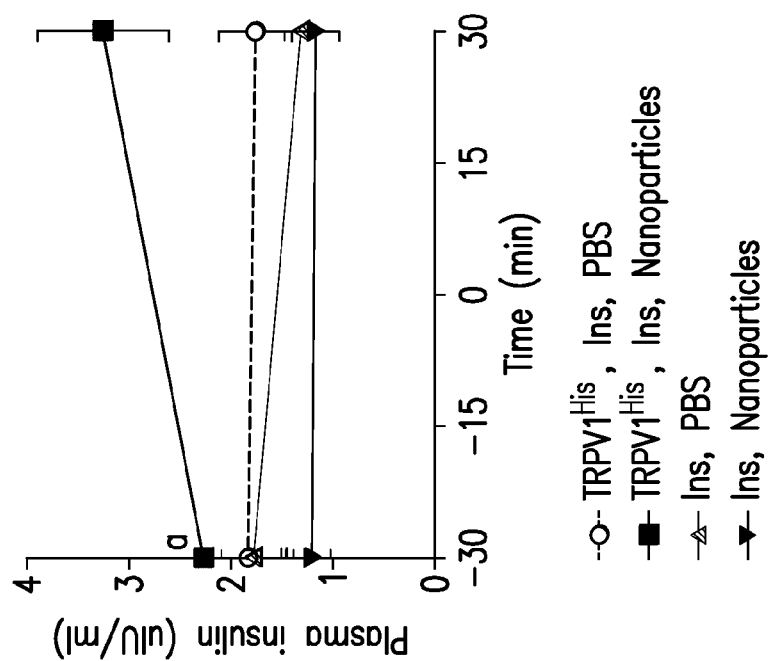
Figure 11B:
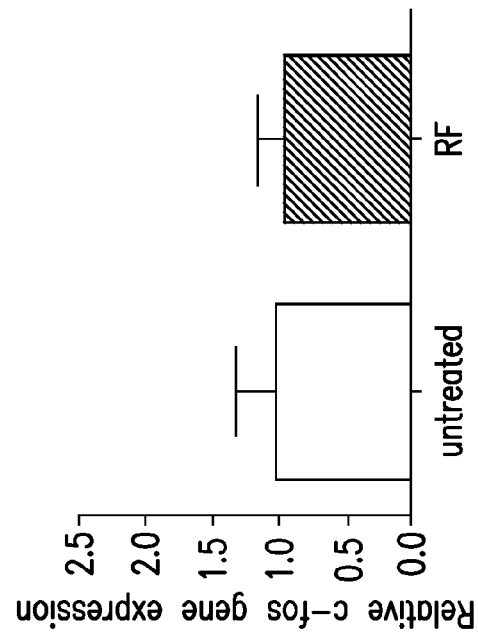
FIG. 11. Nanoparticle regulation of blood glucose in vivo. (A) Protocol for assessment of effects of RF treatment on blood glucose in mice bearing tumors expressing TRPV1$^{His}$ and calcium dependent human insulin. At time −30 min, mice are anesthetized and injected with PBS or nanoparticles. RF stimulation begins at time 0 and continues for 30 mins. Mice remain anesthetized for a further 30 mins. Samples for plasma insulin are taken at −30 and +30 mins and samples for blood glucose are taken before, during and after RF stimulation. (B) Expression of c-fos gene in tumors showed no difference in levels between control (untreated) and RF treated tumors. (C) No increase in apoptotic cells from nanoparticle and RF treated tumors as assessed by TUNEL. (D) No increase in apoptotic cells from nanoparticle and RF treated tumors as assessed by immunohistochemistry (IHC) for activated Caspase-3. (E) Effects of RF treatment on blood glucose in PBS and nanoparticle treated mice with tumors expressing TRPV1$^{His}$ and calcium dependent human insulin. RF treatment significant reduces blood glucose in nanoparticle treated mice compared to PBS treated mice in both the first and second study separated by a week. (Asterisk indicates p<0.05.) (F) Cumulative blood glucose change, measured by area under the curve, shows a significant decrease in nanoparticle treated mice compared to PBS treated mice in both the first and second study. There is no significant difference between the AUC for the nanoparticle studies.
Figure 11A:
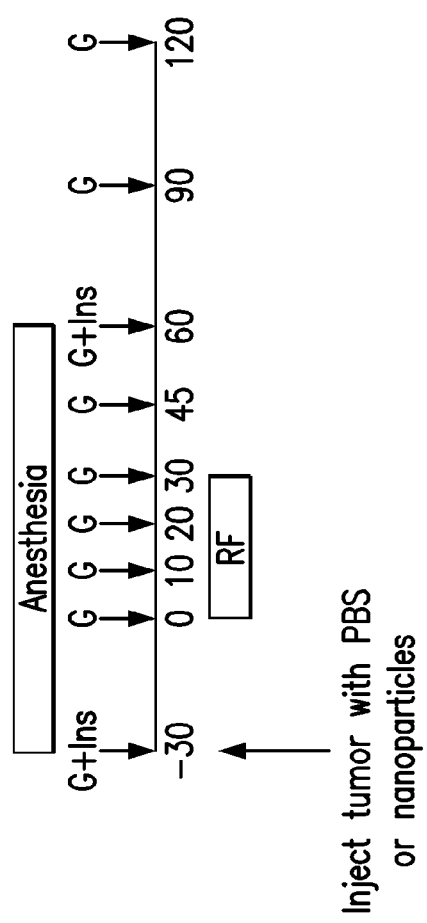
Figure 11D:
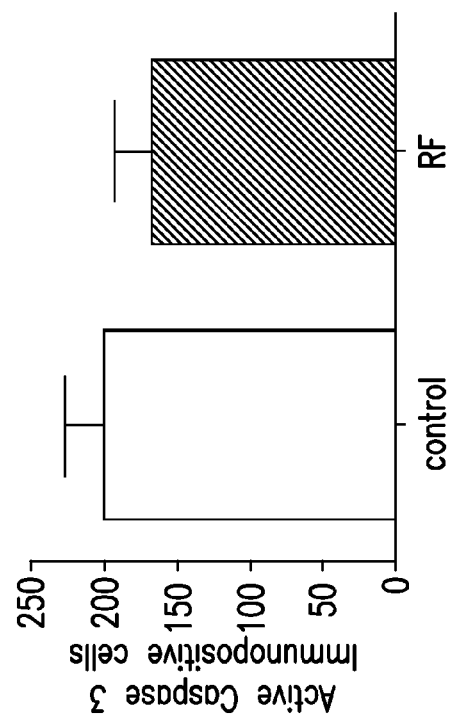
Figure 11C:
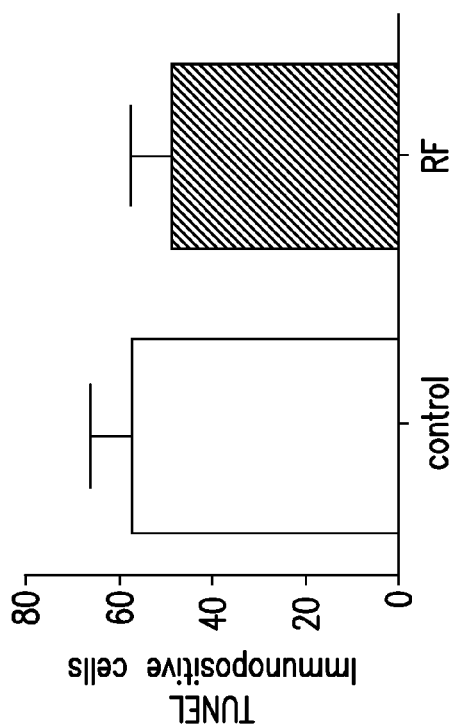
Figures 11E, 11F:
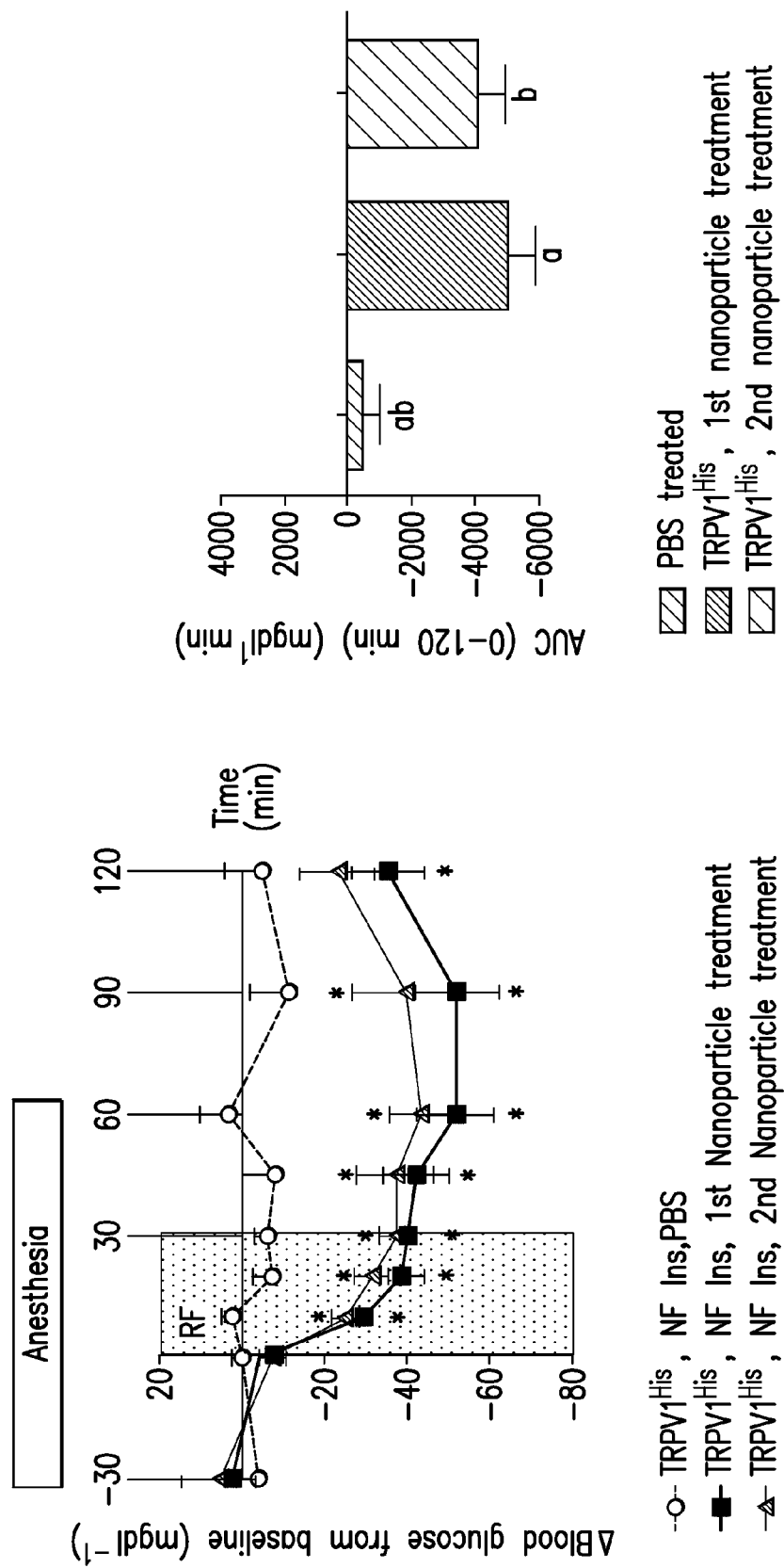
Figure 12A:
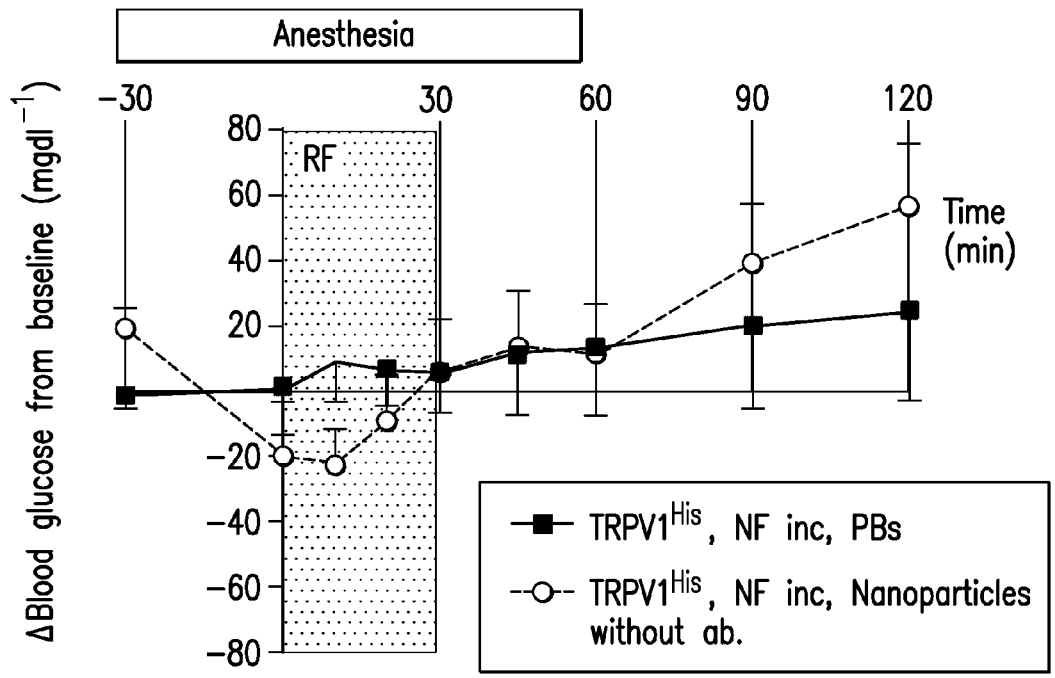
FIG. 12. Effect of NICE in the absence of TRPV1, absence of anti-His antibodies and temperature studies in vivo. (A) Effect of RF stimulation on blood glucose in PBS and nanoparticle treated mice bearing tumors expressing calcium dependent insulin gene without TRPV1. (B) Effect of RF stimulation on blood glucose in mice treated with PBS or nanoparticles which have not been conjugated to anti-His antibody. (C) Thermal imaging using an infrared camera on mouse with tumor expressing TRPV1$^{His}$ and calcium dependent human insulin injected with iron oxide nanoparticles before (left panel) and after (right panel) RF magnetic field treatment. (D) Core body temperature and intra-tumor temperature recordings from mice with TRPV1$^{His}$ expressing tumors following nanoparticle injection and RF treatment. There is no difference in the intratumoral temperature achieved with RF treatment in the tumors of mice with TRPV1$^{His}$ and insulin expression compared to the tumors of mice with insulin expression but without TRPV1$^{His}$ expression.
Figure 12B:
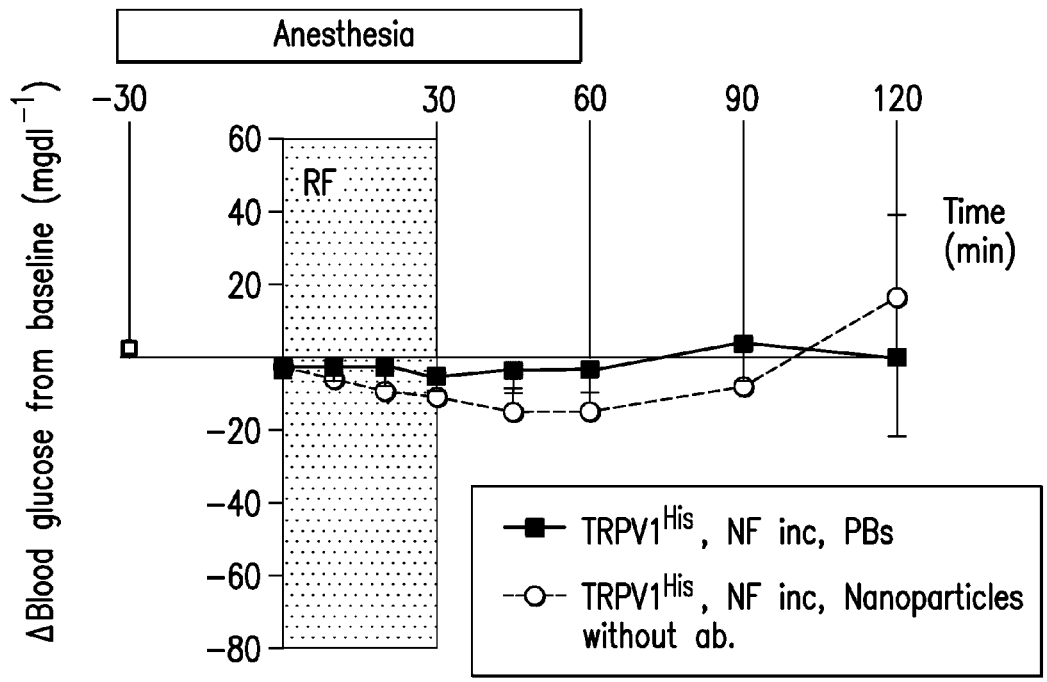
Figure 12C:
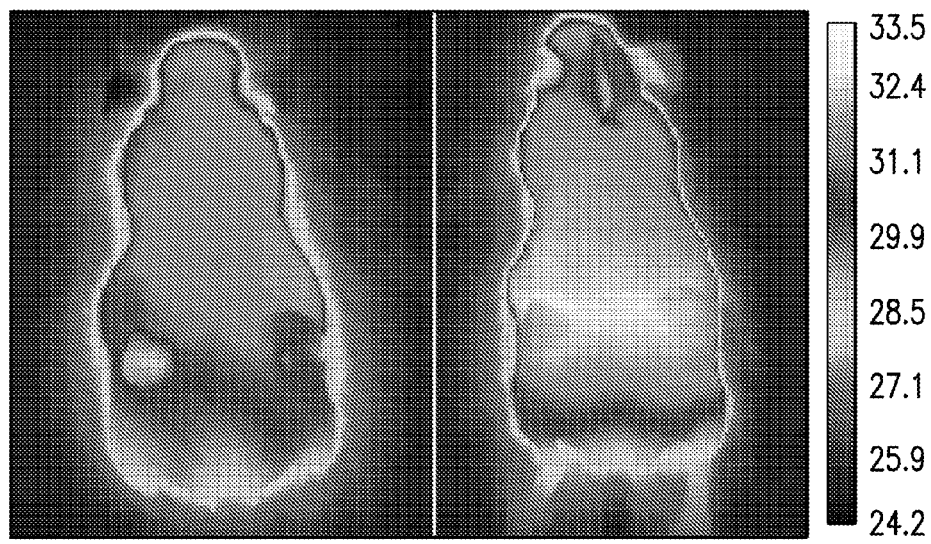
Figure 12D:
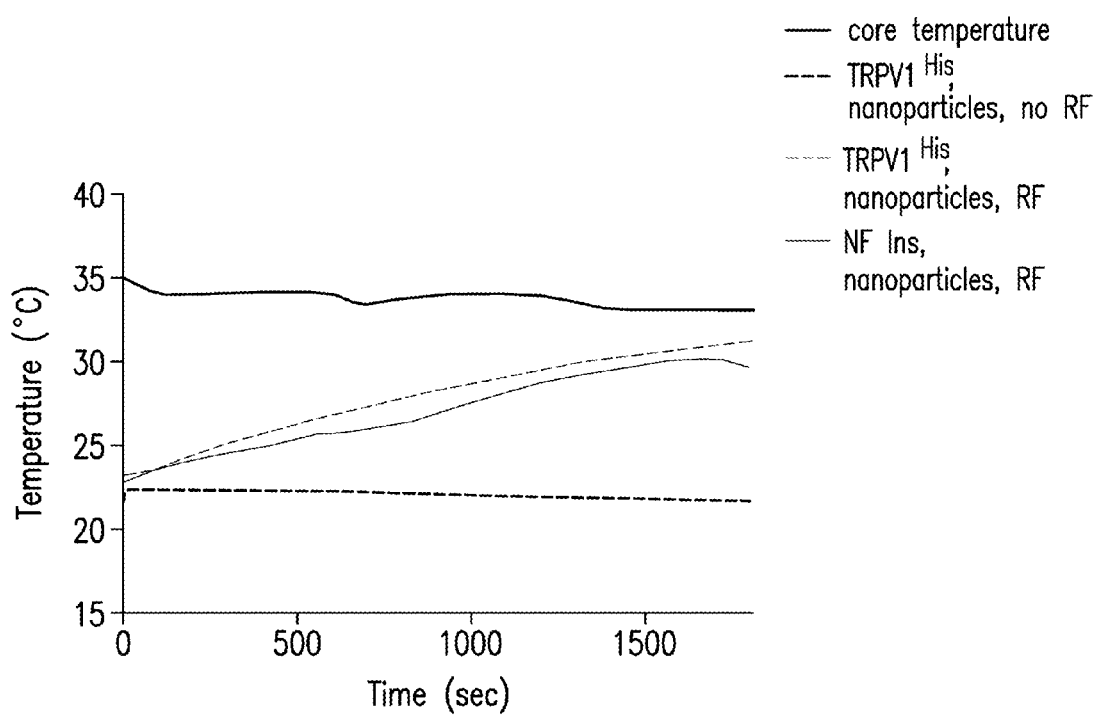

Exposure of a PC-12 cell line stably expressing TRPV1$^{His}$ and the calcium-dependent human insulin construct (PC12-TRPV1$^{His}$-Ins) to RF after FeNP application significantly increased proinsulin release and insulin gene expression in vitro (FIG. 9A-D). The PC12-TRPV1$^{His}$-Ins cells were injected subcutaneously into the flank of nude mice to form tumors (FIG. 9F). There was no change in plasma glucose with tumor growth (FIG. 9E). Phosphate-buffered saline (PBS) or FeNP (50-µl total volume, nanoparticle concentration of 8 mg/ml) were injected into the tumors of fasted mice, and blood glucose and plasma insulin were measured before, during, and after RF application (see FIG. 11A for protocol). RF treatment resulted in a significant decrease in blood glucose in nanoparticle-treated PC12-TRPV1$^{His}$-Ins tumor mice (FIG. 10A) (The change in blood glucose at 30 min for FeNP-treated was −53.6±8.90 mg/dl, versus PBS-treated, −11.0±9.72 mg/dl; P<0.005. At 45 min, the change in blood glucose for FeNP-treated mice was −60.9±11.6 mg/dl versus PBS-treated −9.74±8.52 mg/dl; P<0.005. At 60 min, the change in blood glucose for FeNP-treated mice was −55.1±13.2 mg/dl versus PBS-treated, −6.24±15.3 mg/dl; P<0.0001). There was also a highly significant difference in the cumulative change in blood glucose (area under the curve, AUC) between PBS-treated and FeNP-treated PC12-TRPV1$^{His}$-Ins tumor mice over the course of the study (FIG. 10B) [AUC (0 to 120 min) for PBS-treated was 272±692 mg/dl min versus FeNP-treated, −2695±858.3 mg/dl min; P<0.002]. Plasma insulin was significantly increased after RF treatment in FeNP-treated but not PBS-injected mice (FIG. 10C) [plasma insulin for FeNP-treated (−30 min) was 2.26±0.76 μI-U/ml (where 1 μI-U/ml=0.006 pmol/l) versus FeNP-treated (30 min), 3.25±0.64 μI-U/ml; P<0.05. PBS-treated (−30 min) was 1.83±0.38 μI-U/ml versus PBS-treated (30 min), 1.75±0.36 μI-U/ml]. Lastly, insulin gene expression was significantly increased in RF-treated, FeNP-injected tumors (FIG. 10D) (relative insulin gene expression in FeNP-treated, no RF samples was 1.0±0.2 versus FeNP-treated with RF, 2.0±0.3, P<0.05) without increasing c-fos expression (FIG. 11B). Core temperature did not change significantly with RF exposure, and the intratumoral temperatures (23° to 31° C.) remained well below the 42° C. threshold of TRPV1, indicating that cell activation is due to localized, cell surface-specific gating of TRPV1. There was no difference in apoptosis between FeNP-injected tumors in the presence or absence of the RF magnetic field (FIG. 11C-D). A significant decrease in blood glucose was also seen with serial FeNP injection and RF treatment (FIG. 11E-F). To confirm that the effects on blood glucose were not due to nonspecific insulin release via thermal effects of nanoparticles on the tumor, the in vivo study was repeated, first in mice injected with PC12 cells expressing the $Ca^{2+}$-dependent human insulin construct but not $TRPV1^{His}$ and then in mice with tumors expressing $TRPV1^{His}$ and insulin but injected with nanoparticles without anti-His conjugation. There was no significant effect on blood glucose in either study after PBS or FeNP injection and RF treatment despite similar intratumoral temperatures (FIG. 12A-D).

Figure 13A:
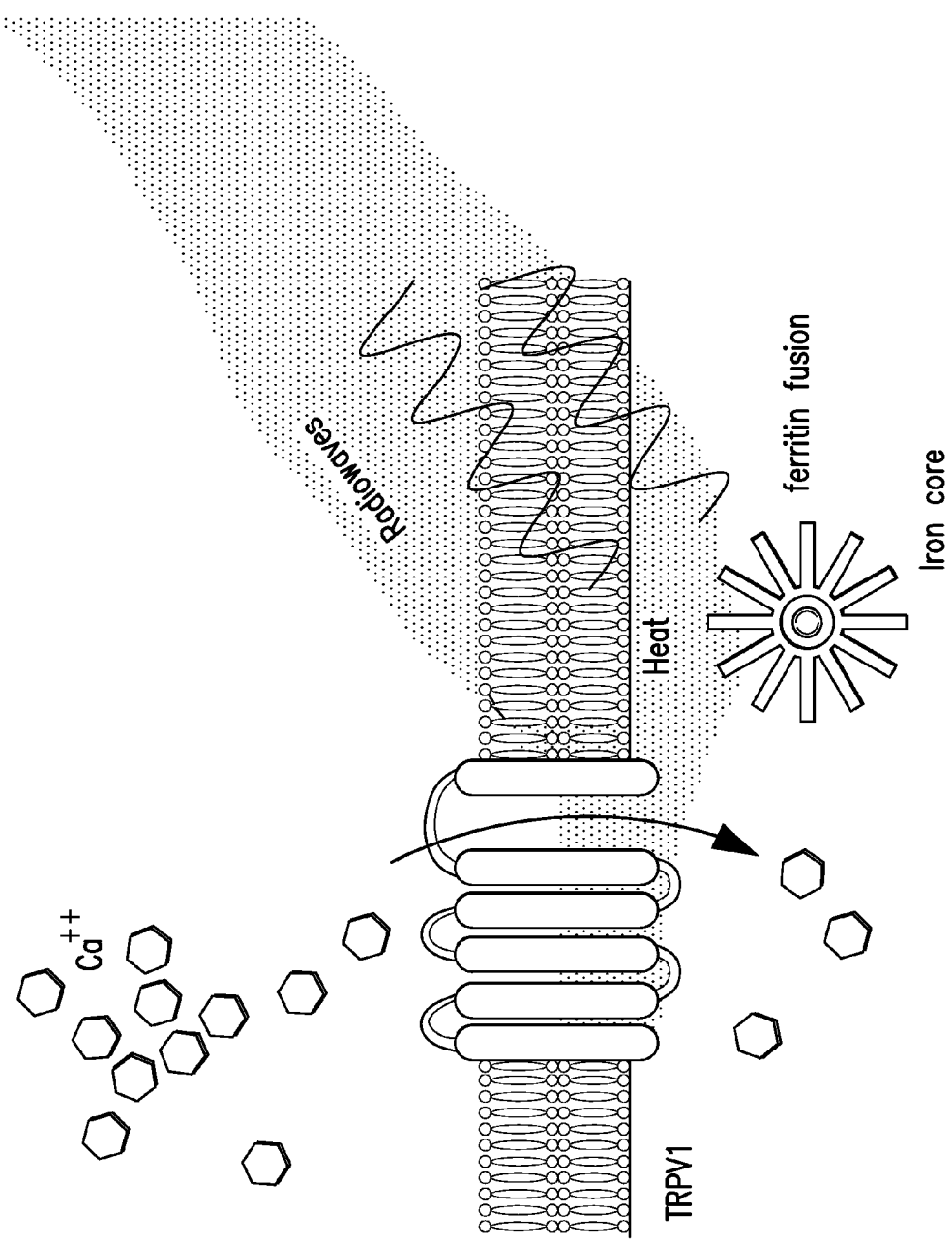
FIG. 13. Intracellular nanoparticle synthesis and cell activation. (A) Schema of intracellular nanoparticle synthesis and cell activation. A ferritin fusion protein is composed of a ferritin light chain fused to ferritin heavy chain with a flexible linker region. Heating of the iron core by a RF magnetic field opens the TRPV1 channel to trigger calcium entry, as previously described. (B) RF treatment increases proinsulin release in vitro. HEK293 T cells transiently transfected with TRPV1, ferritin fusion protein, and calcium-dependent human insulin show a significant increase in proinsulin release in response to RF treatment. (Same letter indicates significance, P<0.05.) RF treatment does not increase proinsulin release from cells expressing ferritin in the absence of TRPV1. (C) RF treatment increases insulin gene expression in vitro. Insulin gene expression is significantly increased by RF treatment in cells transfected with TRPV1, ferritin fusion protein, and calcium-dependent human insulin. (Same letter indicates significance, P<0.05). RF treatment does not increase insulin gene expression in cells expressing ferritin fusion protein in the absence of TRPV1.
Figure 13C:
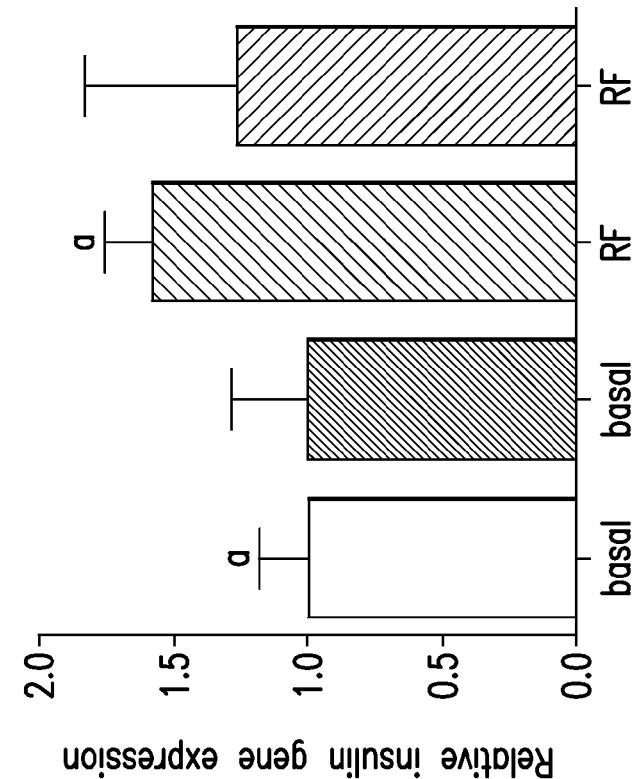
Figure 13B:
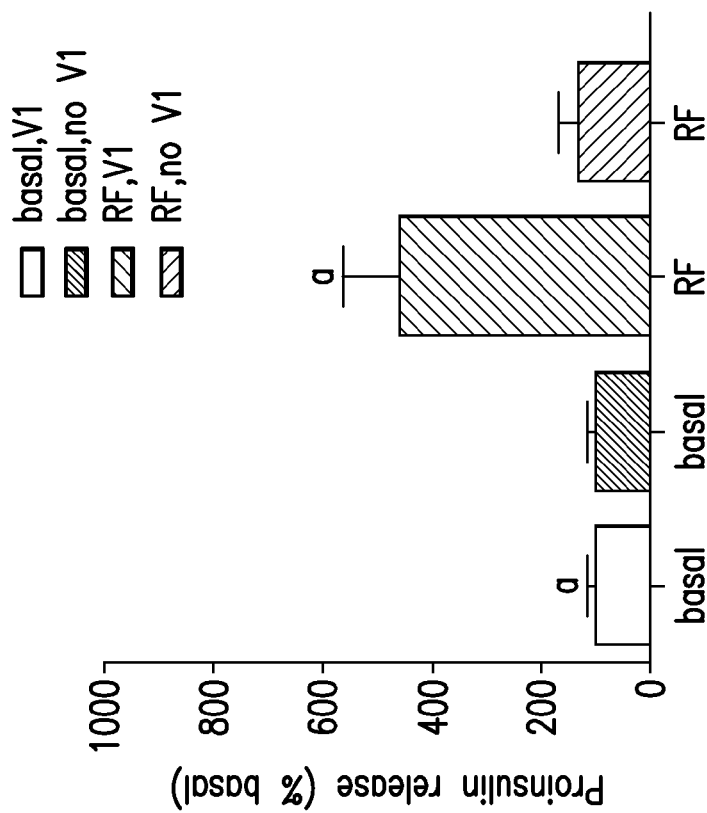
Figure 14B:
FIG. 14. Expression of Ferritin fusion protein in vitro. (A) Ferritin expression as shown by IHC for ferritin light chain. (B) Electron micrograph of iron loaded ferritin in transfected cells. Scale bar 200 nm.
Figure 14A:
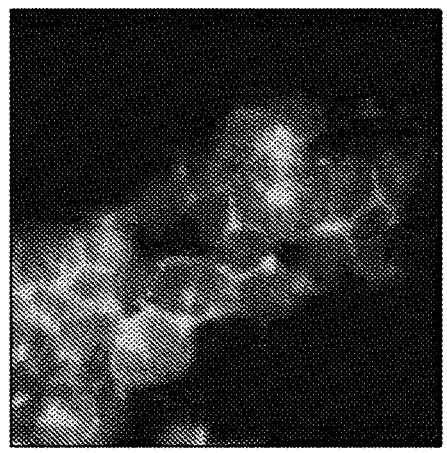

The above approach requires direct application of nanoparticles to TRPV1 expressing cells by incubation (in vitro) or injection (in vivo). An alternative is to engineer cells to synthesize nanoparticles intracellularly. For this purpose, the iron storage protein ferritin was chosen, which forms a naturally occurring iron nanoparticle (Farrant, 1954 Biochim. Biophys. Aca 13:569; Sana et al., 2010 Biointerphases 5:FA48) (FIG. 13A, FIG. 14). Ferritin has been stably overexpressed in mice for over 2 years without evident pathology (Ziv et al., 2010 NMR Biomed 23:523). A fusion peptide of ferritin light chain, flexible linker region, and ferritin heavy chain fixes the ratio of light to heavy chains and increases iron binding (Iordanova et al., 2010 J. Biol. Inorg. Chem. 15:957). Transfecting cells with ferritin fusion protein resulted in 12.6±2.86 ferritin particles per 0.2 μm² with an average distance to the cell membrane of 60.3±2.85 nm (FIG. 14B). RF treatment of cells expressing the ferritin fusion protein, TRPV1, and Ca2+-dependent human insulin significantly increased proinsulin release (RF treated, 457±103% basal versus control, 100±14.9% basal; P<0.005) and insulin gene expression (relative insulin gene expression for RF treated, 1.58±0.19 versus control, 1.0±0.17; P<0.05) (FIG. 13B). Intracellularly generated FeNPs were roughly two-thirds as effective in stimulating proinsulin release as exogenous FeNP. In the absence of TRPV1, insulin secretion and gene expression were unchanged in ferritin-expressing cells. Thus, ferritin expression may provide a genetically encoded source of nanoparticles for RF-mediated cell activation.

As disclosed herein both externally applied and endogenously synthesized nanoparticles can be heated by radio waves to remotely activate insulin gene expression and secretion. RF-mediated cell activation does not require a permanent implant, and the cells to be activated can be localized (when using exogenous nanoparticles) or dispersed (by using genetically encoded nanoparticles). Genetically encoded ferritin nanoparticles may also provide a continuous source of nanoparticles for cell activation.

The use of an epitope-tagged TRPV1 with antibody-coated nanoparticles resulted in high nanoparticle density in proximity to the channel and could gate calcium in response to power levels of a 465-kHz RF field that are within Food and Drug Administration guidelines (Halperin et al., 2008 Proceedings of the 2008 IEEE Symposium on Security and Privacy Oakland Calif. May 18-21 2008 p. 129-142). The use of a single construct for particle binding and calcium entry also simplifies DNA delivery using viral vectors or other approaches (Nathwani et al., 2011 N. Engl. J. Med. 365: 2357). Additionally, an epitope-tagged channel offers the choice of activating distinct cell populations in the same organism with different RFs to selectively and independently heat nanoparticles bound to cell specific tags. For endogenous particles, mutations of ferritin that alter the metal it encapsulates could enable combinatorial cell activation (Butts et al., 2008 Biochemistry 47:12729).

A noninvasive, nonpharmacological means has been developed for cell stimulation and validated it in vitro and in vivo. This system provides a useful tool for basic research and represents an initial step toward noninvasive regulation of protein production for possible therapeutic purposes. This approach could be used to treat protein deficiencies by providing regulated expression of proteins that are difficult to synthesize or to deliver [such as central nervous system (CNS) replacement of hexosaminidase A for Tay-Sachs] or to allow CNS delivery of recombinant antibodies to treat brain metastases. This approach could also enable the activation of other $Ca^{2+}$-dependent processes, such as muscle contraction or firing of action potentials.

Example 2

Nanoparticle Induced Cell Excitation

Effects of NICE In Vivo.

Figure 20A:
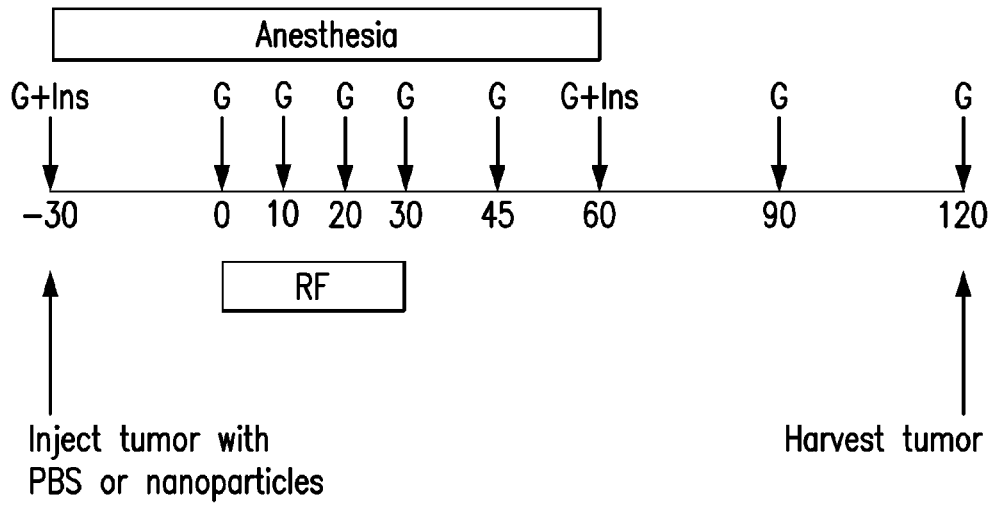
FIG. 20 shows the effect of NICE in vivo. (A) Protocol to examine the effect of RF on blood glucose and insulin in vehicle or nanoparticle injected TRPV1/NFAT-insulin tumors in nude mice. (B) Effect of RF on blood glucose in vehicle (PBS) or nanoparticle injected mice. A significant difference in blood glucose is seen at 30, 45 and 60 minutes. (C) Assessment of area under the curve for circulating blood glucose shows a significant difference between PBS and nanoparticle treated groups between 0 and 120 minutes. (D) Circulating insulin levels increase significantly in nanoparticle treated mice. (E) Insulin gene expression, as assessed by qPCR, is significantly increased in RF treated tumors.
Figure 20B:
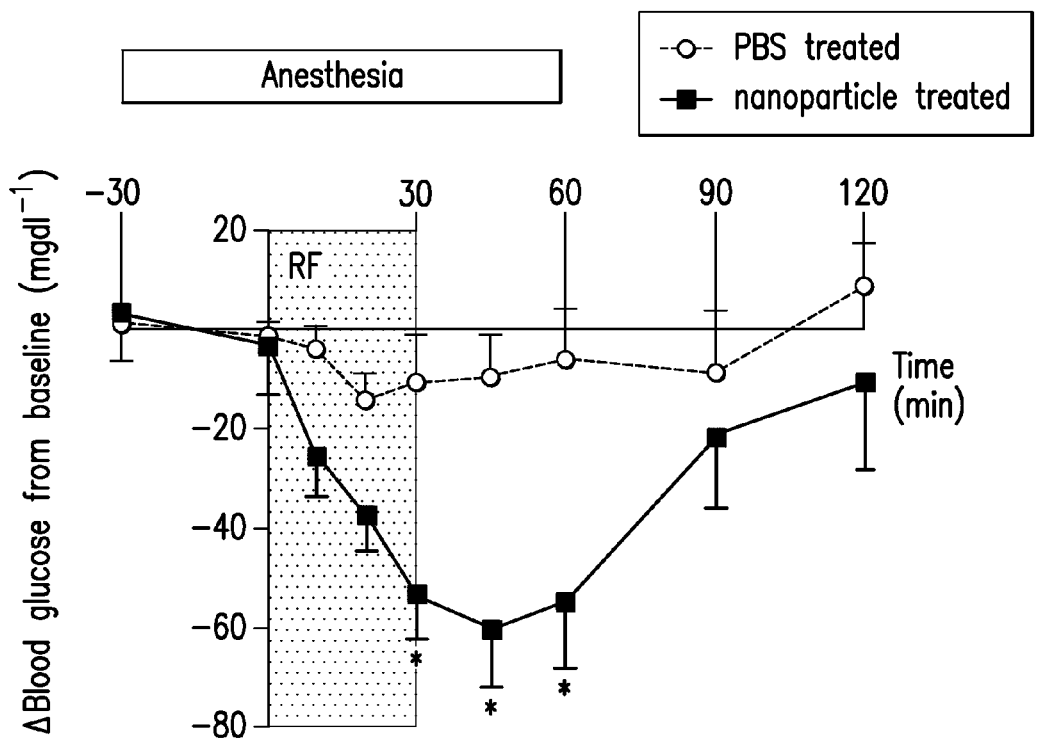
Figure 20C:
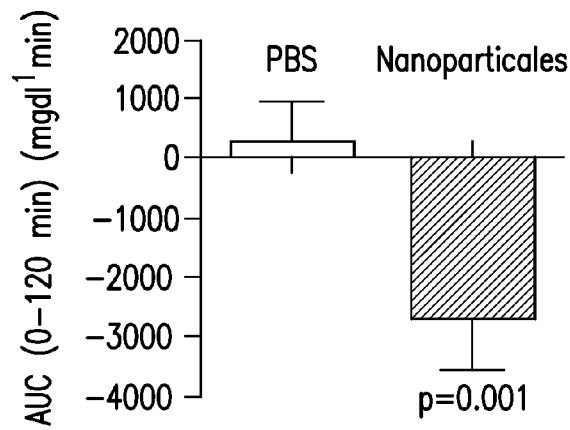
Figure 20D:
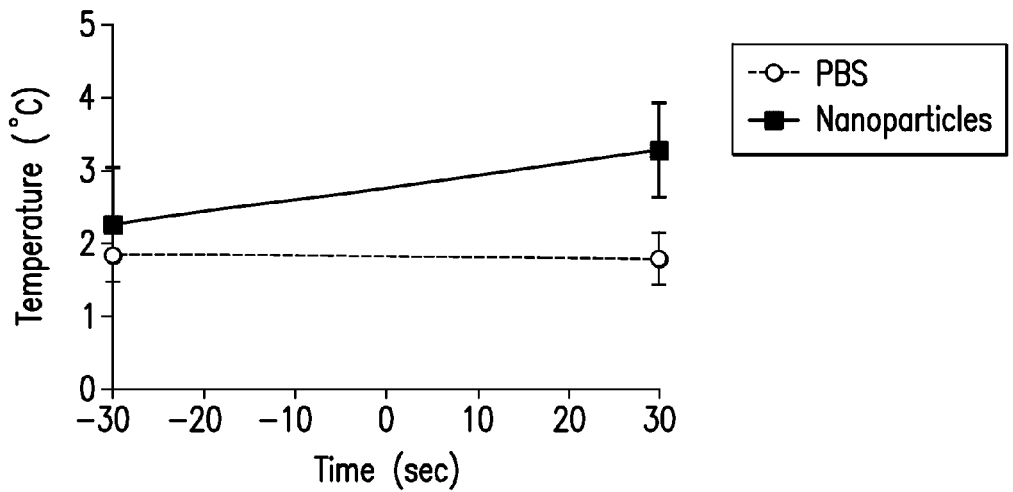
Figure 20E:
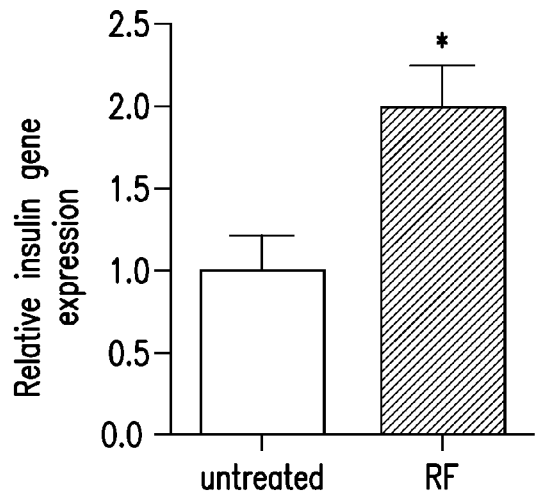

Data is provided herein which shows the effectiveness of NICE in vivo. For these studies the effect of NICE on insulin release was examined in implanted cells. Stably transfected PC12 cells expressing TRPV1, a nanoparticle tether and insulin driven by a calcium dependent promoter (NFAT-insulin) were implanted into nude mice to form subcutaneous tumors. In a cross-over design, either vehicle (PBS, 5×10 ul) or functionalized nanoparticles (20 nm, 5×10 ul) were injected into each tumor (n=8 mice). Thirty minutes after injection, mice were exposed to a radiofrequency field (RF) for a period of 30 minutes. Blood glucose and insulin were monitored and the tumors harvested at the end of the study period. This protocol is described visually in FIG. 20A. Mice receiving nanoparticle injection and RF showed a significant reduction in blood glucose, a significant increase in circulating insulin and a significant increase in tumor expression of insulin (FIG. 20B-E). There was no difference in apoptosis between groups based on immunohistochemical assessment of TUNEL or activated caspase-3.

The results demonstrate the usefulness of NICE as a tool for non-invasive stimulation of cell function in vivo. Additional studies can be performed to examine the effect of stimulating endogenous cell populations using transgenic mice expressing a nanoparticle tether and TRPV1, with or without calcium dependent gene expression. It is also possible to examine the effects of stimulating cell populations derived from individual-specific induced pluripotent stem cells (iPSC) injected into immune-competent mice. Viral free iPSC populations can be reprogrammed to a wide variety of tissues and also modified to express NICE components. These cell populations would allow the non-invasive study of specific stimulation of defined cell types and/or defined genes within these cells providing a valuable tool in the investigation of cell function particularly as it pertains to complex behaviors.

Intracellular Nanoparticle Synthesis.

In its present form, NICE technology requires external nanoparticle application by incubation (in vitro) or injection (in vivo). For peripheral tissues, this may be achieved by intravenous administration but modulation of neuronal activity requires intracerebral administration. This is advantageous in some situations where stimulation of an anatomically defined subpopulation of a dispersed neural group is needed. However, a variation of the existing NICE technology with intracellular nanoparticle synthesis using chimeric ferritin proteins targeted to an intracellularly tagged TRPV1 channel is being studied.

Figure 21A:
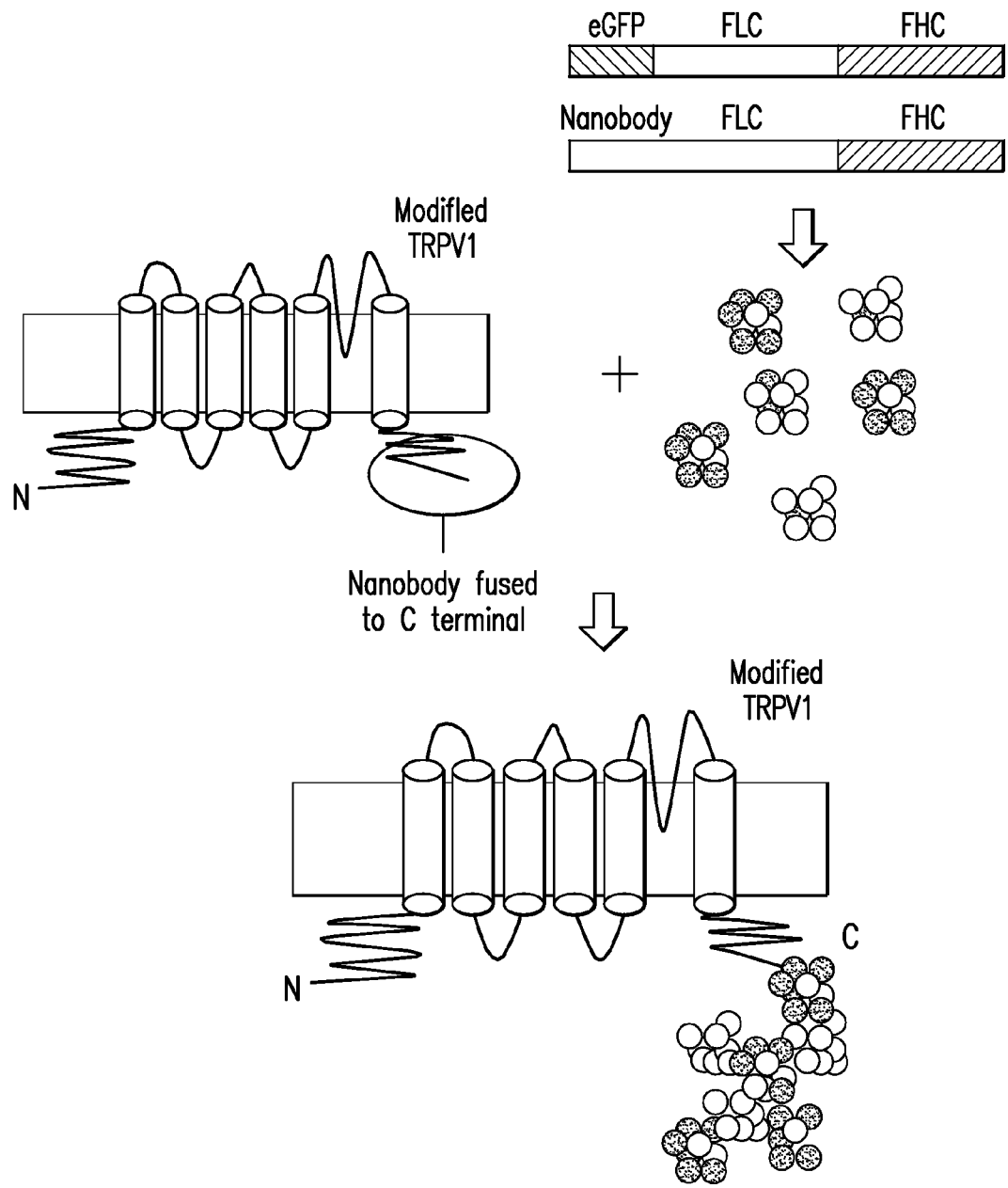
FIG. 21. shows a schema of intracellular nanoparticle synthesis using ferritin chimeras. (A) Iron binding chimeric ferritin peptides composed of ferritin light chain (FLC) and ferritin heavy chain (FHC) with a flexible linker sequence (pink box) are fused to either EGFP (green box) or the high affinity camelid anti-GFP antibody (yellow box). When these are expressed they form ferritin complexes with either EGFP or nanobody at the surface. The nanobody peptide is also fused to the intracellular C terminal of the temperature sensitive calcium channel, TRPV1. Expression of all three components in the cell results in an iron containing ferritin aggregate attached to the intracellular C terminal of TRPV1. (B) Electron microscopy image of chimeric ferritin complexes (arrows) in 293t cells transfected with egfp-chimeric ferritin and nanobody-chimeric ferritin. (C) Cell surface expression of HA-tagged nanobody fused to TRPV1 in transfected 293t cells.
Figure 21B:
Figure 21C:
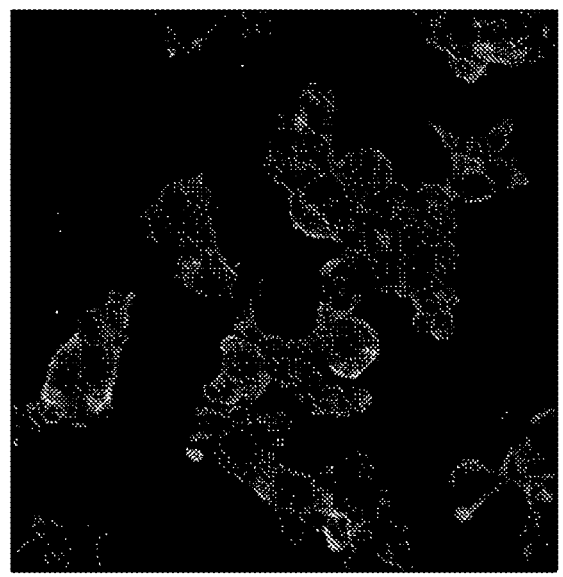

The iron storage protein, ferritin, is a complex of heavy and light chains that is capable of binding 4500 ferric ions or picograms of iron per cell. This iron binding capacity has allowed ferritin to be utilized as an MRI contrast agent in many studies. Two chimeric ferritin peptides have been developed, one fused at the N-terminal to Egfp and one fused to a highly stable, high affinity (subnanomolar) camelid anti-gfp antibody known as a nanobody (FIG. 21A). These adaptations allow adjacent ferritin complexes to bind to form ferritin aggregates and EM images show these are of the order of 40-50 nm diameter (FIG. 21B). In addition, the temperature dependent calcium channel, TPRV1, is modified by attaching the nanobody sequence to its intracellular N-terminal which then tethers the ferritin aggregate. This brings the heating component (ferritin bound iron) and the effector component (TRPV1) of NICE together at the cell surface.

Figure 15:
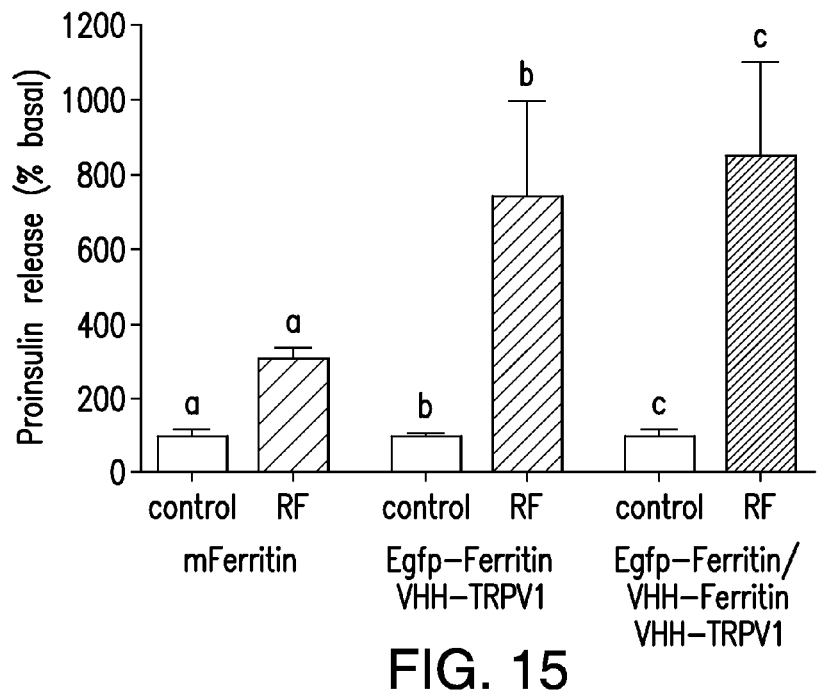
FIG. 15. Release of proinsulin with RF (465 kHz) from 293 cells transfected with TRPV1 and myristoylated ferritin fusion protein (mFerritin), transfected with TRPV1 with n-terminal fusion of camelid antibody to EGFP (vhh-TRPV1) and EGFP fused to ferritin fusion protein and transfected with TRPV1 with n-terminal fusion of camelid antibody to EGFP (vhh-TRPV1), EGFP fused to ferritin fusion protein and camelid antibody fused to ferritin fusion protein along with calcium dependent insulin gene.
Figure 16A:
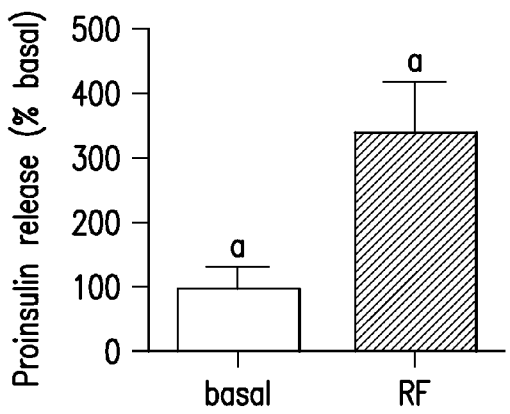
FIG. 16. Release of proinsulin from (A) embryonic stem cells from C57BL6 mice expressing TRPV1, myristoylated ferritin fusion protein and calcium dependent insulin, decorated with nanoparticles and treated with RF and (B) mesenchymal stem cells from C5BL6 mice expressing TRPV1, myristoylated ferritin fusion protein and calcium dependent insulin and treated with RF.
Figure 16B:
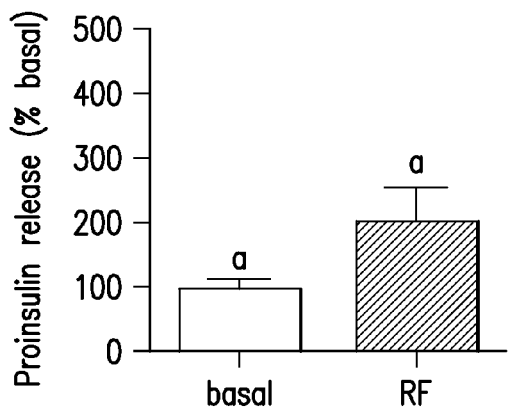
Figure 17:
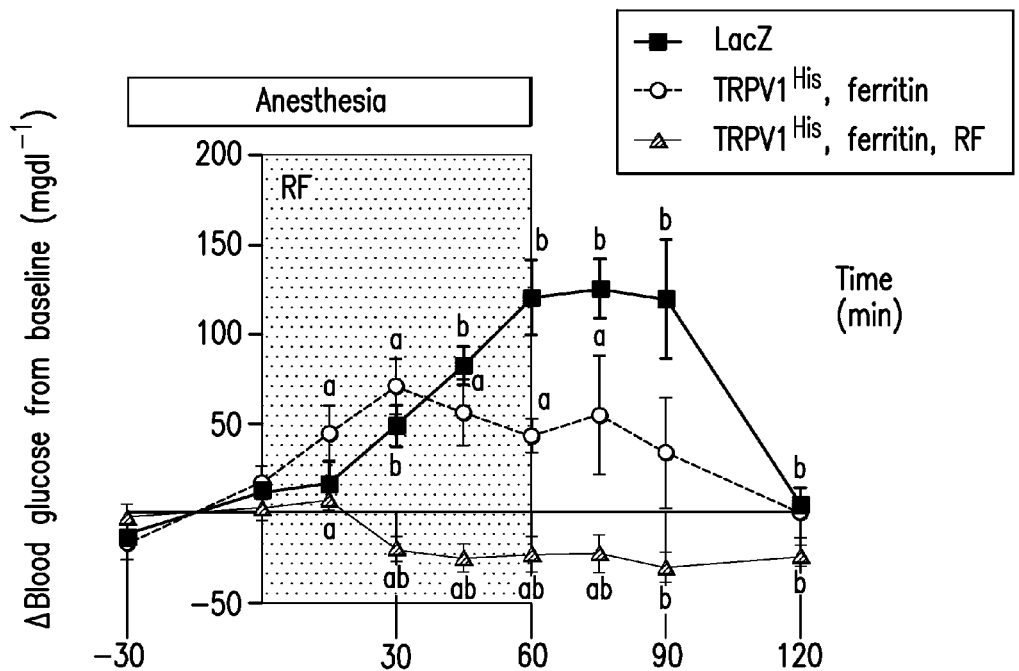
FIG. 17. Regulation of blood glucose in wild-type mice. C57BL6 mice received in injection of replication deficient adenovirus expressing TRPV1, myristoylated ferritin fusion protein (mferritin) and calcium dependent insulin or adenovirus expressing LacZ. Two weeks after injection, mice were fasted overnight and anesthetized then treated with RF for 1 hour and blood glucose monitored. RF treatment of TRPV1/mferritin/calcium dependent insulin significantly reduced blood glucose compared to baseline and compared to either RF treated LacZ expressing mice or mice expressing TRPV1/mferritin/calcium dependent insulin without RF treatment.
Figure 18A:
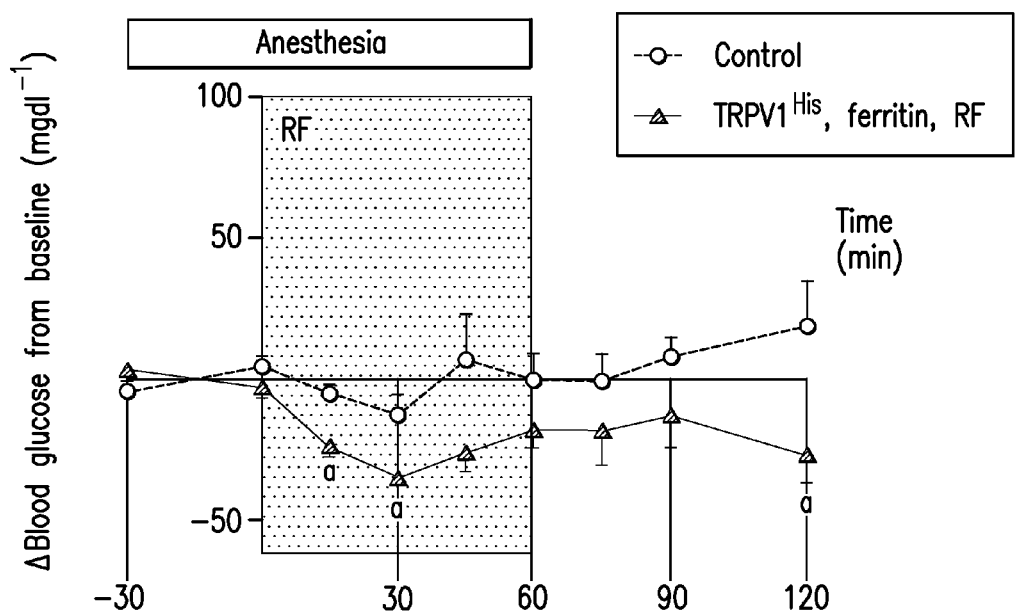
FIG. 18 (A) Change in blood glucose and (B) change in blood glucose expressed as area under curve in nude mice injected with mesenchymal stem cells alone (control) and treated with RF or mesenchymal stem cells expressing TRPV1, mferritin and calcium dependent insulin and treated with RF.
Figure 18B:
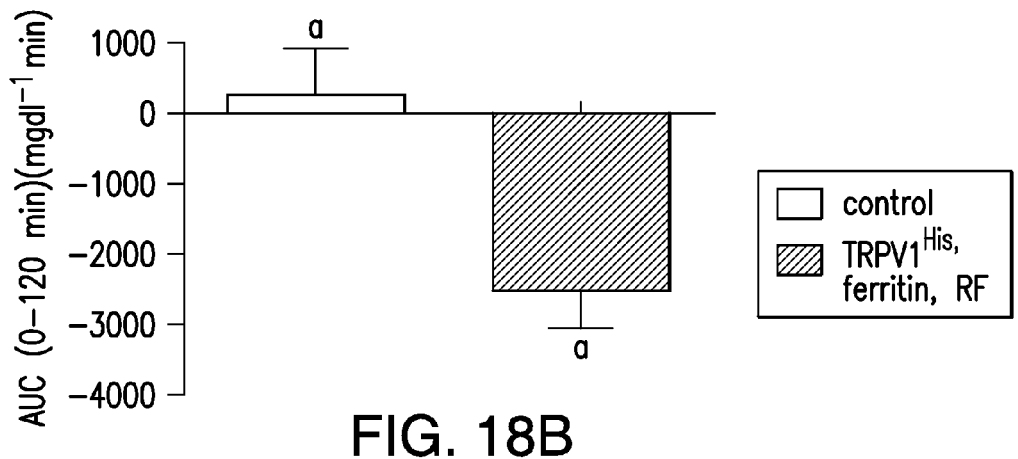

There are 4 forms of the ferritin complex that have been tested—ferritin light chain-linker-heavy chain (ferritin complex) expressing in the cytoplasm, ferritin complex expressed at the cell membrane, ferritin complex with egfp fusion that binds to TRPV1 with anti-gfp camelid antibody fusion and the system described above. FIG. 15 demonstrates proinsulin release from 293T cells transfected with calcium dependent insulin and either TRPV1/myristoylated ferritin, camelid anti-GFP fused to TRPV1/EGFP ferritin or camelid anti-GFP fused to TRPV1/EGFP ferritin/camelid anti-GFP fused to ferritin in response to RF treatment.

Example 3

NICE: Iron Oxide Nanoparticles

Iron oxide nanoparticles, functionalized with streptavidin to decorate the cells have been used for several reasons. Firstly, the streptavidin-biotin complex is the highest affinity non-covalent bond known and directs the nanoparticles stably to the cell surface. Secondly, the heat generated by nanoparticles in an RF field depends on both Brownian motion and Neel fluctuation, the internal rotation of the magnetic moment. When nanoparticles are bound to the cell surface, the proportion of heat generated by Brownian motion is significantly decreased. In contrast to other particles, such as cobalt ferrite nanoparticles, heat generated by iron oxide particles is primarily through Neel fluctuation rather than Brownian motion (Fortin et al., 2007 J. Am. Chem Soc. 129: 2628-2635). Thirdly, functionalized iron oxide nanoparticles are readily available in a number of sizes allowing the heating response to be tuned through field strength and frequency, and particle size. The size of particles that diffuse freely in a number of in vitro and in vivo settings has been defined and 20-30 nm beads have been found to be optimal.

Figure 22A:
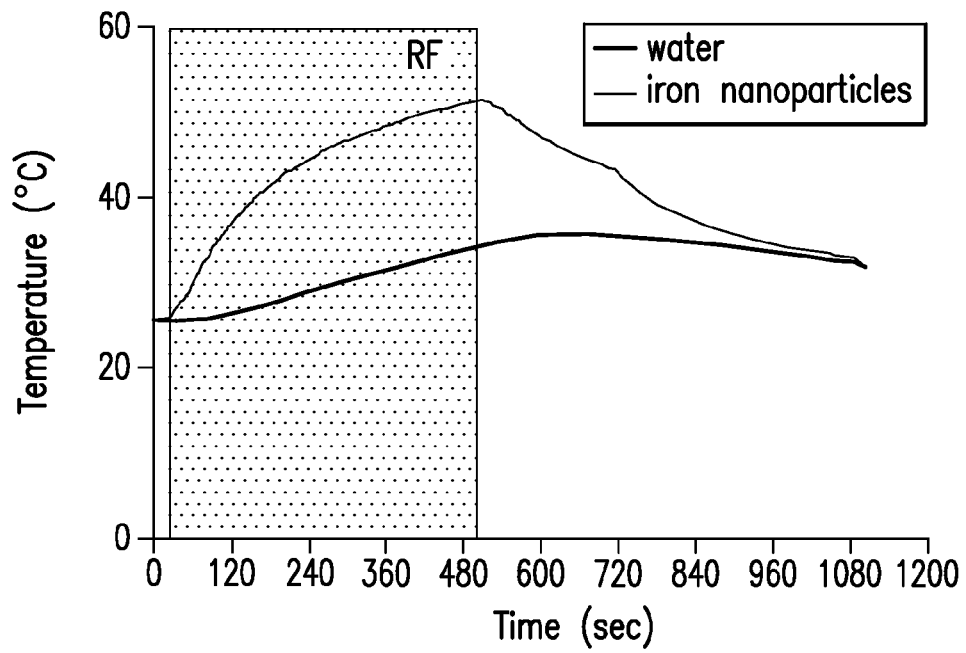
FIG. 22 shows heating of iron oxide nanoparticles in 465 kHz radiofrequency field. (A) Exposure of 20 nm ferrous oxide nanoparticle suspension (1 mg/ml) and water to 465 kHz radiofrequency field, (B) Significant increase in temperature of nanoparticles (compared to water). Nanoparticle temperature increases by 5° C. in 30 s without any increase in water temperature.
Figure 22B:
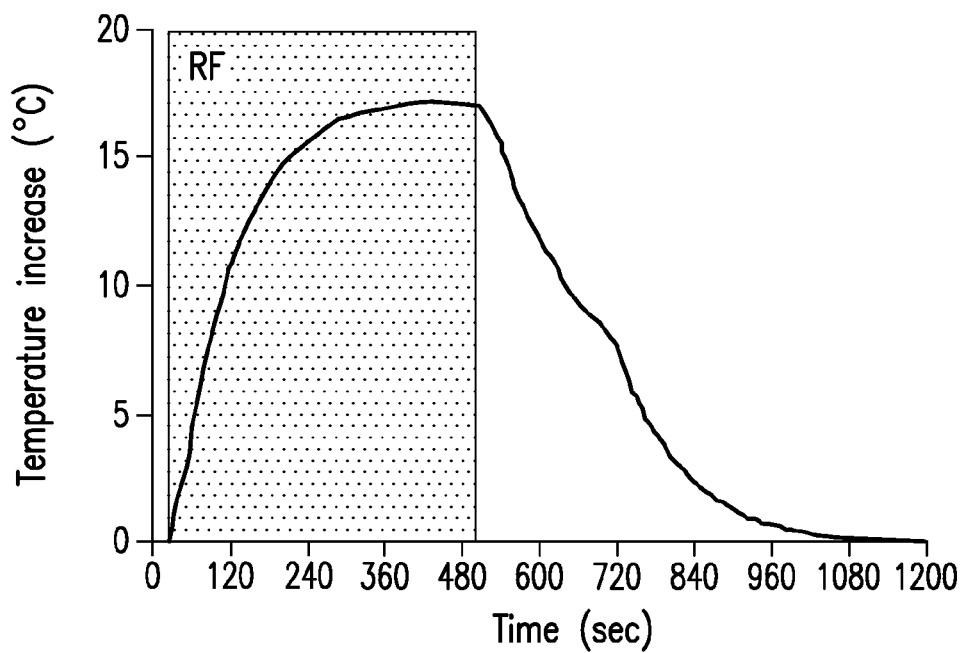

Using an alternating magnetic field (465 kHz, 110 kA/m) provided by a commercial induction generator (Ultraflex Power Technologies) and a custom-made, water cooled, induction coil (4.5 cm diameter), it has been demonstrated that the temperature of a suspension of iron oxide nanoparticles increases when it is exposed to the appropriate RF frequency. While much lower temperature increases are necessary for NICE in vitro or in vivo, an increase of up to 17° C. can be achieved when a suspension of 20 nm iron oxide particles (1 mg/ml) are exposed to a 465 kHz, 110 kA/m field (FIG. 22). It has been noted that a 5° C. rise in nanoparticle temperature is sufficient to open TRPV1 channels and can be reached in approximately 30 s with no increase in water temperature.

Figure 23A:
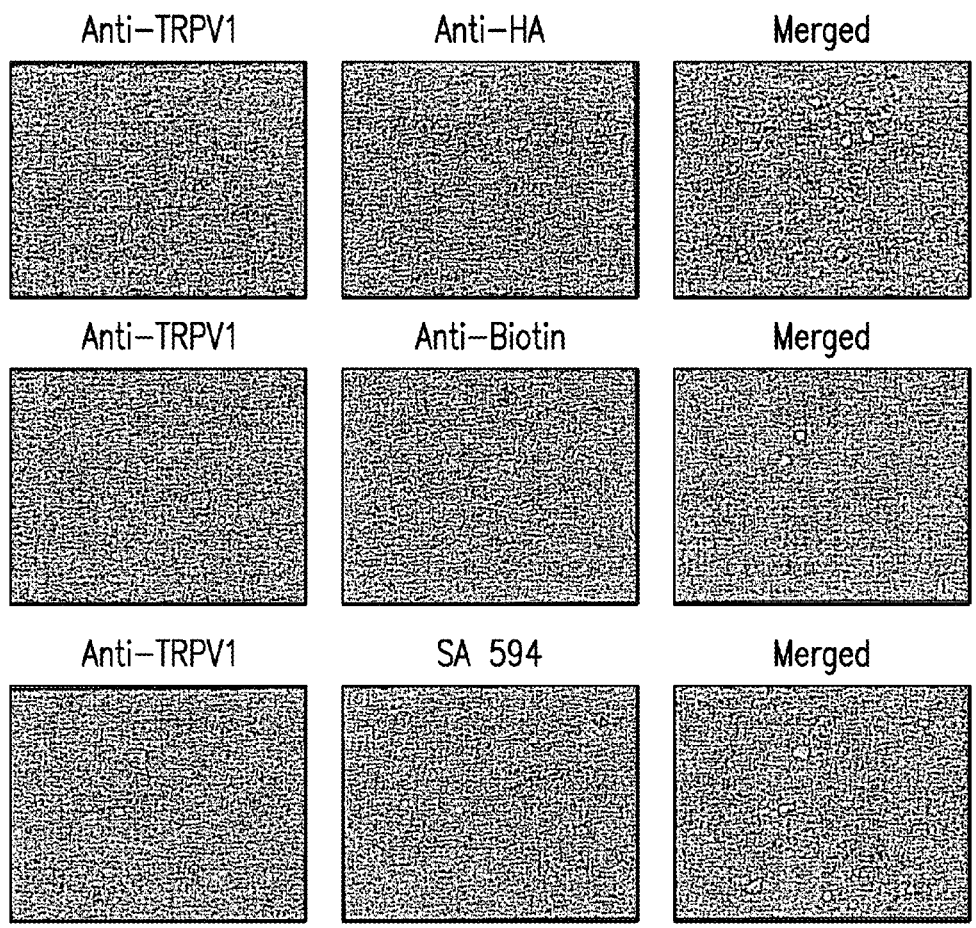
FIG. 23 shows confirmation of co-expression of TRPV1 and nanoparticle tether in vitro. (A) Dual staining for TRPV1 and HA (upper panels). TRPV1 and biotin (middle panels) and TRPV1 and streptavidin Alexa 594 (lower panels) in transfected HEK 293t cells. (B) Streptavidin coated iron oxide nanoparticle binding (10 nm) to transfected HEK 293t cells (left) and quantification in non-transfected and transfected cells (right).
Figure 23B:
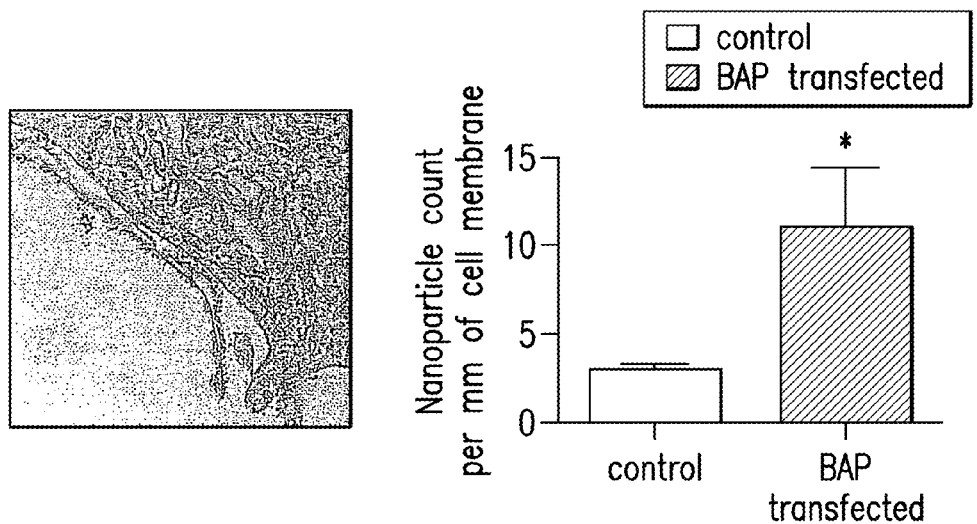
Figure 24A:
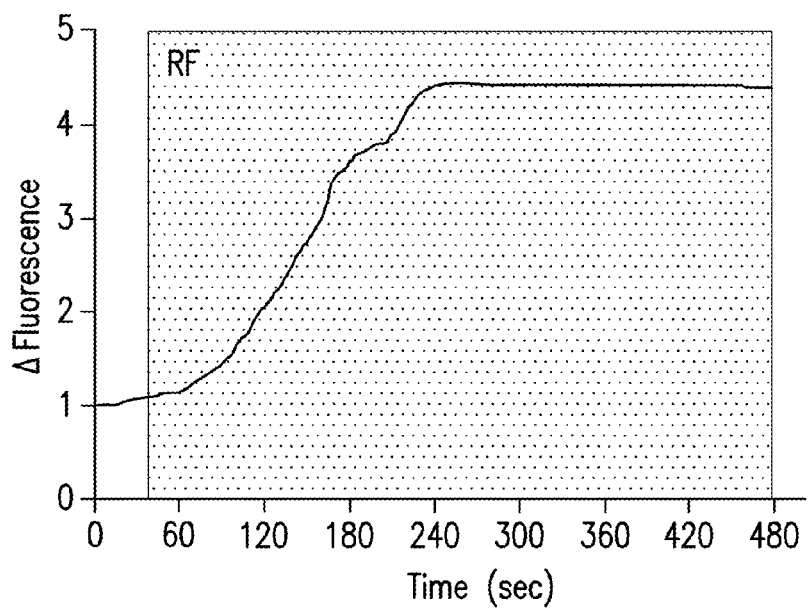
FIG. 24 shows opening of TRPV1 channels and calcium entry in response to nanoparticle heating by RF in vitro. (A) TRPV1 opening and rapid calcium entry in HEK293t cells transfected with TRPV1 and BAPTM and decorated with streptavidin coated nanoparticles in response to nanoparticle heating in RF field. Calcium entry was measured as a change in fluorescence intensity of the calcium indicator Fluo-4. (B) Pseudocolored images indicating change in fluorescence intensity in TRPV1 transfected cells with RF stimulation. (C) Indirect assessment of intracellular calcium via expression of luciferase under the control of a calcium dependent NFAT promoter. (D) Luciferase expression is significantly increased in HEK293t cells only in the presence of all components of the NICE system: TRPV1 and the biotin acceptor protein (BAP), the addition of 20 nm iron oxide nanoparticles (NP) and the presence of 465 kHz, 110 kA/m electromagnetic field (RF).
Figure 24B:
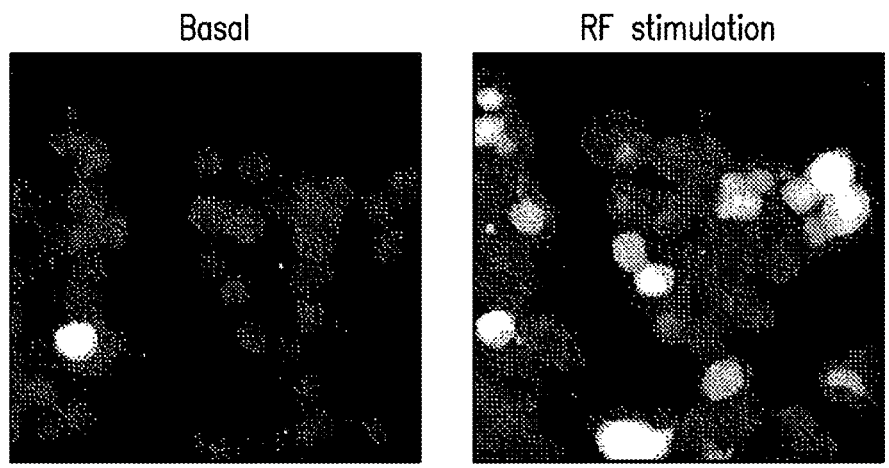
Figure 24C:
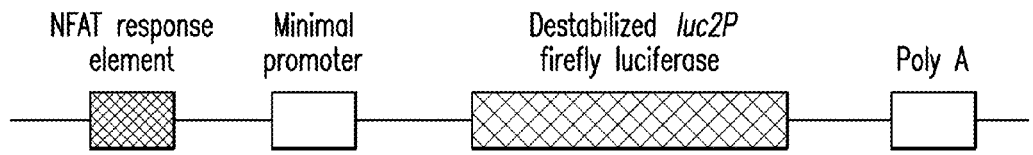
Figure 24D:
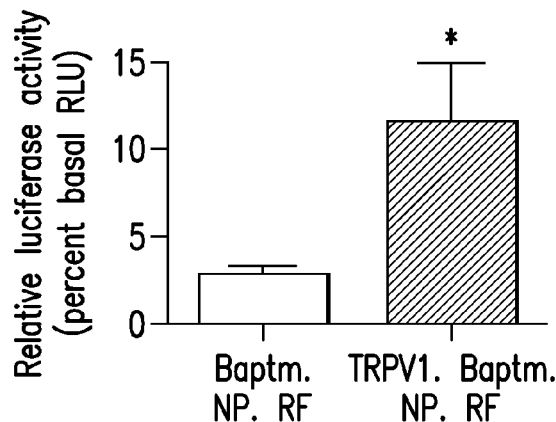

Iron oxide nanoparticles coated with streptavidin were used to decorate specific cell populations by expression of a tether in the form of a biotin acceptor protein (BAP) fused to the transmembrane domain of PDGFR and tagged with hemagglutinin (HA) (Tannous et al., 2006 Nat Methods 3:391-396) The biotin acceptor protein is modified by endogenous biotin ligase. The affinity of streptavidin and biotin is 10-15M and this high affinity has been shown by us to lead to specific binding of the nanoparticles only to cells that express the BAP tether. It has been shown that nanoparticles can decorate transfected HEK293t cells that express an HA tagged BAPTM fusion protein (FIG. 23). Electron microscopy confirms that streptavidin-coated ferrous oxide nanoparticles bind to the cell membrane and quantification reveals that this is significantly greater on cells transfected with the BAPTM fusion protein versus cells not expressing this construct. In addition, immunocytochemistry demonstrates significant co-localization of TRPV1 with HA (BAP) immunoreactivity, TRPV1 with biotin immunoreactivity, and TRPV1 with Alexa 594-streptavidin binding. These results confirm that constructs can drive co-expression of TRPV1 and the BAPTM fusion protein in the same cells (FIG. 23).

With NICE, the local temperature change achieved by heating nanoparticle-coated cells is transduced into calcium entry by targeted expression of TRPV1 channel. This is a single component channel that detects small changes in temperature just above the physiological range (>42° C.) as a result of a conformational change allowing calcium entry (Caterina et al., Nature 389:816-824). The response is proportional to the temperature change and relatively rapid, thus transducing temperature variations induced by the heated nanoparticles into a graded calcium current with attendant cell activation. Repeated heating also potentiates calcium entry, i.e., there is no desensitization. Generally, ion channels such as TRPV1 offer many advantages for modifying cell activity, including as described above, their fast temporal resolution and the ability to target their expression genetically without the tissue damage often seen with direct electrical stimulation. In this respect the activation of a temperature sensitive channel provides the same advantages as the reported light activated cation channel but without the need for an indwelling catheter, and with the potential, by using different nanoparticles, to effect activation of different cell types in response to different RF frequencies to modulate multiple cells in the same local region.

It has been confirmed that NICE can induce calcium entry in response to radio waves using streptavidin-coated iron oxide nanoparticles, expression of a cell surface biotin acceptor protein and the temperature sensitive TRPV1 channel in transfected HEK293t cells both with calcium imaging and a calcium sensitive NFAT-luciferase reporter construct as the readout (FIG. 24). The calcium response can be modulated both by the power of the RF field and by the exposure time.

These findings confirm the feasibility of the method in vitro. The methodology in vivo in vertebrates has been applied and validated. It is important to note that implementing the non-invasive, induction heating of nanoparticles in an RF field poses several technical challenges that have been addressed in the studies performed to date and that these will also need to be taken into account in in vivo studies. The RF field heats not only metallic/metal oxide nanoparticles but also the metal components of any structure within the field. Therefore, the apparatus to be used for imaging, recording and behavioral monitoring must be designed so as to remove any metal components and replace them with ones that are inert in an RF field. Nonetheless, the design and optimization of the custom equipment required to implement this technique is feasible.

In summary, a combination of nanoparticle heating in an RF field and a temperature responsive ion channel was used to convert localized temperature changes into remote, temporally controlled, and anatomically defined activation of specific cells. The NICE technology can further studied in vitro and in vivo using two classical physiological processes requiring specific calcium dependent functions: hormone release and neural activation. This technique can be applied in vivo to develop a novel method to regulate glucose metabolism and to examine the contribution of specific neural populations to feeding.

Example 4

Analysis of NICE In Vitro

The use of NICE in vitro can be extended as follows: (i) examining the cellular responses to nanoparticles over time, (ii) validating the ability of NICE to stimulate hormone release in vitro, (iii) modulating neural activity in vitro, in hippocampal neurons or (iv) dopaminergic neurons in brain slices and (v) examining the combinatorial activation of distinct cell populations using a novel combination of epitope-tagged TRPV1 channel and functionalized nanoparticles tuned to heat at distinct frequencies.

Cellular Responses to Nanoparticles and NICE.

Nanoparticles to be used in these studies will be prepared using well described methods and optimized to reduce non-specific binding by use of hydrophobic particles and functionalization with polyethylene glycol. Iron oxide nanoparticles will be synthesized using iron (III) acetylacetonate, reduced in the presence of oleylamine and oleic acid to yield monodispersed and single crystalline $Fe_3O_4$ nanoparticles with a high magnetic moment (Xu Zea 2009 Chem Mater 21:1778-1780 The resulting hydrophobic nanoparticles then are functionalized with carboxyl-terminated polyethylene glycol (PEG-COOH), which will further covalent attachment of targeted biomolecules (streptavidin or antibodies) through EDC/NHS chemistry and reduce non-specific uptake by cells (Xie Jea 2007 Adv Mater 19:3163-3166) Gold nanoparticles will be prepared by a seed-mediated growth synthesis (Sau T, Murphy C 2004 Langmuir 20:6414-6420, with the shaping surfactant hexadecyltrimethylammonium bromide replaced with thiolated PEG-COOH through an extensive aqueous-organic ligand exchange process. Wijaya A 2008 Langmuir 24:9966-9969). Ligand exchange will be confirmed through Fourier transform IR analysis and zeta potential measurements. Nanoparticle characterization will take place through transmission electron microscopy (TEM), dynamic light scattering, X-ray diffraction and, in the case of gold, surface plasmon resonance to ensure monodispersity and stability.

NICE utilizes cell surface tethering of nanoparticles for cell specificity and to provide proximity for TRPV1 channel activation. The fate of the nanoparticles after binding will be examined using both quantitative and qualitative tools by inductively coupled plasma mass spectrometer (ICP-MS) and microscopy, respectively. HEK 293t cells transfected with TRPV1 and BAPTM will be incubated with the nanoparticles and, at 5 min, 30 min, 2 h, 4 h, 12 h and 24 h the cells will be washed with Tween 20 to remove surface-attached nanoparticles. This supernatant as well as the homogenized cells will then be dissolved in aqua regia and analyzed using ICP-MS. These experiments will give a detailed time-course of nanoparticle uptake over time. Localization and integrity of the nanoparticles also will be investigated using TEM and confocal microscopy. Transfected HEK 293t cells will be incubated with nanoparticles and at various times (as above), cells will be fixed and embedded. Cell sections (50-70 nm) will be stained with uranyl acetate and TEM analysis will be used to identify the location of nanoparticles within the section, using the high contrast of electron dense iron and gold, as well as further identification with electron-dispersive spectroscopy (EDS). Confocal micrographs also can be used to determine the location of nanoparticles at the surface and within cells, using fluorescently labeled streptavidin conjugated to iron oxide particles or the dark-field light scattering of gold nanoparticles.

Initial studies indicate that NICE does not lead to apoptosis in NICE excited or non-transfected cells. However, more detailed studies of cell viability following nanoparticle binding and RF exposure will be conducted on HEK 293t cells transfected with TRPV1 and BAPTM, incubated with nanoparticles before and following RF excitation. Mitochondrial function will be examined using the standard MTT assay Absorbance will be read at 590 nm to quantify the mitochondrial reduction of yellow MTT to purple formazan. Membrane integrity following nanoparticle binding and RF exposure will be assessed by colorimetric measurement of lacatate dehydrogenase activity released from damaged cells. The effects of the NICE protocol on DNA damage also will be examined using an in situ apoptosis detection system Zoppi N et al. 2008 Biochim Biophys Acta 1783:1177-1188). Quantitative PCR (qPCR) will also be performed on RNA extracted from transfected HEK 293t cells, with and without RF exposure, for markers of the Unfolded Protein Response (including C/EBP homologous protein, phosphorylated inositol-requiring enzyme 1 alpha, eukaryotic initiation factor 2 alpha and activating transcription factor 3)(2-4)(2-4)(2-4)(2-4) need which are characteristic of ER stress Kyriakakis et al. 2010 Cell Signal 22:1308-1316; Winnay et al. 2010 Nat Med 16:438-445; Gjymishka A, et al. 2009 Biochem J 417: 695-703

The effects of nanoparticle uptake by cells on the ability to activate TRPV1 and induce calcium entry also will be examined. Cells transfected with TRPV1 and BAPTM will be incubated with nanoparticles for increasing lengths of time, based on the studies above, such that initial time points demonstrate minimal NP uptake while later time points can include cells with intracellular nanoparticles. Cells will be loaded with the calcium indicator, Fluo-4, and calcium entry in response to the RF field will be measured. Further studies will examine the effect of NICE on neighboring cells by preparing two populations of transfected cells, one expressing BAPTM and binding Alexa 350-streptavidin iron oxide nanoparticles and one expressing TRPV1 and the fluorescent marker, mCherry. These cell populations will be mixed and loaded with Fluo-4 before calcium imaging in the presence of the RF field. Absence of calcium entry in cells expressing TRPV1 and mCherry would indicate that heating of nanoparticles bound to one cell does not affect adjacent cell.

Effect of NICE on Hormone Release from Cultured Cells In Vitro.

Figure 25A:
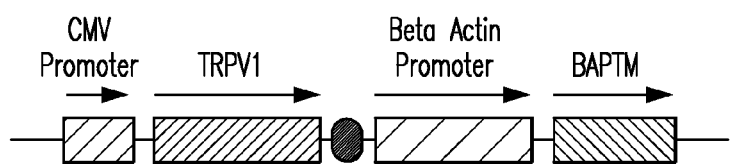
FIG. 25 shows constructs for viral delivery of NICE components and RF dependent hormone release. (A) Construct for constitutive expression of NICE components, BAPTM and TRPV1. (B) Construct for calcium dependent expression of furin modified human insulin. (C) Construct inserted into adenovirus for cre dependent expression of NICE components, BAPTM and TRPV1 using FLEX system. (D) 293t cells transiently transfected with TRPV1-Baptm and NFAT insulin show a significant increase in proinsulin release with nanoparticle binding and RF exposure. (E) Insulin gene expression is also significantly increased in these cells with RF exposure.
Figure 25B:
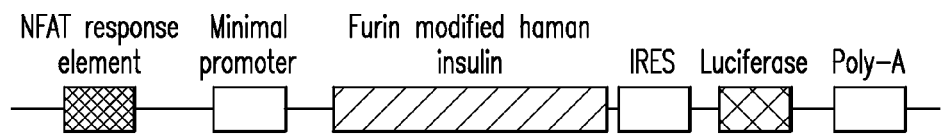

A classical calcium dependent process is hormone release from endocrine cells. The ability of NICE system to induce changes in hormone release in vitro using stably transfected cell lines has tested. Constitutive expression was achieved using a CMV promoter to drive TRPV1 channel expression and a beta actin promoter to drive BAPTM expression (FIG. 25A). Insulin expression will be controlled by the Ca2+ sensitive NFAT promoter as described herein. Expression of TRPV1 and BAP will be confirmed by immunocytochemistry (IHC). See FIG. 8.

The ability of NICE to modify endogenous insulin gene expression, synthesis and release will first be assessed using the RIN m5F insulinoma cell line expressing TRPV1-BAPTM in vitro. On the day of study, the stably transfected cells will be incubated in Kreb's phosphate buffer (KRB) containing streptavidin coated 20 nm iron oxide nanoparticles for 30 min. Nanoparticle decorated cells will be exposed to the 465 kHz RF field and the effects will be assessed after 5 min, 10 min, 30 min and 2 h, in part guided by the time course studies described above. Additional studies will examine the effect of repeated pulsed RF exposure for 5, 10 or 20 min periods for a total period of 2 h. These results will guide the RF intervals used for combinatorial studies. Calcium imaging will be used to determine the time course of calcium entry and calcium induced insulin release into the media will be measured by ELISA with insulin gene expression examined by qPCR. The effects of RF field strength and duration on insulin secretion will be examined. Control studies will examine the effect of TRPV1 and BAPTM expression on insulin secretion in the absence of RF stimulation and the effects of RF stimulation without addition of nanoparticles.

Calcium influx into cells can regulate gene expression via calcium dependent response elements. To assess the ability of NICE to modify gene expression, cells are engineered to express and release insulin in a Ca2+ dependant manner. As above, insulin is expressed downstream of a promoter with multiple Nuclear Factor of activated T-cell (NFAT) response elements and a minimal TATA promoter which has been shown to result in a significant increase in expression in response to raised intracellular calcium. This NFAT-TATA promoter is used to drive a bicistronic construct with modified human insulin and luciferase expression (FIG. 1). Processing of proinsulin to insulin relies on two beta-cell specific prohormone convertases, so a modified human proinsulin with engineered furin cleavage sites is used as this is processed to mature insulin in non beta-cells both in vitro and in vivo (Shifrin A L, et al. 2001 Gene Ther 8:1480-1489) its release can be differentiated from endogenous murine insulin release in vivo. This construct is stably transfected into PC12 cells already expressing TRPV1His to generate PC12-NICE-Ins cells. Studies demonstrate these cells secrete mature insulin. See FIG. 9.

The ability of NICE to induce insulin expression and release is studied. Cells are incubated with streptavidin iron oxide nanoparticles for the final 30 min of the preincubation period. The cells are then washed and placed in a 465 kHz RF field and the effects on insulin expression and release are examined by qPCR and ELISA, respectively. The effects of RF field strength and duration on gene expression and insulin release are examined and optimized. Studies in HEK 293T cells transiently transfected with TRPV1-BAPTM or TRPV1$^{HIS}$ and NFAT insulin confirm the ability of NICE to induce insulin gene expression and hormone release. See FIG. 8 and FIG. 6, respectively.

Effect of NICE on Electrically Excitable Cells In Vitro.

Calcium entry into electrically excitable cells induces depolarization and initiates action potentials. NICE will be used to regulate the activity of electrically excitable neurons in culture and in tissue slices in vitro. The ability of NICE to induce neural activity will be examined in primary hippocampal cell cultures. These cells will be infected with recombinant adenovirus expressing TRPV1-BAPTM constructs and then incubated with streptavidin-coated nanoparticles. Nanoparticle decorated cells will be exposed to the RF field and the effects assessed by calcium imaging and whole cell patch clamping. Preliminary studies indicate electrophysiological recording in the electromagnetic field is feasible. These studies will provide details of the intracellular calcium concentration achieved, the temporal resolution of the calcium entry in neurons, the degree of depolarization and spike activity achieved with NICE, and the effects of multiple RF exposures. Currents induced by RF activation will be measured while holding the neurons in voltage clamp. Membrane depolarization and spikes will be determined in current clamped neurons to determine the kinetics of activation and precision of control. Additional control experiments will examine the effect of TRPV1 and BAPTM expression on electrical properties of neurons in the absence of RF stimulation, the effects of RF stimulation without nanoparticle binding and to determine if there is a bystander effect in cells adjacent to those decorated with nanoparticles. In addition, the strength of the RF will be titrated to find the minimum field strength required for inducing an action potential.

Assays of the Effects of NICE in Brain Slices Ex Vivo.

Figure 25C:
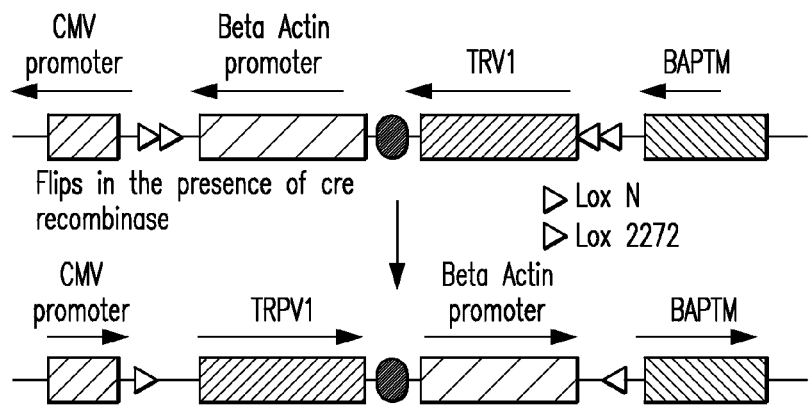
Figure 25E:
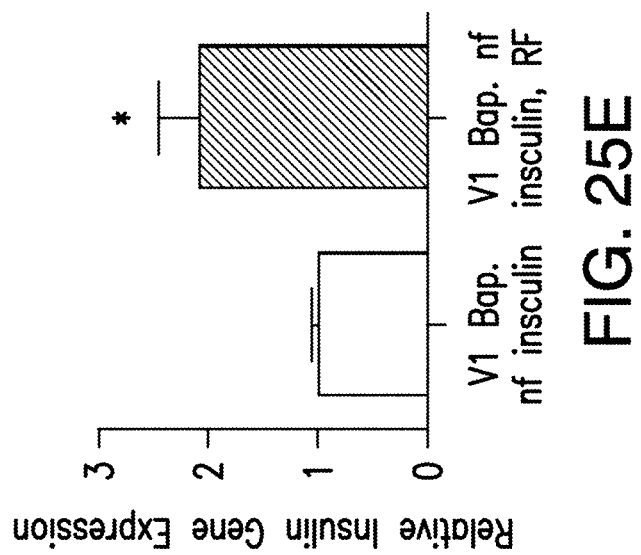
Figure 25D:
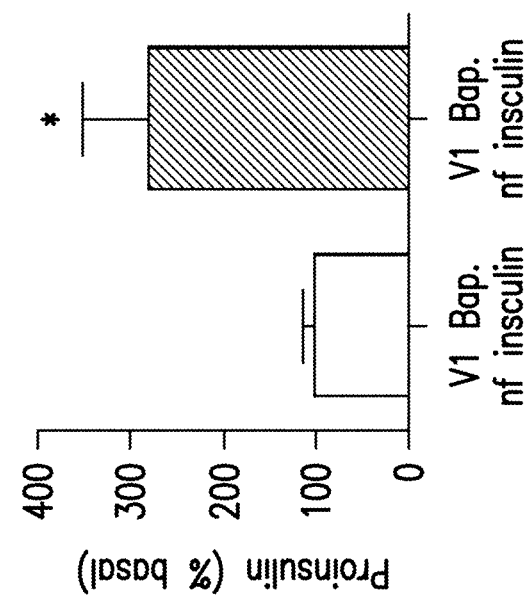
Figure 26B:
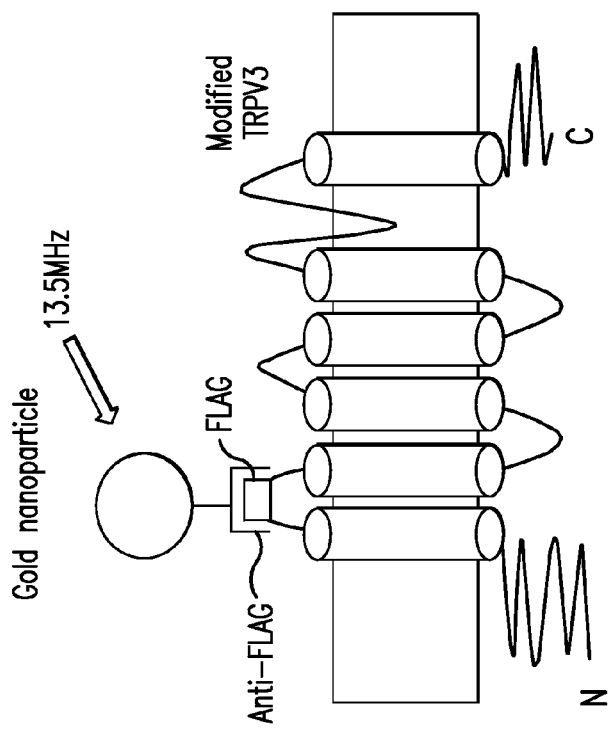
FIG. 26 shows combinatorial activation of transfected cells. A mixture of 2 cell populations will be studied each expressing a unique linear epitope in the first extracellular loop of TRPV1 to tether an antibody coated nanoparticle tuned to a distinct wavelength. Subsequent calcium entry increase expression of a calcium dependent luciferase unique to each cell population. (A) Iron oxide nanoparticles coated with anti-His 6× antibody bind to His 6 epitope in TRPV1. Calcium entry triggers CBR luc expression. (B) Gold nanoparticles coated with anti-FLAG antibody bind to FLAG epitope in TRPV1. Calcium entry triggers CBG99 luc expression.
Figure 26B:
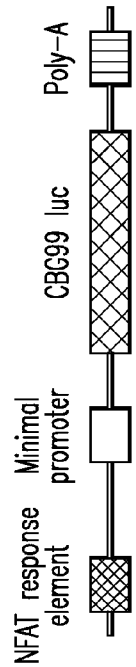
Figure 26A:
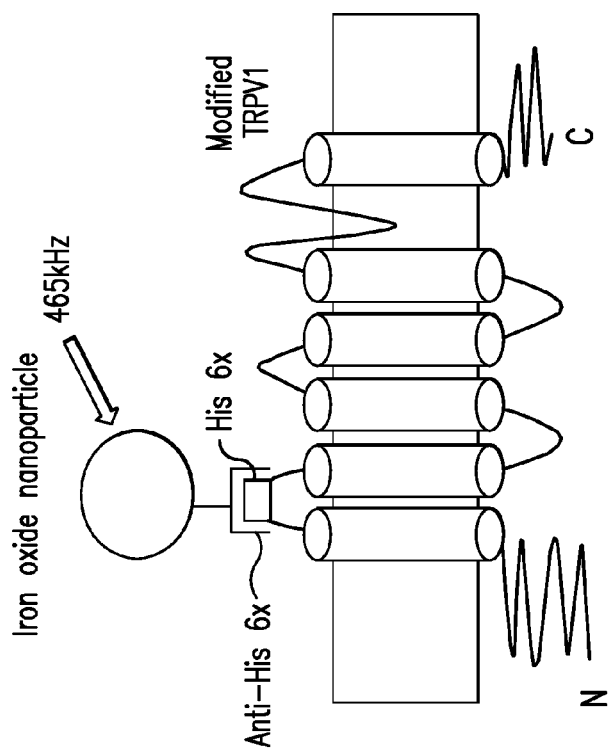
Figure 26A:
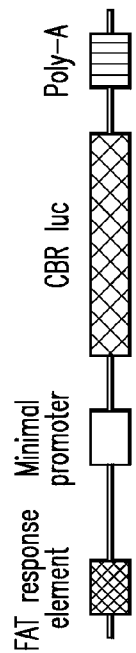

The ideal neuronal activation strategy provides anatomical specificity that, for the NICE system, would require expression of TRPV1 and BAPTM in a defined neural population. A recombinant adenovirus expressing a Flip-excision construct (Atasoy D, et al. 2008 J Neurosci 28:7025-7030) will be used to achieve cre-dependent expression of TRPV1 and BAPTM (Ad-FLEX-NICE) (FIG. 25C). In this construct, in the absence of cre recombinase, TRPV1 and the beta actin promoter will be in an inverted orientation and inactive. In the presence of cre, TRPV1 and the beta actin promoter return to the correct orientation and are locked in place by the excision of the additional lox site. This system will allow cell specific expression of the TRPV1 and BAPTM in cells that express cre with little or no expression in cells that do not express cre. Transgenic mice expressing cre recombinase in dopamine transporter neurons (DAT-cre) will be crossed to a reporter strain, ROSA26-lox-stop-lox-EYFP mice (Ekstrand M I, et al. 2007 Proc Natl Acad Sci USA 104:1325-1330) DAT-cre/YFP mice (age 4 weeks) will receive a stereotactic injection of high-titer Ad-FLEX-NICE stocks (~150 nl of stock of 108 infectious units) into the ventral tegmental area (VTA). In a subset of animals, expression of the construct will be determined by triple IHC to confirm co-localization of YFP (expressed solely in cre neurons), TRPV1 and Alexa-streptavidin binding. Wild-type mice also will be injected to ensure there is no expression of the cre dependent construct in the absence of cre recombinase. Ten to 14 days after viral delivery, mice will be sacrificed and sections (200 μm) will be cut. After resting, slices will be incubated with streptavidin-coated iron oxide nanoparticles for 30 min. The electrophysiological properties of infected, decorated neurons will be determined by patch clamp recording in the absence and presence of RF stimulation. Overall, these studies will confirm the ability of NICE to stimulate Ca2+ influx and neural activity in neural slices in vitro.

Combinatorial Activation of Specific Cellular Populations.

The NICE system will be refined further to allow combinatorial activation of specific multiple cell populations, even if they are interspersed, using epitope tagged TRPV1 channels. Nanoparticles of different compositions and shapes heat at different EM power and frequency with different rates. For example, iron oxide nanoparticles are heated by a frequency of 465 kHz which does not heat gold, whilst gold nanoparticles heat rapidly at a frequency of 13.5 MHz. Furthermore the response characteristics of the particles also are influenced by their size. Thus, gold could be activated at a much lower RF field strength than iron oxide (i.e., gold heating faster than iron oxide) (Saleh S. et al. J. Biomedical Science and Engineering, 2008, 1, 182-189) Hence, even in the presence of both gold and iron oxide nanoparticles it is possible to selectively activate gold. Uniquely modifying TRPV1 channels expressed under the control of cell-specific promoters, provide distinct cell surface tags to direct nanoparticle binding. Particles can be specifically targeted to different cell types by coating them with recombinant antibodies directed against short epitopes. This can allow differential regulation of distinct cell populations in the same anatomical region. Specific antibodies recognizing a library of short linear epitopes that have been identified using phage display will be used. These epitopes will be inserted in frame into the first extracellular loop of TRPV1 which has been shown can be modified without altering the response characteristics of this channel.

Two different nanoparticles will be targeted: iron oxide (465 kHz) and gold nanoparticles (13.5 MHz) (Moran C, et al. 2009 Nano Research 2:400-405) to two different cell populations (FIG. 26). Carboxyl-terminated nanoparticles will be functionalized with recombinant single chain Fv antibody fragments (scFv) (Vigor K L et al. 2009 Biomaterials) to the specific short linear epitopes, His6× (6aa) and FLAG (8aa). Constructs will be generated in which these epitopes are introduced into the 1st extracellular loop of the TRPV1 channel. As mentioned above, it has been shown that this does not interfere with the temperature sensing properties of the channel. Each construct will be transfected into HEK 293t cells and paired with a distinct NFAT-RE driven luciferase reporter (CBRluc—red luciferase, CBG99luc—green luciferase) to give two different reporter read-outs of calcium entry for each cell type. Post-transfection, the two cell lines will be mixed and cultured together for a further 48 h before incubating in serum free medium overnight. On the day of study, the cells will be incubated with a cocktail of two nanoparticles; iron oxide functionalized with anti-His6× and gold nanoparticles functionalized with anti-FLAG. The localization of different particles to different cells will be confirmed using IHC. The cells will then be exposed to sequential pulses (5 min, 10 min or 20 min) of RF frequencies of 465 kHz and 13.5 MHz using a variable frequency amplifier for a total of 40 minutes at each frequency before the cells are lysed and individual luciferase activity measured.

These studies will make use of existing nanoparticle technology but nanoparticles of differing chemistries (e.g., iron oxide and gold), size (5-50 nm), and shape (spheres, rods) also will be developed to produce a range of distinct RF excitation profiles and power-heating profiles to improve this combinatorial approach. These in vitro studies provide evidence that the technology is able to activate ensembles of two or more different classes of cells or neurons alone or in combination even if these cells are colocalized in a small anatomical region.

Example 4

In Vivo Studies of NICE on Hormone Release

The goal of an artificial endocrine organ has yet to be achieved but the ability to remotely control hormone expression and release can provide a significant advance towards this aim. Once the effects of NICE on insulin synthesis and release have been optimized in vitro, in vivo studies to examine the effects of NICE on insulin release will be carried out.

The power required to create an RF field increases with the square of the coil diameter and thus a significantly more powerful generator (50-75 kW) will be required for these in vivo studies as compared to those required in vitro. Generators with sufficient power are readily commercially available (Ultraflex Power Technologies, NY). The size of the behavioral chamber will be kept to a minimum to reduce the power required whilst ensuring the mouse is able to move freely. Studies will focus on the design of both the coil and the plexiglass chamber used for assessment to ensure a uniform RF field is achieved. Modifications of the coil and generator will be made pending the results of these studies.

Effect of NICE on Insulin Expression in Implanted Cells In Vivo.

Initial studies will examine the ability of NICE to regulate calcium dependent modified insulin expression in vivo as an indication of whether NICE can be employed to regulate gene expression and hormone release. Stably transfected PC12-NICE-Ins cells expressing TRPV1, BAPTM, and NFAT driven modified insulin will be used since these cells can synthesize and secrete insulin and are capable of forming subcutaneous tumors in immunodeficient mice (Fritz M D et al. 2006 Exp Cell Res 312:3287-3297). These stably transfected cells will be injected subcutaneously into nude mice to create tumors expressing TRPV1, BAPTM, and NFAT-insulin IRES luciferase constructs. This will be confirmed by IHC. Freely diffusable iron oxide nanoparticles (20 nm) or vehicle will be injected into the tumor and the effects of RF stimulation on blood glucose and insulin, and glucose tolerance will be examined. Insulin expression will be determined by qPCR of tumor RNA in a subset of mice. Luciferase expression, as an indicator of calcium entry, in tumors will be confirmed by luminometer studies in vivo (Birsoy K. et al., 2008 Proc Natl Acad Sci USA 105:12985-12990). Further studies will focus on the effect of stimulating PC12-NICE-Ins cells on glycemic control and glucose tolerance in streptozocin-treated diabetic nude mice. Initial studies, based on in vitro studies described above, will optimize the time period of RF exposure, by examining these measures after 5, 10, 20 or 40 mins of RF exposure. Insulin and glucose levels will be measured immediately following RF stimulation and at 10 min, 30 min, 1 h and 2 h thereafter to follow the time course of the insulin response to stimulation. In this, and all in vivo studies, a number of mice will be examined in detail postmortem for pathological changes that may be associated with nanoparticle administration or RF exposure.

Effect of NICE on Endogenous Insulin Release In Vivo.

Figure 27A:
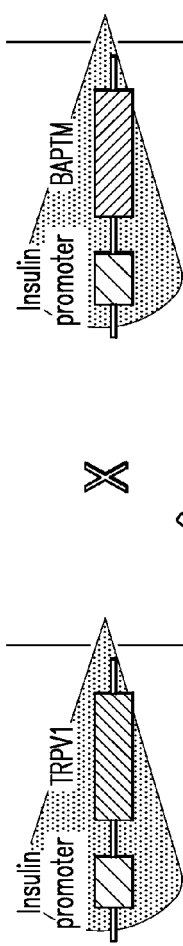
FIG. 27 shows constructs for generation of transgenic mice for expression of NICE components. Transgenic mice will be generated with the insulin promoter driving expression of TRPV1 (A) and BAPTM (B). These mice are crossed to express both TRPV1 and BAPTM in beta cells (C). An additional transgenic mouse with luciferase downstream of NFAT response elements will act as an in vivo reporter of intracellular calcium (D). The resulting mice (E) will express TRPV1 and BAPTM in beta cells and calcium dependent luciferase in all cells.
Figure 27B:
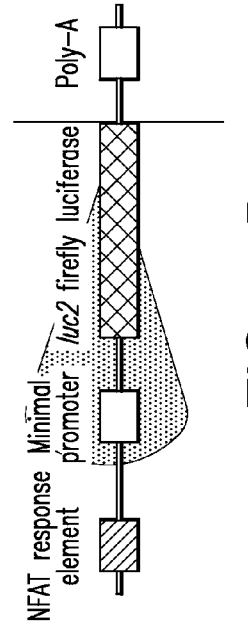
Figure 27C:
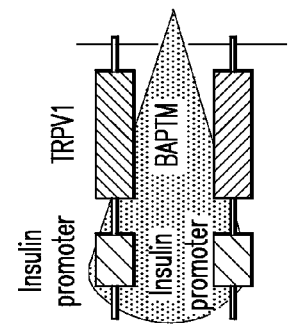
Figure 27D:
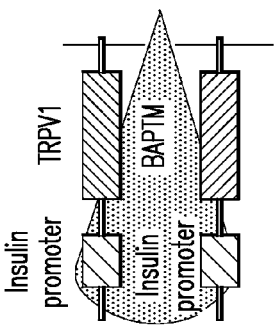
Figure 27E:
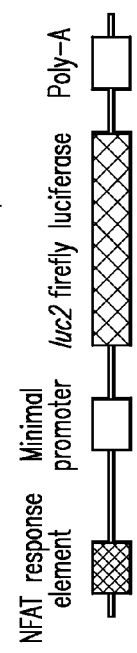
Figure 28B:
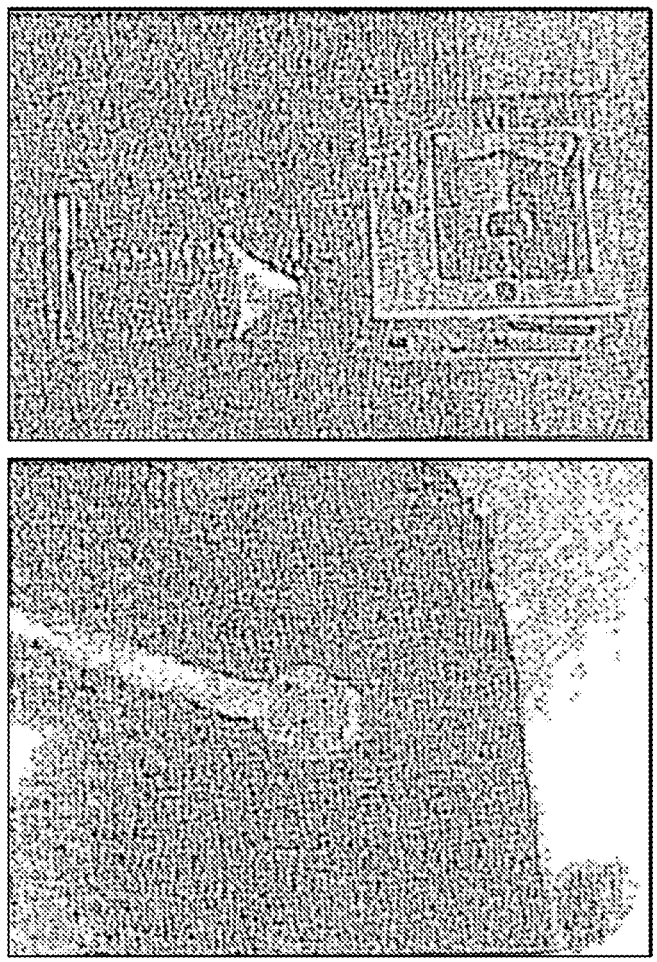
FIG. 28 shows an illustrative scheme for self-stimulation protocol with lickometer: (A) a fiber connector for implant of a biocompatible 200 μm fiber optic; (B) implanted fiber to deliver light to the ventral tegmental area; (C) Med associates photobeam lickometer; (D) the self-stimo-lick paradigm is a variation of the self-stimulation paradigm where the operant behavior is a lick. Light stimulation of ChR2 positive neurons or RF stimulation of NICE positive neurons occurs only when the mouse consumes water from the lickometer; (E) animals injected with AAV-Flex-hChR2-mCherry virus (top) consume more water than controls (bottom) form the connected port. (F) cumulative licks over a 2 hour trial. Light sensitive (red) and control animals (blue) in a SSL paradigm.
Figure 28A:
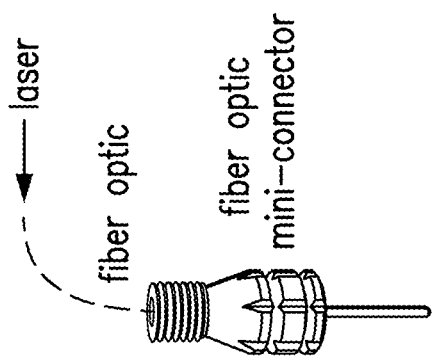
Figure 28C:
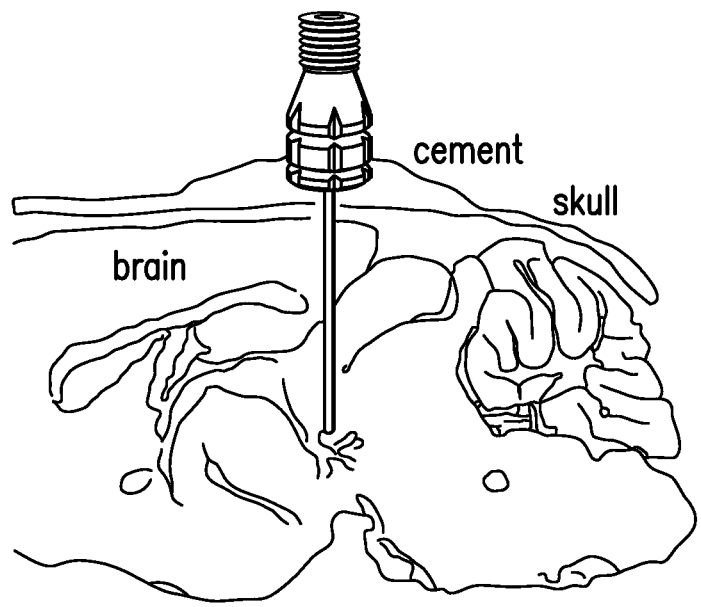
Figure 28D:
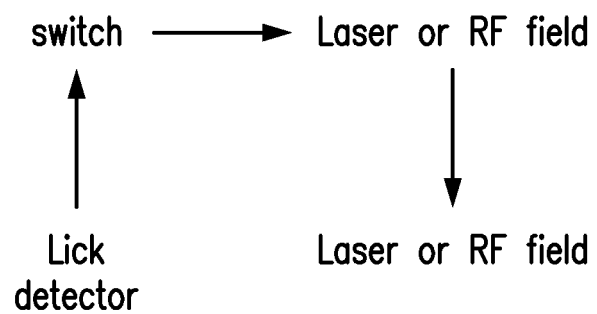
Figure 28E:
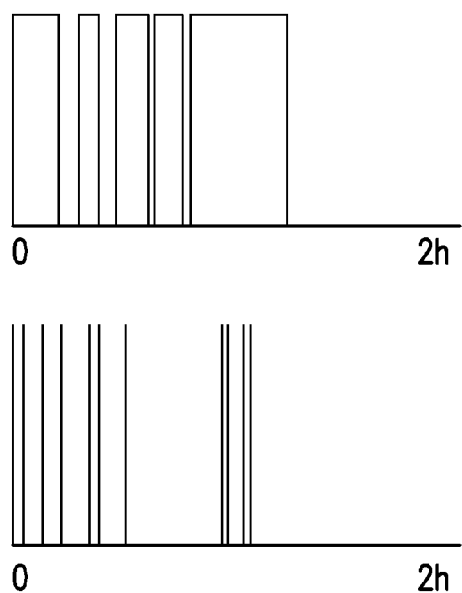
Figure 28F:
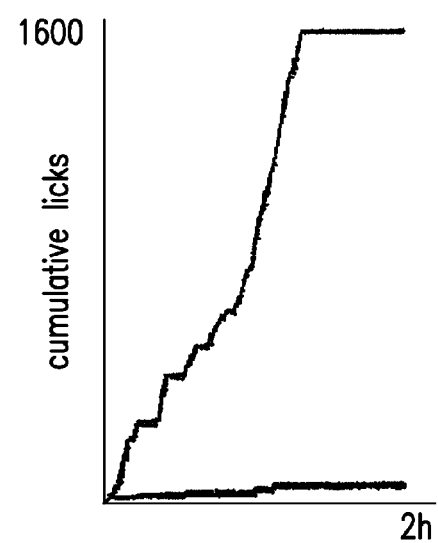

For studies examining the effect of NICE on endogenous insulin release, transgenic mice will be used to express the NICE components. Two transgenic mouse lines will be generated to overcome the lower expression of the second gene after an IRES. The first will use an insulin promoter to drive TRPV1 expression (FIG. 27A) and the second will use the insulin promoter upstream of BAPTM (FIG. 27B). These mice will be crossed resulting in TRPV1 and BAPTM expression exclusively in beta cells (FIG. 27C). In addition, a further cross to a reporter mouse expressing luciferase downstream of NFAT response elements and a minimal promoter results in co-expression of calcium dependent luciferase (FIGS. 27D and E). Immunohistochemistry will be used to confirm TRPV1 and BAPTM expression in beta cells.

These studies aim to address whether NICE can be employed to regulate endogenous insulin release in vivo without the necessity of injecting cultured cells. At 8-10 weeks, transgenic mice will receive pancreatic injections of iron oxide nanoparticles or vehicle. Nanoparticle binding to beta cells will be confirmed using double IHC for insulin and streptavidin. It has been established that the 20 nm particles that will be used can freely diffuse in tissues. Once the optimal time for particle binding to the cells has been determined, the effect of RF field stimulation on blood glucose and insulin will be examined. A luminometer will be used to examine the luciferase response to RF stimulation in vivo as previously shown by us. The effects of RF field power and duration on these parameters will be studied at various times (see above). When these parameters have been optimized, mice also will undergo glucose tolerance testing in the presence or absence of RF stimulation. Pending these results, these studies will be repeated on control and InsTRPV1-BAPTM mice treated with streptozocin (a model of insulin deficient diabetes), high fat diet (a model of insulin resistant diabetes) or transgenic mice crossed to leptin deficient, glucose intolerant, ob/ob mice.

Combinatorial Activation of Nanoparticles to Regulate Glucose Metabolism In Vivo.

Combinatorial activation of nanoparticles can be applied to develop a system whereby circulating glucose can be modulated through the release of either insulin or glucagon. PC12 are stably transfected to give two populations, the first expressing TRPV1 modified with a His6× tag and NFAT driven insulin expression (PC12-TRPV1His-Ins) and the second expressing TRPV1 modified with a FLAG tag and NFAT driven glucagon expression (PC12-TRPV1FLAG-Glucagon). A combination of the two cell lines are then injected subcutaneously into nude mice to give a tumor with a mixed cell population of both PC12-TRPV1His-Ins and PC12-TRPV1FLAG-Glucagon which can be confirmed by IHC for His and Flag epitopes. The tumor is then injected with a cocktail of iron oxide nanoparticles functionalized with anti-His6× antibody and gold nanoparticles functionalized with anti-FLAG antibody. RF stimulation at 465 kHz should heat iron oxide nanoparticles and stimulate PC12-TRPV1His-Ins cells to synthesize and release insulin reducing plasma glucose since gold nanoparticles are not heated at this lower frequency. RF stimulation at 13.5 MHz preferentially heats gold nanoparticles targeted to activate PC12-TRPV1flag-Glucagon cells to release glucagon and increase plasma glucose. Finally, alternating 10 minute pulses of RF frequencies of 465 kHz and 13.5 MHz using a variable frequency amplifier will be used to stimulate the release of both glucagon and insulin to modulated plasma glucose. These studies allow one to confirm that NICE can be used to activate different cell types alone or in combination. These studies allow one to remotely up regulate or down regulate blood glucose upon which future development of artificial endocrine organs may build on. See FIG. 10 for demonstration of in vivo regulation of insulin expression.

Example 5

Effects of NICE on Neural Activity In Vivo

Following optimization of NICE on neural activity in vitro, its efficacy in mice in vivo will be confirmed. To this end, the utility of NICE will be demonstrated by studying a well-characterized neural network and behavior; the dopamine reward pathway using a self-stimulation paradigm and compare its actions to those of an invasive neural stimulation protocol using channelrhodopsin and blue light. The use of channelrhodopsin has been validated to induce reward behavior, see below, and this system will be used to compare the ability of the NICE protocol to induce this same behavior.

Self Stimulation Protocol Using Channelrhodopsin.

In traditional self-stimulation protocols, rodents are trained to associate lever pressing with delivery of an electrical stimulus into a specific brain region. The behavioral chamber consists of a choice between two levers, one lever results in direct brain stimulation while the other has no effect. A decreased latency to lever press and increased frequency of lever presses indicates stimulation of the brain region is rewarding to the animal. Using such a protocol, it has been demonstrated that stimulation of the ventral tegmental area (VTA), rich in dopamine neurons, is rewarding (Fibiger H C, 1987 J Neurosci 7:3888-3896; Druhan J P, Fibiger H C, Phillips A G 1990 Behav Brain Res 38:175-184)(8, 9)(8, 9)

Recently, a modified version of this self stimulation protocol has been validated using a lickometer to trigger light dependent opening of channelrhodopsin and thus specific activation of dopaminergic neurons. The lickometer places a sipper tube behind a ">" shaped plate such that the mouse is forced to lick for water delivery. An infrared beam placed between the plate and the sipper counts each beam break by the tongue as the animal licks for water. In these studies, the operant behavior is consumption of water from the lickometer under conditions where the mice have a choice between one lickometer port which has no effect, and a second port which results in light delivery activating VTA neurons that express ChR in dopamine transporter (DAT) cre cells. This system confers anatomical specificity by expressing the effector, channelrhodopsin (ChR2), only in a defined neural population i.e.; the dopaminergic neurons expressing a DAT-cre construct expressed in these neurons. The scheme for this experiment is shown in FIG. 28. In studies using this system, mice with dopamine neuron specific expression of ChR2 show a significant increase in consumption from the light-activating lickometer port (FIG. 28). This paradigm provides a means for comparing the robustness of light vs. RF for neural activation of this reward behavior.

Self Stimulation Protocol Using NICE.

The effects of NICE on dopamine neuron excitation will be directly compared with those already achieved by optogenetic stimulation mediated by channelrhodopsin (ChR2). In this manner, a baseline stimulation is provided that is achieved currently using invasive light activation and allows one to assess the efficacy of RF stimulation. Stereotactic injection of Ad-FLEX-NICE or AAV-FLEX-ChR2 encoding cre-dependent constructs into the VTA of DAT-cre mice will be used to drive specific expression of NICE constructs (TRPV1 and BAPTM), ChR2-mCherry or mCherry alone (control) in the dopamine neurons of DAT cre mice.

Ten days after virus injection, ChR2 injected and control mice will be implanted with a fiber optic system to deliver blue light (473 nm wavelength) to the VTA and allowed to recover prior to training NICE mice and a second group of control mice will receive a VTA injection of streptavidin-coated iron oxide nanoparticles. The location of the nanoparticle injection will be confirmed by MRI, which can be used to precisely localize the beads. The distribution of particles on dopaminergic neurons will also be analyzed using double IHC for streptavidin and dopamine.

Following acclimation to the behavioral equipment (Med Associates), mice will be given three daily 60 min training sessions to establish the association between one of two lickometers (L-A or L-B; counterbalanced) and intracranial stimulation either via a pulse of blue light (ChR2) or a pulse of RF field (NICE). For half the animals, L-A will be rewarded and L-B unrewarded and for half, L-B will be rewarded and L-A unrewarded. Consumption from the lickometer at each training session and at testing will be recorded by the infrared monitoring system. Having acquired the association between the lickometer and delivery of light or RF field, retrieval will be tested 2 days after training The latency to consumption and the number and pattern of licks will be recorded over a 2 h trial period. A decreased latency and increased frequency to lick at the port associated with RF delivery would suggest that NICE is capable of activating DAT cre neurons to modify reward behavior. At the end of the study, mice will be sacrificed and specific expression of TRPV1-BAPTM (anti-TRPV1, anti-tyrosine hydroxylase (TH) and Alexa-streptavidin) or ChR2 (mcherry, anti-TH) in the DAT neurons confirmed by immunohistochemistry.

As with in vitro studies, the RF field will heat metal and therefore the behavioral equipment must be free of all metal components. This will be achieved by using a custom-built plexiglass chamber with glass sippers and fiber optical cabling delivering information from the infrared beam break system. A video system mounted above the RF field will monitor movement in the chamber. The chamber will be encircled by a custom-made coil sufficient to provide a uniform RF field throughout the chamber and to a height equivalent to that of a rearing mouse.

Overall, this set of studies will confirm that RF field stimulation is effective at neural stimulation to modify behavior in vivo in vertebrates. It also will allow comparisons of the ability of NICE to activate dopamine neurons for self-stimulation in comparison to light stimulation via ChR2. Additional studies may be performed to optimize the field strength and duration of the individual stimulus delivered with each response and thereby create response-field strength curves and response-duration curves. These studies will allow optimization of the NICE system in vivo in a well-defined paradigm alongside existing stimulation tools.

Combinatorial Activation of Nanoparticles to Study Feeding Behavior In Vivo.

The use of NICE is most advantageous for the study of complex behaviors where intracranial implants and tethering to deliver light or electrical stimuli may subtly alter or hinder behavior. One such behavior is feeding, which is particularly susceptible to interference such that even relatively low levels of stress may alter feeding patterns (Abbott C R et al. 2006 Int J Obes (Lond) 30:288-292). The hypothalamus regulates feeding to maintain body weight in a narrow range while hedonistic systems, particularly dopamine reward pathways and cortical regions, modulate and may even over-ride this (Davidson T L 1993 Psychol Rev 100:640-657). The hypothalamic arcuate nucleus is known to be a key component of hypothalamic feeding circuitry. The arcuate contains two primary cell populations expressing the leptin receptor, one co-expressing neuropeptide Y (NPY) and agouti related peptide (Agrp) and the second co-expressing the gene pro-opiomelanocortin (POMC) whose major product is alpha melatonin stimulating hormone ($\alpha$-MSH) (Cone R D, 2001 Int J Obes Relat Metab Disord 25 Suppl 5:S63-S67) Central and arcuate Agrp injection potently stimulates feeding, knock-down in Agrp expression reduces body weight and post-natal loss of Agrp neurons reduces food intake and body weight (Bewick G A et al. 2005 FASEB J 19:1680-168; Gropp et al. 2005 Nat Neurosci 8:1289-1291; Rossi M. et al. 1998 Endocrinology 139:4428-4431; Makimura H. et al. 2002 BMC Neurosci 3:18). Conversely, central administration of $\alpha$-MSH inhibits feeding and mice lacking the MC4 receptor, at which $\alpha$-MSH is an agonist are hyperphagic and obese (Shimizu H, et al. 1989 Life Sci 45:543-552; Huszar D. et al. 1997 Cell 88:131-141). However, these neurons also express classical neurotransmitters and other neuropeptides whose effects may not be reflected in the pharmacological approaches of intracranial peptide delivery or peptide overexpression. Further, the relative dominance of these neural populations on feeding is unknown for example, whether stimulation of Agrp neurons outweighs the effect of stimulating POMC neurons or vice versa. Until now, the technology has not been available to acutely stimulate defined cell populations and examine the consequences in freely moving animals. Therefore, NICE will be used to selectively stimulate these important neuronal populations in vivo, either individually or together, to examine their physiological roles in feeding.

Figures 29A, 29B, 29C:
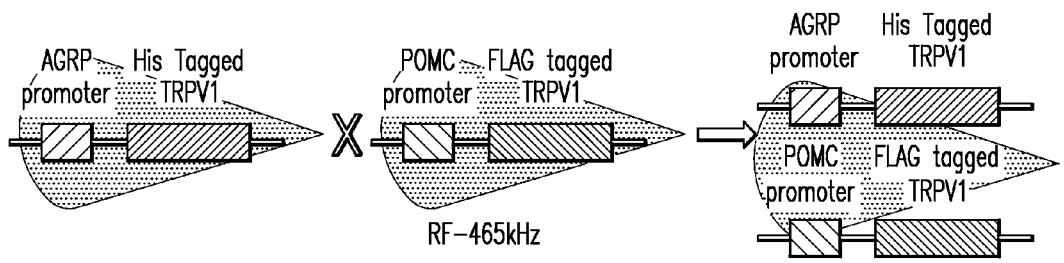
FIG. 29 shows expression of NICE constructs in Agrp and POMC neurons. (A) generation of BAC transgenic mouse with His tagged TRPV1 under the control of Agrp promoter; (B) transgenic mouse with Flag-tagged TRPV1 under control of POMC promoter; (C) these transgenic lines are crossed to result in mice with His tagged TRPV1 expression in Agrp neurons and Flag tagged TRPV1 expression in POMC neurons of the arcuate nucleus; (D) without RF stimulation neither AGrp nor POMC neurons are activated; (E) in the presence of anti-His iron oxide beads and RF of 465 kHz, His-tagged Agrp neurons are activated; (F) in the presence of anti-FLAG gold nanorods and RF of 13.5 MHz, FLAG tagged POMC neurons are activated; (G) with both anti-His iron oxide beads and anti-FLAG gold nanorods and RF of 13.5 MHz, both His tagged Agrp neurons and FLAG tagged POMC neurons are activated.

BAC transgenesis will be used to generate mice expressing epitope-tagged TRPV1 channels directly under the control of the Agrp promoter (His tagged) or the POMC promoter (FLAG tagged) (FIG. 11) (Gong S et al. 2002 Genome Res 12:1992-1998). When these mice are crossed, dual transgenic progeny expressing Agrp-Trpv1His and POMC-Trpv1FLAG will be generated (FIG. 29C). Specific expression will be confirmed by dual IHC for His/Agrp and FLAG/$\alpha$-MSH. Mice will receive a stereotactic injection into the arcuate nucleus of a mixture of anti-His coated iron oxide nanoparticles and anti-Flag gold nanoparticles. These will bind specifically to Agrp neurons and POMC neurons respectively. The effects of neural stimulation on food intake will be determined in a custom built, metal-free metabolic chamber (Columbus Systems). A coil surrounding the chamber will generate a variable RF field and the pattern, frequency and total food intake will be examined along with feeding related behaviors such as activity.

Figures 29D, 29E:
Figures 29F, 29G:
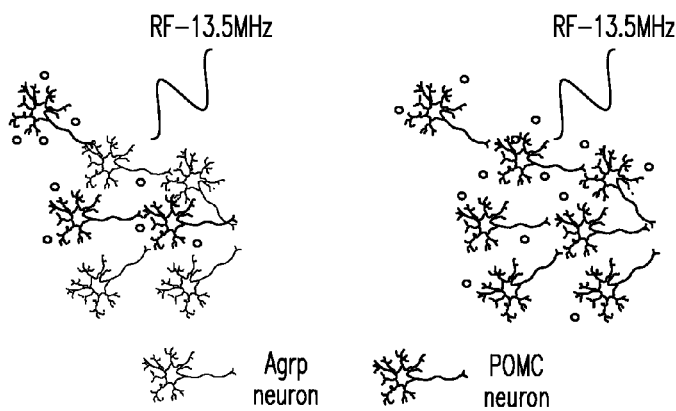

First, feeding behavior in response to stimulation of individual neural populations will be examined. The effects of Agrp neuron stimulation will be examined in the presence of RF field stimulation at 465 kHz to heat iron oxide particles (FIG. 29E). The effects of POMC neuron stimulation will be with RF stimulation at 13.5 MHz which selectively heats gold nanoparticles (FIG. 29F). Finally, combinatorial stimulation will be achieved by pulsed alternating RF stimulation at 465 kHz and 13.5 MHz (FIG. 29G). These studies will provide important data regarding the physiological roles of these two neural populations. Overall, these studies will employ NICE to dissect the contribution and the interaction of specific neuronal populations to a complex behavior, feeding, in freely moving animals. These studies also provide a basis for using the method to probe the role of other neural populations to control feeding and other behaviors.

In summary, a combination of nanoparticle heating in an RF field with defined expression of a cell surface tag for targeted nanoparticle binding will be used together with a temperature responsive ion channel to convert localized temperature changes into remote, temporally controlled and anatomically defined cell activation. Using the current in vitro system validation of this technique has been conducted to show that NICE results in a significant increase in intracellular calcium and can thereby stimulate calcium dependent gene expression. The cellular responses to NICE will be examined and validation combinatorial cell activation. The novel technology will be used to modulate hormone release in vitro and in vivo and to modify neural activity in vitro and in vivo to investigate feeding behavior. Together these studies will further support the use of NICE as a tool for external, non-invasive, specific cell excitation and the employment of NICE as a unique methodology to investigate the effects of specific cell stimulation.

Example 6

Cell Based Nanoparticle Therapy for Diabetes

Transfecting cells with the ferritin construct resulted in the distribution of nanoparticles throughout the cell cytoplasm and with an average distance of the ferritin nanoparticle to the TRPV ion channel approximately equal to the cell radius. Previous mathematical modeling predicts that particles within 200 nm would lead to sufficient heating to trigger channel activation (Huang et al., Nat. Nanotechnology 5:602-606). The number of ferritin nanoparticles were therefore quantified within 200 nm of the cell membrane by EM. It was found that there are 12.6±2.86 particles per 0.2 $\mu m^2$ with an average distance to the cell membrane of 60.3±2.85 mn. This distance is not dissimilar from the average distance between nanoparticles bound to transmembrane biotin acceptor protein tether (100 nm). Assuming the ferritin particles are evenly distributed through the cell, this would give $5\times10^8$ ferritin particles/$cm^3$. This is in considerable excess of the 1.1 pg of iron ($5\times10^5$ nanoparticles assuming ferritin has a similar composition to iron oxide nanoparticles but 10 nm diameter) calculated to be necessary to achieve a 5° C. increase in temperature.

Results

Diseases related to tissue loss have traditionally been treated by pharmacological replacement of cell secretory products, such as insulin or dopamine, and more recently by organ or cell transplantation from cadaveric donors. Pharmacological therapies often have side effects and effective means of delivering peptide drugs in particular are limited. However, more physiological treatments such as allogenic cell implantation are hampered by lack of donors and the necessity of long term immunosuppression. Therefore, a technique which allows precise, remote activation of defined cells to trigger gene expression and peptide release in vivo offers potential as a cell replacement therapy as well as a tool for basic research.

The importance of developing means for activating specific cells has been widely appreciated as evidenced by the use of direct stimulation through implanted electrodes. However this approach is limited by variable activation, the need for permanent implants, and tissue damage. In addition this technique does not allow selective activation of specific cells. An alternative approach makes use of drug inducible systems to alter gene expression or ion channels to modulate cell activity. While drug inducible gene expression systems do allow cellular specificity, they typically have a relatively slow onset of action. In contrast, ion channels rapidly regulate intracellular ion concentrations by allowing the selective passage of cations or anions, and in turn modulate intracellular functions in a cell specific manner. The use of ion channels has many advantages; their structure and function are relatively well described, they have a rapid time course of activation and a broad range of channels exist in mammalian and non-mammalian cells, which may be exploited in the search for the optimum means of modifying cellular activity. Recently, the non-mammalian channelrhodopsin (ChR2) gene, a light activated cation, has been employed to rapidly activate molecularly defined neurons when exposed to blue light. This system gives anatomical specificity and temporal control but requires fiber optic light delivery via invasive chronic implanted devices because light penetration is relatively poor. Thus a means for activating ion channels without the requirement of an implanted device could represent an important potential means for activating cells. Describe herein is a means for non-invasive excitation of a defined cell population in vivo using a radiofrequency field to heat iron oxide nanoparticles which in turn activate the temperature sensitive TRPV1 channel to trigger calcium entry. Calcium influx in turn activates gene expression and in the current system, hormone release. This approach has been validated by modulating the expression and secretion of the peptide hormone, insulin, and shown that it can be used to lower blood glucose in mice.

Remote Activation of Cells Using Metal Nanoparticles and an Epitope Tagged Temperature Sensitive Channel.

In order to activate cells and tissues non-invasively, it is necessary to have a signal that is capable of passing through tissue. Radiofrequency (RF) signals at low and medium frequencies penetrate tissues freely and without significant energy absorption. In contrast, metallic/metal oxide nanoparticles placed in an alternating RF field absorb energy and heat in a controlled manner dependent on particle size (FIG. 12) and the field strength. In vitro, the temperature response achieved is fast and decays quickly (inverse of the square of the distance) thus potentially providing a rapid, highly localized 'on-off' switch. Metal nanoparticles can readily be functionalized to target to defined cell populations by coating with specific antibodies that recognize proteins that are normally expressed on a cell or transfected into that cell. Thus, nanoparticles are well suited for inducing cell surface temperature changes that can be transduced into cellular responses by temperature sensitive channels in vitro and in vivo.

The local temperature change achieved by exposing nanoparticle-coated cells to radiowaves can be transduced into calcium entry by targeted expression of TRPV1 channel. This single component, cell surface cation channel detects small changes in temperature just above the physiological range (>42° C.) and undergoes a conformational change allowing calcium entry. The response is proportional to the temperature change and relatively rapid, thus transducing temperature variations induced by the heated nanoparticles into a graded calcium current with attendant cell activation. In addition these channels do not desensitize after repeated activation as repeated heating potentiates calcium entry.

The method described herein makes use of metal nanoparticles, directed to specific cells, and TRPV1 ion channels to remotely stimulate cell activity and gene expression as follows. A single construct encoding TRPV1, modified to incorporate a unique extracellular His×6 epitope tag was expressed in specific cells (TRPV1His). Iron oxide (IO) nanoparticles functionalized with monoclonal antibodies against the His×6 epitope tag are targeted to these cells. In the presence of a RF field, local heating of IO nanoparticles above the threshold for TRPV1 channel activation (42° C.) triggers calcium entry and cell activation (FIG. 1). The increase in intracellular calcium then activates gene expression under the control of a calcium dependent NFAT promoter in which the calcium activated protein serine/threonine phosphatase, calcineurin, dephosphorylates the regulatory domain of NFAT, (nuclear factor of activated T cells), allowing its translocation into the nucleus where it activates the transcription of genes downstream of NFAT response elements.

Reports have described a two component system using a biotinylated transmembrane protein as a nanoparticle anchor and a separate TRPV1 to induce calcium entry, hereafter called V1 BAP (FIG. 8A). A single component system was benchmarked against this dual component system and both systems were used to control gene expression and hormone release in vitro before using the novel single component system to regulate gene expression and hormone release in vivo.

Nanoparticle Decoration of Cells In Vitro.

Figure 31:
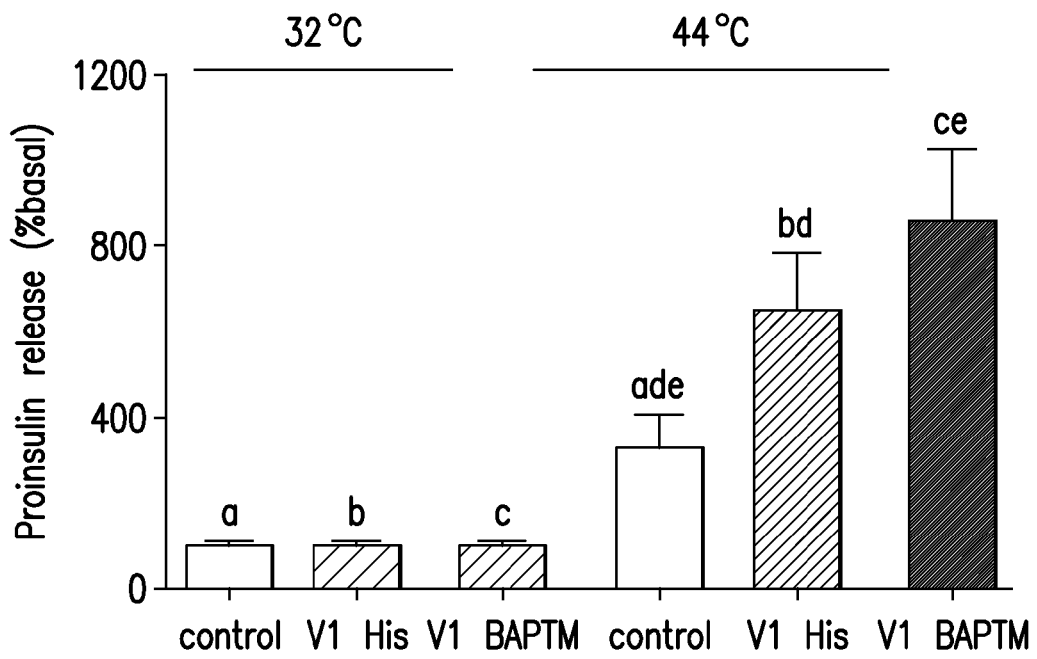
FIG. 31. Depiction of a modified TRPV1 channel as both a nanoparticle tether and effector. A short epitope tag, His×6, was introduced into the first extracellular loop of TRPV1. Modification did not significantly alter the temperature sensing ability of TRPV1.

A modified TRPV1 channel was used as both a nanoparticle tether and effector. A short epitope tag, His×6, was introduced into the first extracellular loop of TRPV1. Modification did not significantly alter the temperature sensing ability of TRPV1 (FIG. 31). This site is exposed to extracellular signals but distant from putative temperature and voltage sensing sequences and the pore region of TRPV1. Modifying the channel to act as the tether offers several advantages. Firstly, by increasing the proximity of nanoparticle binding and temperature sensing the effect of heat dissipation from the nanoparticle is reduced. This may reduce the density of nanoparticle binding required to achieve TRPV1 opening. Secondly, a single construct is readily targeted to defined cell populations using defined promoters. Finally, conditional expression can be controlled by recombinases such as cre or Flp.

Figure 30B:
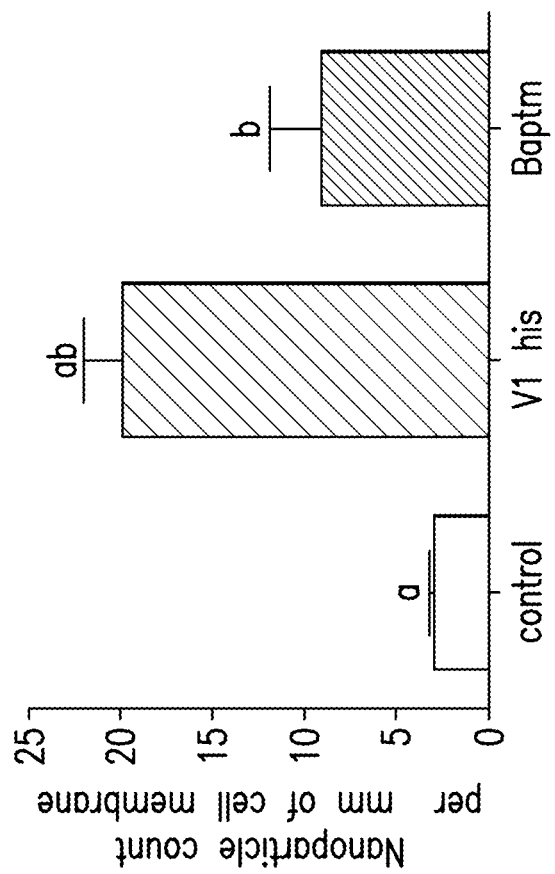
FIG. 30. Iron oxide (IO) nanoparticles functionalized with monoclonal antibodies against the His×6 epitope tag are targeted to cells. (A-B) In the presence of a RF field, local heating of IO nanoparticles above the threshold for TRPV1 channel activation (42° C.) triggers calcium entry and cell activation.
Figure 30A:
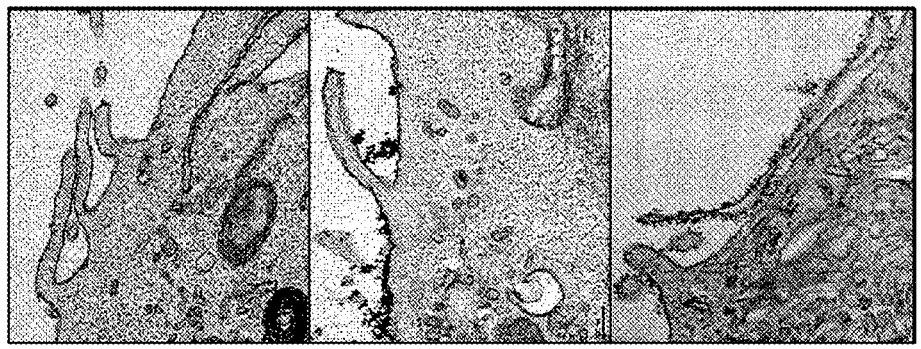

Functionalized iron oxide nanoparticles were used to decorate the cells. Size dependent heating of IO nanoparticles occurred at 465 kHz with maximum heating achieved using an aqueous solution of 20 nm diameter particles. With an alternating magnetic field (465 kHz,), an increase of up to 17° C. can be achieved in a suspension of 20 nm iron oxide particles (1 mg/ml) (FIG. 2A) with an initial heating rate of 0.15° C./s. A 5° C. rise in nanoparticle temperature above body temperature is sufficient to open TRPV1 channels and can be reached in 30 s. Nanoparticles of this size are within the limits of the extracellular space and therefore able to diffuse. IO nanoparticles (20 nm) functionalized with monoclonal anti-His antibody bind to TRPV1His expressed in transfected human embryonic kidney (HEK 293) cells. There is a significant increase in nanoparticle binding in cells transfected with TRPV1His (19.78±2.23 nanoparticles per mm cell membrane) compared to untransfected cells (2.85±0.32 nanoparticles per mm cell membrane) (FIGS. 30A and B) and greater than the density achieved with streptavidin functionalized IO nanoparticles bound to cells expressing the two component system, TRPV1 BAP (9.07±2.85 nanoparticles per mm cell membrane). In these studies, the results of the one component system (an epitope tagged TRPV1) was compared to a previously published two component system that uses a biotinylated transmembrane protein as a nanoparticle anchor and a separate TRPV1 to induce calcium entry, hereafter called V1 BAP (FIG. 8A) were compared. This two component system has been tested in vitro.

Nanoparticle Activated Insulin Expression and Release In Vitro.

Figure 19A:
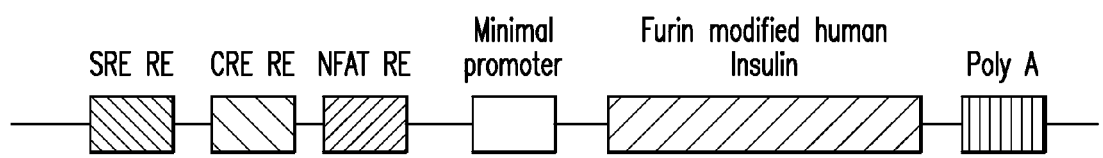
FIG. 19. (A) A synthetic promoter comprised of three calcium response elements: serum response element (SRE), cyclic AMP response element (CRE) and nuclear factor of activated T-cell response element (NFAT RE) and a minimal promoter were cloned upstream of a modified, furin sensitive insulin cDNA. HEK 293t cells expressing calcium dependent human insulin and either TRPV1His or TRPV1 BAP were decorated with functionalized IO nanoparticles. Applying a RF magnetic field to nanoparticle-decorated cells expressing TRPV1His or TRPV1 BAP and calcium regulated furin sensitive insulin significantly increased proinsulin release and insulin gene expression. The increases in proinsulin release are blocked by the non-specific TRP channel inhibitor, ruthenium red. There was a trend towards an increase in proinsulin release after 15 mins of RF treatment, presumably initially through the release of preformed insulin containing vesicles and with a significant increase in release at 1 hour (D), whilst insulin gene expression begins to increase after 45 minutes and also becomes significant at 1 hour (E). The effects of RF dependent heating of IO nanoparticles were confined to decorated cells since there was no release of proinsulin when cells expressing BAPTM as a nanoparticle tether are mixed with, and therefore adjacent to, cells expressing TRPV1 and calcium regulated furin sensitive insulin. This time course is similar to the expression of c-fos, a gene whose expression is also calcium dependent. To assess cell viability, immunohistochemistry was used to quantify two markers of apoptosis— active caspase 3 and terminal deoxynucleotidyl transferase dUTP nick end labeling (TUNEL). No differences in immunopositive cell counts were observed between TRPV1His transfected 239t cells treated with nanoparticles alone and those treated with nanoparticles and RF magnetic field application (G and H).

In order to assess the potential anti-diabetic effects of this system, the modified TRPV1 construct and an NFAT-insulin construct was introduced into PC12 cells as well as 293T cells. These cells process and secrete proteins in response to increased intracellular Ca++. A synthetic promoter comprised of three calcium response elements: serum response element (SRE), cyclic AMP response element (CRE) and nuclear factor of activated T-cell response element (NFAT RE) and a minimal promoter were cloned upstream of a modified, furin sensitive insulin cDNA (FIG. 19A). Processing of proinsulin to insulin relies on two beta cell specific prohormone convertases so a modified human proinsulin with engineered furin cleavage sites was used. This expressed protein is processed to mature insulin in non beta cells both in vitro and in vivo (Shifrin et al., gene Ther. 8:1480-1489) and its release can be differentiated from endogenous murine insulin release in vivo. Like beta cells, cells expressing furin sensitive insulin synthesize both proinsulin and insulin and the ratio of proinsulin to insulin varies both with cell type and basal vs activated state.

Figure 19B:
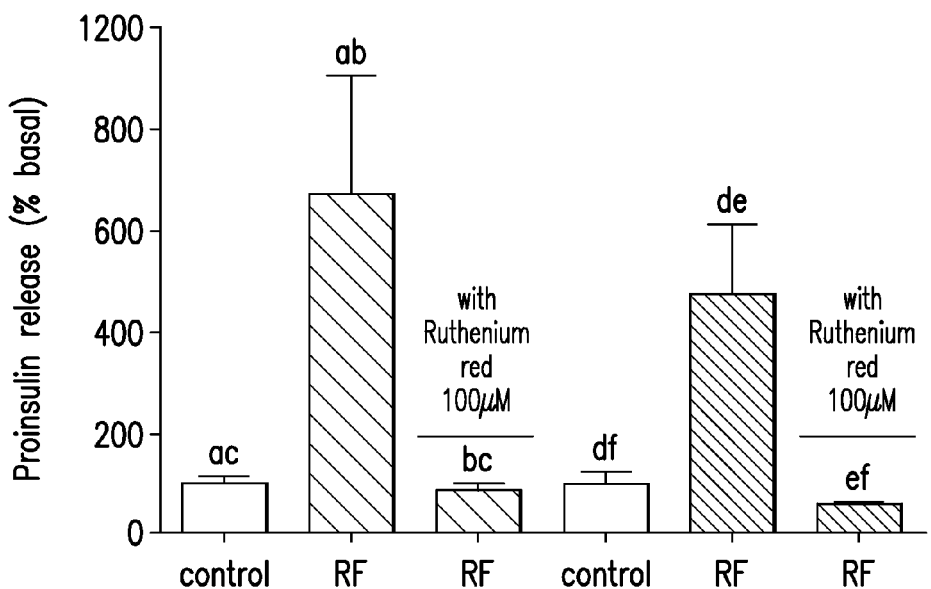
Figure 19C:
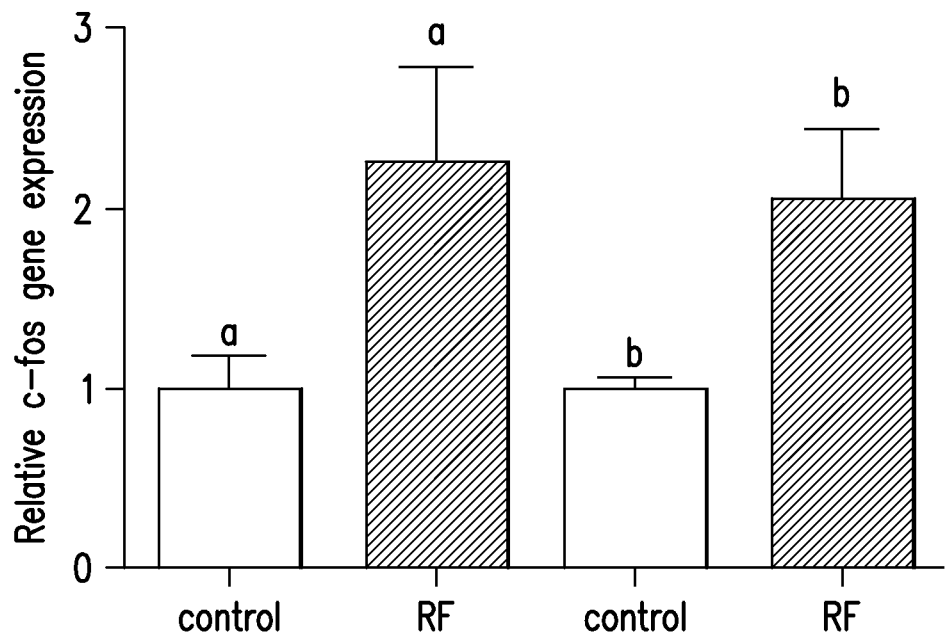
Figure 19D:
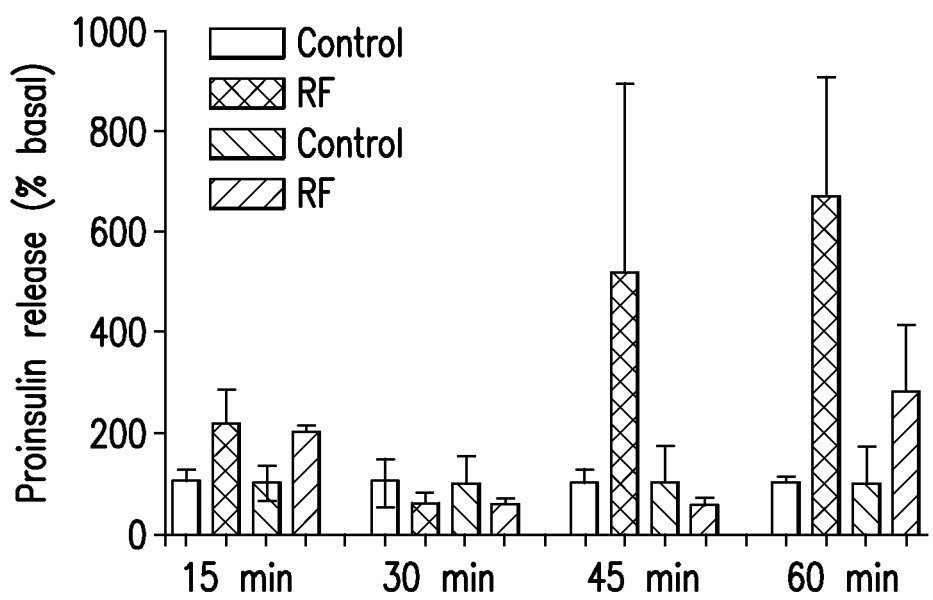
Figure 19E:
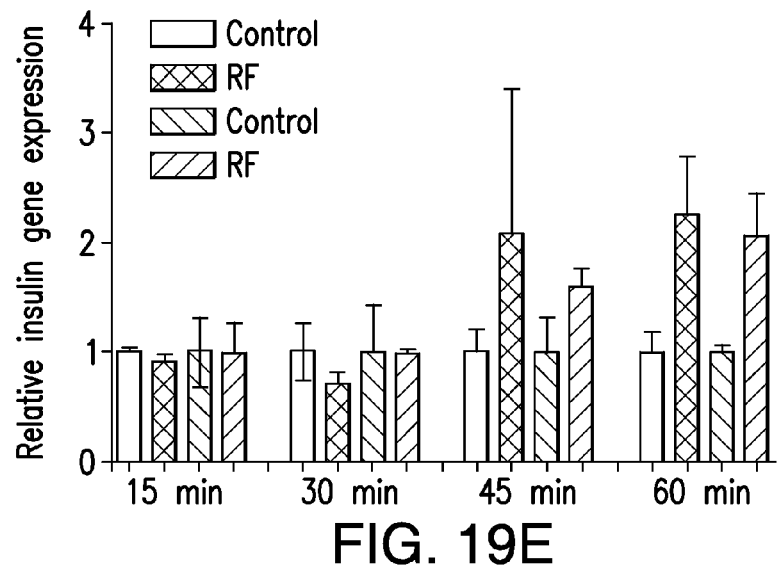

HEK 293t cells expressing calcium dependent human insulin and either TRPV1His or TRPV1 BAP were decorated with functionalized IO nanoparticles. Applying a RF magnetic field to nanoparticle-decorated cells expressing TRPV1His or TRPV1 BAP and calcium regulated furin sensitive insulin significantly increased proinsulin release (FIG. 19B) (TRPV1His: control 100±13.94% basal, RF treated 671±234.9% basal. TRPV1 BAP: control 100±23.96% basal, RF treated 477.4±136.1% basal) and insulin gene expression (FIG. 19C) (TRPV1His: control 1.0±0.18, RF treated 2.20±0.53 relative gene expression, $p<0.05$. TRPV1 BAP: control 1.0±0.06, RF treated 2.06±0.38 relative gene expression, $p<0.05$). The increases in proinsulin release are blocked by the non-specific TRP channel inhibitor, ruthenium red (FIG. 19B). There was a trend towards an increase in proinsulin release after 15 mins of RF treatment, presumably initially through the release of preformed insulin containing vesicles and with a significant increase in release at 1 hour (FIG. 19D), whilst insulin gene expression begins to increase after 45 minutes and also becomes significant at 1 hour (FIG. 19E). This time course is similar to the expression of c-fos, a gene whose expression is also calcium dependent.

Figure 19F:
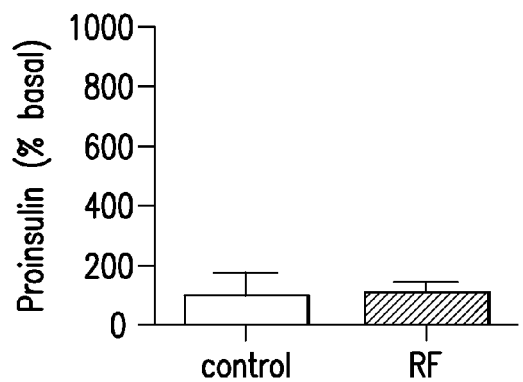
Figure 32:
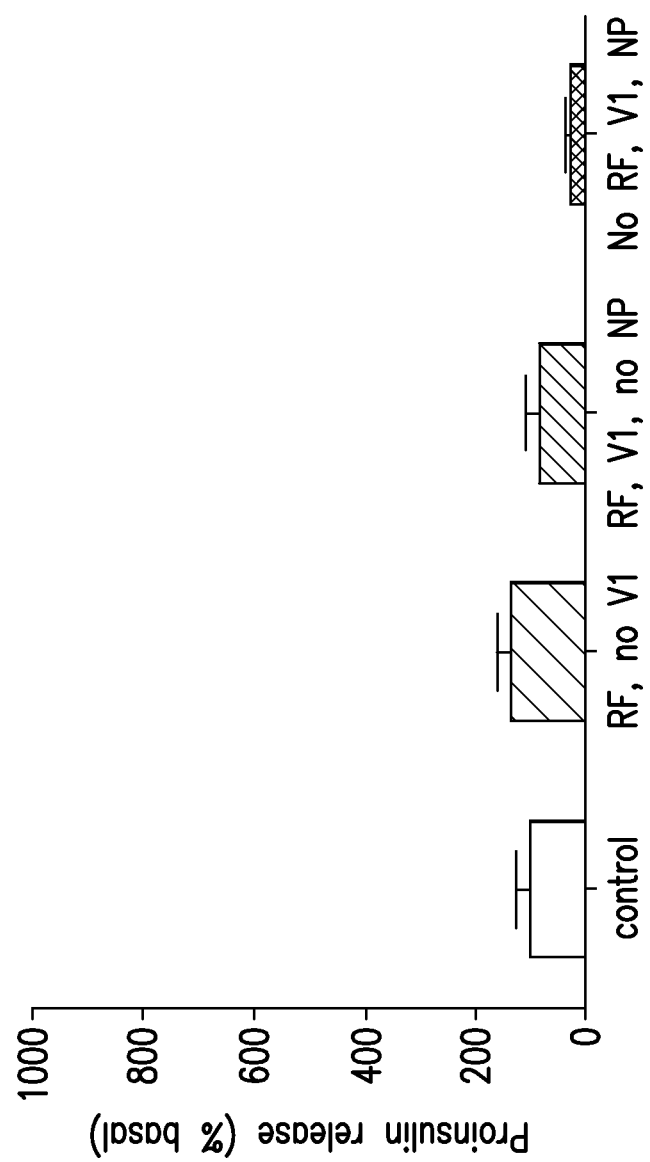
FIG. 32. No significant increase in proinsulin release was observed in HEK 293t cells decorated with IO nanoparticles in the presence of an RF magnetic field without TRPV1 (transfected with BAP only), in cells with TRPV1 but without nanoparticle binding (transfected with TRPV1 only), or in cells with nanoparticles and TRPV1 (TRPV1$^{His}$ or TRPV1 BAP) but in the absence of the RF magnetic field.

The effects of RF dependent heating of IO nanoparticles were confined to decorated cells since there was no release of proinsulin when cells expressing BAPTM as a nanoparticle tether are mixed with, and therefore adjacent to, cells expressing TRPV1 and calcium regulated furin sensitive insulin (FIG. 19F) (Proinsulin release: control 100±78% basal, RF treatment 109±38.2% basal). Proinsulin release only occurs when all components of the system are present: TRPV1, nanoparticles and RF magnetic field. No significant increase in proinsulin release was observed in HEK 293t cells decorated with IO nanoparticles in the presence of an RF magnetic field without TRPV1 (transfected with BAP only), in cells with TRPV1 but without nanoparticle binding (transfected with TRPV1 only), or in cells with nanoparticles and TRPV1 (TRPV1His or TRPV1 BAP) but in the absence of the RF magnetic field (FIG. 32).

Figure 19G:
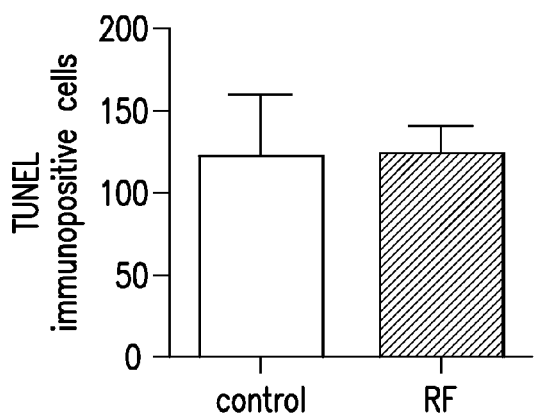
Figure 19H:
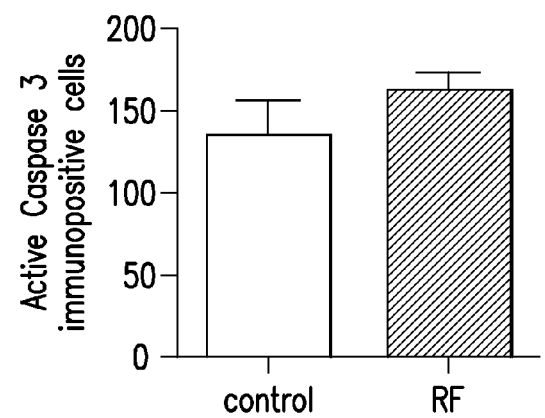

To assess cell viability, immunohistochemistry was used to quantify two markers of apoptosis-active caspase 3 and terminal deoxynucleotidyl transferase dUTP nick end labeling (TUNEL). No differences in immunopositive cell counts were observed between TRPV1His transfected 239t cells treated with nanoparticles alone and those treated with nanoparticles and RF magnetic field application (FIGS. 19G and H) (TUNEL: control 123±37 cells, RF treatment 124±17 cells. Activated Caspase-3: control 136±21 cells, RF treatment 163±11 cells).

Nanoparticle Regulation of Blood Glucose In Vivo.

Figures 33A, 33B:
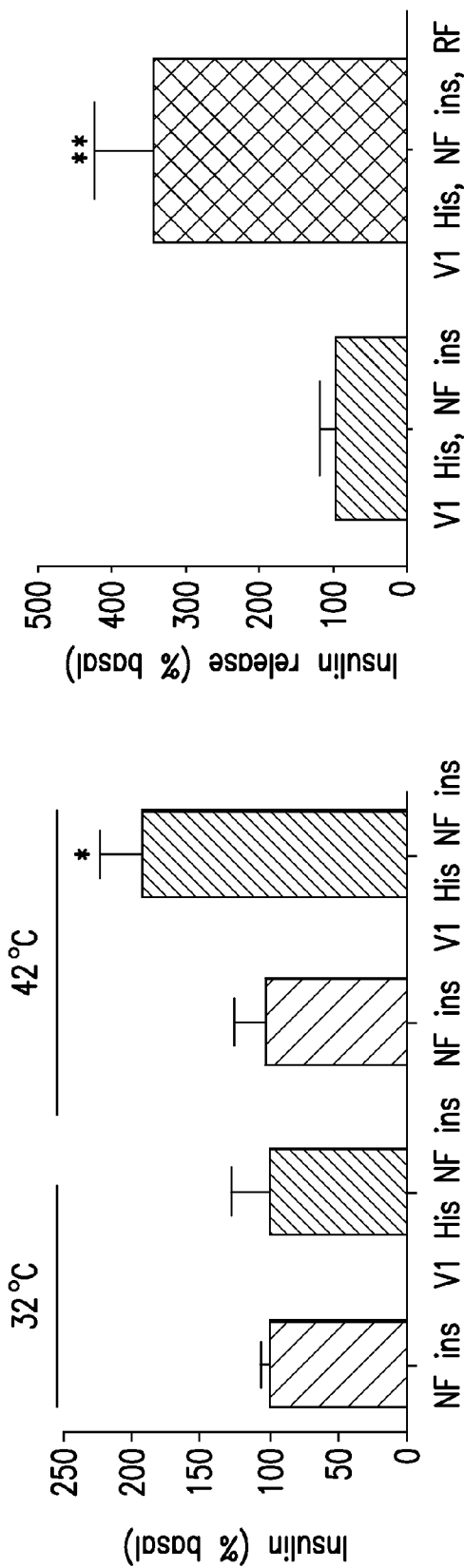
FIG. 33. In vitro studies examining the effects of RF treatment on proinsulin release and insulin gene expression replicated the findings in transfected HEK 239t cells (A-C). Stably transfected PC12-TRPV1His-Ins cells were injected subcutaneously into the flank of nude mice and formed tumors expressing TRPV1His (D) and furin sensitive insulin constructs. Following an overnight fast, PBS or IO nanoparticles were injected into the tumors of anesthetized mice (50 ul total volume, nanoparticle concentration 8 mg/ml). Blood glucose and plasma insulin were measured before, during and after the application of an RF field (E).
Figure 33C:
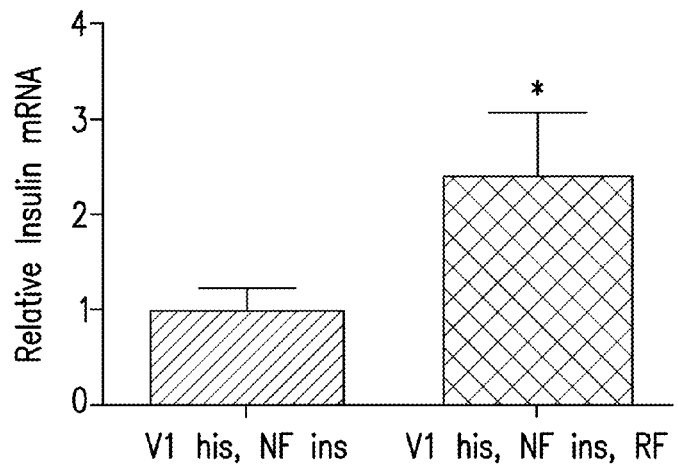
Figure 33D:
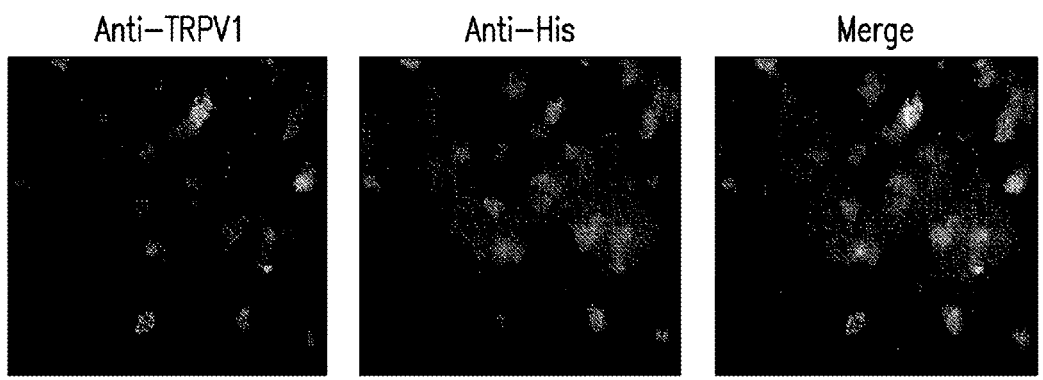
Figure 33E:
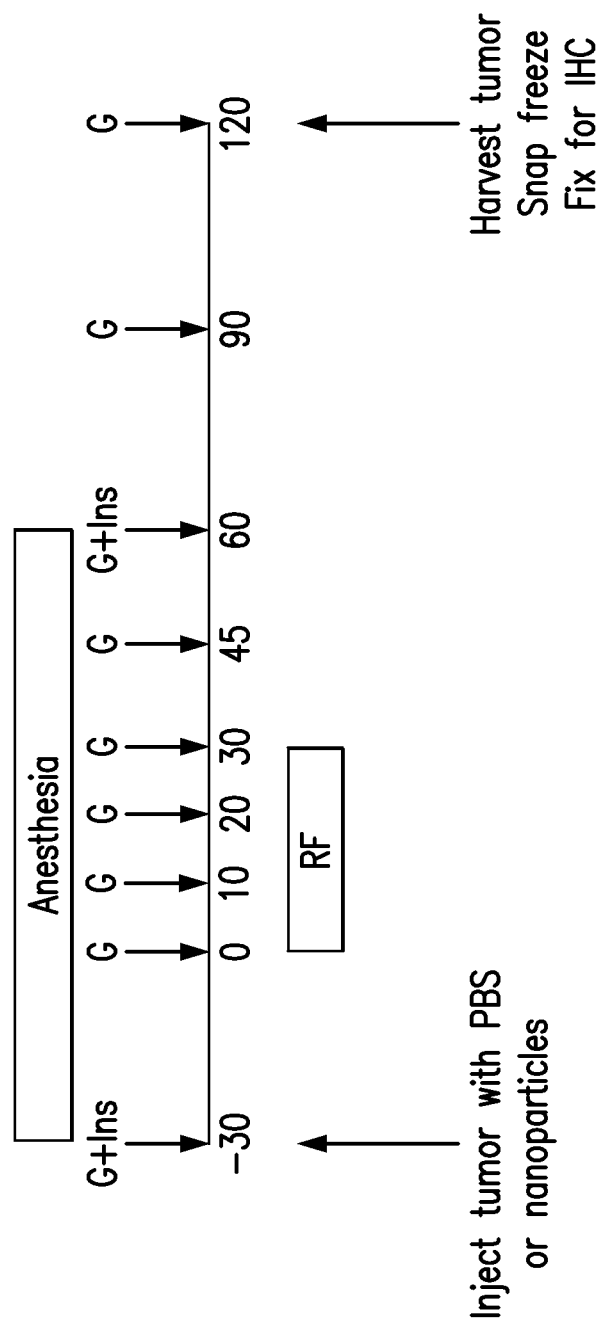

Experiments were conducted to translate in vitro findings in vivo by testing whether the remote activation of proinsulin gene expression, insulin synthesis and release could modulate blood glucose in mice. Stably transfected PC12 cells expressing TRPV1His and calcium regulated furin sensitive insulin were established. As above, this endocrine cell line is capable of synthesizing and secreting mature insulin. In vitro studies examining the effects of RF treatment on proinsulin release and insulin gene expression replicated the findings in transfected HEK 239t cells (FIG. 33A-C). Stably transfected PC12-TRPV1His-Ins cells were injected subcutaneously into the flank of nude mice and formed tumors expressing TRPV1His (FIG. 33D) and furin sensitive insulin constructs. Following an overnight fast, PBS or IO nanoparticles were injected into the tumors of anesthetized mice (50 ul total volume, nanoparticle concentration 8 mg/ml). Blood glucose and plasma insulin were measured before, during and after the application of an RF field (See FIG. 33E). Applying the RF magnetic field resulted in significant decrease in blood glucose in mice treated with IO nanoparticles compared with those receiving PBS followed by RF treatment (FIG. 10A)($\Delta$ Blood glucose at 30 mins: PBS control −10.99±9.72, nanoparticle treated −53.62±8.90, p<0.05. At 45 mins: PBS control −9.74±8.52, nanoparticle treated −60.88±11.59, p<0.05. At 60 mins: PBS control −6.24±15.29, nanoparticle treated −55.12±13.15, p<0.05). There was a significant difference in the cumulative change in blood glucose between PBS and nanoparticle treated mice over the course of the study (FIG. 10B) (TRPV1His, NF Ins AUC (0-120 min): PBS treated 271.7±691.6, nanoparticle treated −2695±858.3 mgdl-1 min, p<0.05). Plasma insulin was also significantly increased in mice receiving nanoparticle injection and RF magnetic field treatment but remained unchanged in control mice injected with PBS (FIG. 10C) (Plasma insulin: PBS (−30 min) 1.83±0.380 μIU/ml, PBS (30 min) 1.75±0.360 μIU/ml, nanoparticles (−30 min) 2.26±0.760 μIU/ml, nanoparticles (30 min) 3.25±0.640 μIU/ml, p<0.05). In addition, proinsulin mRNA levels were significantly higher in nanoparticle injected tumors treated with RF magnetic field compared to those injected with nanoparticles alone (FIG. 10D) (Control: 1.0±0.2 relative insulin gene expression, RF treated: 2.03±0.3 relative insulin gene expression, p<0.05). There was no difference in apoptosis, assessed as before by TUNEL and activated caspase-3, between nanoparticle injected tumors in the presence or absence of the RF magnetic field (FIGS. 10E and F)(TUNEL: control 56.4±9.8 cells, RF 48.8±8.9 cells. Active Caspase 3: control 199.8±27.4 cells, RF 168±24.4 cells)

To ensure the effects on blood glucose were not the result of non-specific release of insulin due to thermal effects of nanoparticles on the tumor, the in vivo study was repeated using PC12 cells established to stably express calcium regulated furin sensitive insulin alone without TRPV1His and it was found that there was no significant effect on blood glucose in mice injected with PBS or nanoparticles with RF magnetic field application (FIG. 12). Nor was there a cumulative change in blood glucose (FIG. 10B) (NF Ins AUC (0-120 min): PBS treated 1851±1126 mgdl-1 min, nanoparticle treated 1281±1758 mgdl-1 min) or in plasma insulin levels (FIG. 10C) (Plasma insulin: PBS (−30 min) 1.77±0.310 μIU/ml, PBS (30 min) 1.31±0.150 μIU/ml, nanoparticles (−30 min) 1.2±0.170 μIU/ml, nanoparticles (30 min) 1.17±0.230 μIU/ml). Finally, there was no difference in proinsulin mRNA expression between nanoparticle-injected NF Ins tumors with or without RF magnetic field treatment (FIG. 10D) (Control: 1.0±0.4 relative insulin gene expression, RF treated: 1.0±0.2 relative insulin gene expression). Intratumoral temperatures did not differ between RF treated PC12 TRPV1His-Ins and PC12 Ins tumors (FIGS. 12B and 12C). Thus the release of insulin and lowering of blood glucose requires the presence of the particles, the modified TRPV1 channel and the NFAT-insulin construct. These findings demonstrate that magnetic field heating of nanoparticles coupled to TRPV1 activation remotely and specifically regulates proinsulin mRNA synthesis and insulin release to reduce blood glucose.

The development of a cell based system for remotely activating cells and its utility for lowering blood glucose in mice is demonstrated herein. There have been relatively few advances in the therapies available for diseases caused by tissue loss—the mainstay of treatment remains pharmacological replacement often with marked side effects. Remote modulation of cell activity and downstream functions such as gene expression, protein synthesis and secretion combined with developments in stem cell therapy offers the prospect of more physiological therapies in the form of engineered autografts. Nanoparticle dependent calcium entry could be used to regulate not only hormone release but also functions such as neural activity or muscle contraction.

The system described herein can be further modified to achieve combinatorial activation of different cells. Cell populations expressing TRPV1 engineered to incorporate unique epitope tags could be decorated with different nanoparticles designed to heat in response to distinct RF frequencies allowing combinatorial cell activation and peptide release. For example, gold nanoparticles, could be labeled with a second antibody to a different epitopes on the modified TRPV1 channel in cells engineered to express glucagon. This would enable one to either lower or raise blood glucose depending on the ambient blood glucose concentration.

These studies provide a platform for developments using different types of nanoparticles with enhanced characteristics. For example, refinements in nanoparticle structures could be used to depolarize cells without the need for a TRP channel; this advance would allow the direct activation of cells using nanoparticles with antibodies directed against specific cell surface epitopes. It may also be possible to engineer cells that express nanoparticles intracellularly thus obviating the need for injecting particles.

The present invention is not to be limited in scope by the specific embodiments described herein which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the claims. Various publications are cited herein, the contents of which are hereby incorporated, by reference, in their entireties.

What is claimed:

1. A method to remotely modulate the activity of a cell type of interest, the method comprising: (a) administering to a cell population nanoparticles selective for a temperature sensitive channel within the cell type of interest; and (b) applying a radiofrequency field to remotely activate the nanoparticles, wherein said activation of the nanoparticles results in modulation of the activity of the cell type of interest.

2. The method of claim 1, wherein the activation of the nanoparticles results in an increase in the temperature of the particles and the temperature sensitive channel.

3. The method of claim 2, wherein the temperature sensitive channel is selected from the group consisting of TRPV1, TRPV2, TRPV3, TRPM8, chimeric TRP channels, and tandem pore domain potassium channels.

4. The method of claim 1, wherein the cell type of interest is a stem cell.

5. The method of claim 1, wherein the nanoparticles comprise metallic or metal oxide nanoparticles.

6. A method to remotely modulate the activity of a cell type of interest in a subject, the method comprising: (a) administering to the subject nanoparticles selective for a temperature sensitive channel within the cell type of interest; and (b) applying a radiofrequency field to remotely activate the nanoparticles, wherein said activation of the nanoparticles results in modulation of the activity of the cell type of interest in a subject.

7. The method of claim 6, wherein activation of the nanoparticles results in an increase in the temperature of the particles and the temperature sensitive channel.

8. The method of claim 7, wherein the temperature sensitive channel is the TRPV1 channel.

9. The method of claim 6, wherein the cell type of interest is a stem cell.

10. The method of claim 6, wherein the nanoparticles comprise metallic or metal oxide nanoparticles.

11. A method to modulate the activity of a cell type of interest in a subject, the method comprising steps: (a) administering to the subject modified cells of interest that comprise nanoparticles that are selective for a temperature sensitive channel within the cell type of interest; and (b) applying a radiofrequency field to remotely activate the nanoparticles, wherein said activation of the nanoparticles results in modulation of the activity of the cell type of interest in a subject.

12. The method of claim 11, wherein activation of the nanoparticles results in an increase in the temperature of the particles and the temperature sensitive channel.

13. The method of claim 12, wherein the temperature sensitive channel is the TRPV1 channel.

14. The method of claim 11, wherein the cell type of interest is a stem cell.

15. The method of claim 11, wherein the nanoparticles comprise metallic or metal oxide nanoparticles.

16. The method of claim 11, wherein the nanoparticle is an intracellularly expressed nanoparticle.

17. The method of claim 16, wherein the nanoparticle is ferritin.

18. The method of claim 16, wherein the nanoparticle is a ferritin fusion protein.

19. The method of claim 1, wherein the temperature sensitive channel comprises TRPV1.

20. The method of claim 3, wherein the tandem pore domain potassium channel comprises: TREK1, TREK2, or TASK.

21. The method of claim 1, wherein the temperature sensitive channel comprises a fusion protein.

22. The method of claim 21, wherein the fusion protein comprises a tag.

23. The method of claim 22, wherein the tag comprises: a nanobody peptide, His tag, or biotin acceptor protein.

24. The method of claim 1, wherein the nanoparticles comprise: ferritin, MagA, ceruloplasmin, or transferrin.

25. The method of claim 1, wherein the nanoparticles comprise a targeting moiety.

26. The method of claim 25, wherein the targeting moiety comprises: antibody, streptavidin, or peptide.

* * * * *